United States Patent
Gray et al.

(10) Patent No.: US 11,932,646 B2
(45) Date of Patent: Mar. 19, 2024

(54) SMALL MOLECULE MYRISTATE INHIBITORS OF Bcr-abl AND METHODS OF USE

(71) Applicants: Dana-Farber Cancer Institute, Inc., Boston, MA (US); The Scripps Research Institute, La Jolla, CA (US)

(72) Inventors: Nathanael S. Gray, Boston, MA (US); Jianming Zhang, Belmont, MA (US); Barun Okram, San Marcos, CA (US); Xianming Deng, Fujian (CN); Jae Won Chang, San Diego, CA (US); Amy Wojciechowski, Cheektowaga, NY (US)

(73) Assignees: THE SCRIPPS RESEARCH INSTITUTE, La Jolla, CA (US); DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 17/574,132

(22) Filed: Jan. 12, 2022

(65) Prior Publication Data
US 2022/0135573 A1    May 5, 2022

Related U.S. Application Data

(60) Continuation of application No. 16/933,095, filed on Jul. 20, 2020, now Pat. No. 11,254,682, which is a division of application No. 16/170,921, filed on Oct. 25, 2018, now Pat. No. 10,787,455, which is a division of application No. 15/582,004, filed on Apr.
(Continued)

(51) Int. Cl.
| | | |
|---|---|---|
| C07D 239/94 | (2006.01) |
| A61K 31/517 | (2006.01) |
| A61K 31/519 | (2006.01) |
| A61K 31/52 | (2006.01) |
| A61K 31/5377 | (2006.01) |
| A61K 31/7076 | (2006.01) |
| A61K 45/06 | (2006.01) |
| A61P 9/00 | (2006.01) |
| A61P 17/00 | (2006.01) |
| A61P 19/00 | (2006.01) |
| A61P 35/00 | (2006.01) |
| A61P 35/02 | (2006.01) |
| C07D 239/42 | (2006.01) |
| C07D 403/04 | (2006.01) |
| C07D 403/06 | (2006.01) |
| C07D 403/12 | (2006.01) |
| C07D 417/04 | (2006.01) |
| C07D 471/04 | (2006.01) |
| C07D 473/34 | (2006.01) |
| C07D 487/04 | (2006.01) |
| C07D 495/04 | (2006.01) |
| C07H 19/16 | (2006.01) |

(52) U.S. Cl.
CPC .......... *C07D 487/04* (2013.01); *A61K 31/517* (2013.01); *A61K 31/519* (2013.01); *A61K 31/52* (2013.01); *A61K 31/5377* (2013.01); *A61K 31/7076* (2013.01); *A61K 45/06* (2013.01); *A61P 9/00* (2018.01); *A61P 17/00* (2018.01); *A61P 19/00* (2018.01); *A61P 35/00* (2018.01); *A61P 35/02* (2018.01); *C07D 239/42* (2013.01); *C07D 239/94* (2013.01); *C07D 403/04* (2013.01); *C07D 403/06* (2013.01); *C07D 403/12* (2013.01); *C07D 417/04* (2013.01); *C07D 471/04* (2013.01); *C07D 473/34* (2013.01); *C07D 495/04* (2013.01); *C07H 19/16* (2013.01); *Y02A 50/30* (2018.01)

(58) Field of Classification Search
CPC .................................................... C07D 239/42
See application file for complete search history.

(56) References Cited

U.S. PATENT DOCUMENTS

| | | |
|---|---|---|
| 6,492,383 B1 | 12/2002 | Munchhof et al. |
| 6,638,939 B2 | 10/2003 | Uckun et al. |

(Continued)

FOREIGN PATENT DOCUMENTS

| | | |
|---|---|---|
| WO | WO 98/12184 | 3/1998 |
| WO | WO 00/56720 A1 | 9/2000 |

(Continued)

OTHER PUBLICATIONS

CAS registry No. 929457-25-0, available Apr. 9, 2007.*
(Continued)

*Primary Examiner* — Susanna Moore
(74) *Attorney, Agent, or Firm* — Crowell & Moring LLP; Yuezhong Feng

(57) ABSTRACT

The present disclosure provides novel heteroaryl compounds of formula (VII). Such compounds are useful for the treatment of cancers.

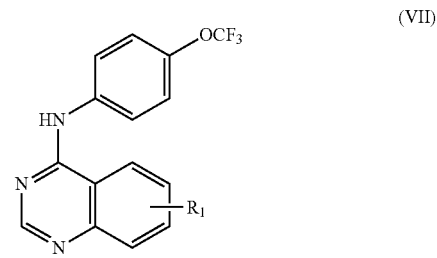

(VII)

4 Claims, No Drawings

Related U.S. Application Data 28, 2017, now abandoned, which is a continuation of application No. 14/540,919, filed on Nov. 13, 2014, now Pat. No. 9,670,214, which is a continuation of application No. 12/745,496, filed as application No. PCT/US2008/013219 on Nov. 28, 2008, now Pat. No. 8,921,336.

(60) Provisional application No. 61/004,462, filed on Nov. 28, 2007.

(56) References Cited

U.S. PATENT DOCUMENTS

| | | |
|---|---|---|
| 6,962,915 B2 | 11/2005 | Das et al. |
| 2004/0132786 A1 | 7/2004 | Chyba et al. |
| 2005/0014753 A1 | 1/2005 | Ding et al. |
| 2005/0043328 A1 | 2/2005 | Dolezal |
| 2005/0222177 A1 | 10/2005 | Sim et al. |
| 2007/0009977 A1 | 1/2007 | Boyce et al. |
| 2007/0191380 A1 | 8/2007 | Ding et al. |
| 2010/0143341 A1 | 6/2010 | Taylor et al. |

FOREIGN PATENT DOCUMENTS

| | | |
|---|---|---|
| WO | WO 02/04690 | 1/2002 |
| WO | WO 02/47690 A1 | 6/2002 |
| WO | WO 03/040144 A2 | 5/2003 |
| WO | WO 03/062209 A2 | 7/2003 |
| WO | WO 2004/058713 A1 | 7/2004 |
| WO | WO 2005/039486 A2 | 5/2005 |
| WO | WO 2005/047288 A1 | 5/2005 |
| WO | WO 2006/034473 A2 | 3/2006 |

OTHER PUBLICATIONS

CAS registry No. 929434-83-3, available Apr. 8, 2007.*
CAS registry No. 929418-10-0, available Apr. 9, 2007.*
CAS registry No. 929370-94-5, available Apr. 9, 2007.*
CAS registry No. 573677-31-3, available Aug. 26, 2003.*
CAS registry No. 361188-83-2, available Oct. 9, 2001.*
Gumireadyetal. (PNAS, 2005, 102(6), pp. 1992-1997 and correction 102(15), p. 5635).
Adrian et al., "Allosteric Inhibitors of Bcr-abl-dependent cell proliferation," *Nature Chemical Biology*, 2006, vol. 2, pp. 95-102.
Enamine (supplier, RN 732986-85-5, Aug. 26, 2004), see STN printout, p. 35.
International Preliminary Report on Patentability for Application No. PCT/US2008/013219, dated Jun. 2, 2010.
Supplementary European Search Report for Application No. 08857261.5 dated Dec. 19, 2011.
Examination Report from corresponding EP Application No. EP 19 170 210.9, dated Jun. 17, 2020, 9 pages.
STN (Enamine, entered Aug. 31, 2004, Registry No. 736168-35-7, downloaded Feb. 20, 2016.
Communication dated Oct. 12, 2021 from corresponding European Patent Application EP 21 18 4206.7 and appended Partial European Search Report (total 22 pages).

* cited by examiner

SMALL MOLECULE MYRISTATE INHIBITORS OF Bcr-abl AND METHODS OF USE

RELATED APPLICATIONS

This application is a continuation of U.S. patent application Ser. No. 16/933,095, filed Jul. 20, 2020, which is a divisional of U.S. patent application Ser. No. 16/170,921, filed Oct. 25, 2018, now U.S. Pat. No. 10,787,455, issued Sep. 29, 2020, which is a divisional of U.S. patent application Ser. No. 15/582,004, filed Apr. 28, 2017, now abandoned, which is a continuation of U.S. patent application Ser. No. 14/540,919, filed Nov. 13, 2014, now U.S. Pat. No. 9,670,214, issued Jun. 6, 2017, which is a continuation of U.S. patent application Ser. No. 12/745,496, filed Sep. 1, 2011, now U.S. Pat. No. 8,921,336, issued Dec. 30, 2014, which is a 35 U.S.C. § 371 national stage filing of PCT Application No. PCT/US2008/013219, filed Nov. 28, 2008, which claims priority to and the benefit of U.S. Provisional Application No. 61/004,462, filed Nov. 28, 2007, the entireties of all of which are incorporated herein by reference.

BACKGROUND

The protein kinases represent a large family of proteins, which play a central role in the regulation of a wide variety of cellular processes and maintaining control over cellular function. These kinases include receptor tyrosine kinases, such as platelet-derived growth factor receptor kinase (PDGF-R), the receptor kinase for stem cell factor, c-Kit, and non-receptor tyrosine kinases, such as the fusion kinase Bcr-abl.

Chronic myeloid leukemia (CML) is an extensively studied human cancer that is caused by a reciprocal translocation that fuses the Abl proto-oncogene on chromosome 9 with a gene on chromosome 22 called Bcr. The resulting fusion protein Bcr-abl is capable of transforming B-cells by increasing mitogenic activity, reducing sensitivity to apoptosis and altering the adhesion and homing of CML progenitor cells. STI-571 (Gleevec) is an inhibitor of the oncogenic Bcr-abl tyrosine kinase and is used for the treatment of chronic myeloid leukemia (CML). However, some patients in the blast crisis stage of CML are resistant to STI-571 due to mutations in the Bcr-abl kinase.

The novel compounds of this invention inhibit one or more kinases; in particular wild type and one or more of the mutant forms of Bcr-abl and are, therefore, useful in the treatment of kinase-associated diseases, particularly Bcr-abl kinase associated diseases.

BRIEF SUMMARY OF THE INVENTION

In one aspect, the invention provides a compound of formula I, or pharmaceutically acceptable salt, solvate or hydrate thereof:

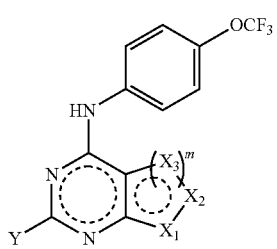

(I)

wherein
each of $X_1$, $X_2$, or $X_3$ is independently $NR_1$, $CR_1$, $C(O)$, O, or S;
each $R_1$ is independently selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $C_{1-6}$aralkyl, an optionally substituted $C_{1-6}$heteroaralkyl, an optionally substituted $C_{1-6}$haloalkyl, an optionally substituted $(CH_2)_n C_{3-12}$heterocycloalkyl, an optionally substituted $(CH_2)_n C_{3-12}$aryl, an optionally substituted $(CH_2)_n C_{3-12}$heteroaryl, an optionally substituted $(CH_2)_n C_{3-12}$cycloalkyl, $C_{1-6}$haloalkyl, $C_{1-6}$aminoalkyl, hal, $(CH_2)_n C(O)R^x$, $(CH_2)_n C(O)OR^x$, $(CH_2)_n C(O)NR^x R^x$, $-(CH_2)_n C(O)NR^x R^x S(O)_2 R^x$; $-C(O)R^x$, $-C(S)R^x$, $-C(NR)R^x$, $-SR^x$, $-S(O)R^x$, $-S(O)_2 R^x$, $-OR^x$, $-NR^x R^x$, nitro, cyano, or absent;
each $R^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl; $NHNHR_2$, or $C(NH)NH_2$;
$R_2$ is H or $C_{1-6}$ alkyl;
Y is H, OH, $NH_2$, or $CH_3$;
m is 1 or 2; and
each n is independently 0, 1 or 2.

In one embodiment, the invention provides a compound of formula II, or pharmaceutically acceptable salt, solvate or hydrate thereof:

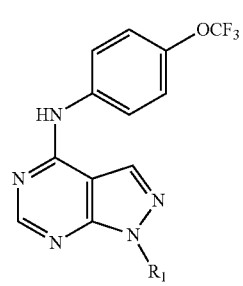

(II)

wherein
$R_1$ is selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $C_{1-6}$aralkyl, an optionally substituted $C_{1-6}$heteroaralkyl, an optionally substituted $C_{1-6}$haloalkyl, an optionally substituted $(CH_2)_n C_{3-12}$heterocycloalkyl, an optionally substituted $(CH_2)_n C_{3-12}$aryl, an optionally substituted $(CH_2)_n C_{3-12}$heteroaryl, an optionally substituted $(CH_2)_n C_{3-12}$cycloalkyl, $(CH_2)_n C(O)R^x$, $(CH_2)_n C(O)OR^x$, $(CH_2)_n C(O)NR^x R^x$, $-C(O)R^x$, $-C(S)R^x$, $-C(NR)R^x$, halo, $C_{1-6}$haloalkyl, $-S(O)R^x$, or $-S(O)_2 R^x$;
$R^x$, for each occurrence, is independently, H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, or $C_{1-6}$haloalkyl; and
each n is independently 0, 1 or 2.

In another embodiment, the invention provides a compound formula III, or pharmaceutically acceptable salt, solvate or hydrate thereof:

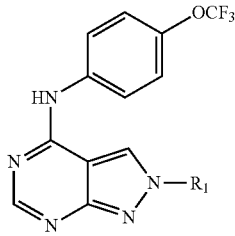

(III)

wherein
R$_1$ is selected from H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, an optionally substituted C$_{1-6}$ aralkyl, an optionally substituted C$_{1-6}$heteroaralkyl, an optionally substituted C$_{1-6}$haloalkyl, an optionally substituted (CH$_2$)$_n$C$_{3-12}$heterocycloalkyl, an optionally substituted (CH$_2$)$_n$C$_{3-12}$aryl, an optionally substituted (CH$_2$)$_n$C$_{3-12}$heteroaryl, an optionally substituted (CH$_2$)$_n$C$_{3-12}$cycloalkyl, (CH$_2$)$_n$C(O)R$^x$, (CH$_2$)$_n$C(O)OR$^x$, (CH$_2$)$_n$C(O)NR$^x$R$^x$, —C(O)R$^x$, —C(S)R$^x$, —C(NR)R$^x$, halo, C$_{1-6}$haloalkyl, —S(O)R$^x$, or —S(O)$_2$R$^x$;

R$^x$, for each occurrence, is independently, H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, or C$_{1-6}$haloalkyl; and each n is independently 0, 1 or 2.

In certain embodiments, the invention provides a compound of formula IV, or pharmaceutically acceptable salt, solvate or hydrate thereof:

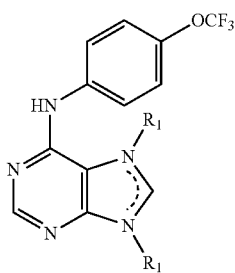

(IV)

wherein
each R$_1$ is independently selected from H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, an optionally substituted C$_{1-6}$ aralkyl, an optionally substituted C$_{1-6}$heteroaralkyl, an optionally substituted C$_{1-6}$haloalkyl, an optionally substituted (CH$_2$)$_n$C$_{3-12}$heterocycloalkyl, an optionally substituted (CH$_2$)$_n$C$_{3-12}$aryl, an optionally substituted (CH$_2$)$_n$C$_{3-12}$heteroaryl, an optionally substituted (CH$_2$)$_n$C$_{3-12}$cycloalkyl, (CH$_2$)$_n$C(O)R$^x$, (CH$_2$)$_n$C(O)OR$^x$, (CH$_2$)$_n$C(O)NR$^x$R$^x$, —C(O)R$^x$, —C(S)R$^x$, —C(NR)R$^x$, halo, C$_{1-6}$haloalkyl, —S(O)R$^x$, —S(O)$_2$R$^x$, or absent;

R$^x$, for each occurrence, is independently, H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, or C$_{1-6}$haloalkyl; and each n is independently 0, 1 or 2.

In another embodiment, the invention provides a compound of formula V, or pharmaceutically acceptable salt, solvate or hydrate thereof:

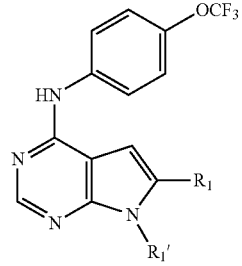

(V)

wherein
R$_1$ is independently selected from H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, an optionally substituted (CH$_2$)$_n$C$_{3-12}$heterocycloalkyl, —C(O)R$^x$, —OR$^x$, —SR$^x$, —NR$^x$R$^x$, nitro, cyano, C$_{1-6}$haloalkyl, C$_{1-6}$ aminoalkyl, (CH$_2$)$_n$C(O)R$^x$, (CH$_2$)$_n$C(O)OR$^x$, (CH$_2$)$_n$C(O)NR$^x$R$^x$, or —(CH$_2$)$_n$C(O)NR$^x$R$^x$S(O)$_2$R$^x$;

R$^x$, for each occurrence, is independently H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, NHNHR$_2$, or C(NH)NH$_2$;

R$_1$' is selected from H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, an optionally substituted C$_{1-6}$aralkyl, an optionally substituted C$_{1-6}$heteroaralkyl, an optionally substituted C$_{1-6}$haloalkyl, an optionally substituted (CH$_2$)$_n$C$_{3-12}$heterocycloalkyl, an optionally substituted (CH$_2$)$_n$C$_{3-12}$aryl, an optionally substituted (CH$_2$)$_n$C$_{3-12}$heteroaryl, an optionally substituted (CH$_2$)$_n$C$_{3-12}$cycloalkyl, (CH$_2$)$_n$C(O)R$^y$, (CH$_2$)$_n$C(O)OR$^y$, (CH$_2$)$_n$C(O)NR$^y$R$^y$, —C(O)R$^y$, —C(S)R$^y$, —C(NR)R$^y$, halo, C$_{1-6}$haloalkyl, —S(O)R$^y$, or —S(O)$_2$R$^y$;

R$^y$, for each occurrence, is independently, H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, or C$_{1-6}$haloalkyl;

each n is independently 0, 1 or 2; and

R$_2$ is H or C$_{1-4}$ alkyl.

In a further embodiment, R$_1$ is independently selected from H, an optionally substituted C$_{1-6}$alkyl, an optionally substituted C$_{3-12}$cycloalkyl, an optionally substituted C$_{3-12}$heterocycloalkyl, an optionally substituted C$_{3-12}$aryl, an optionally substituted C$_{3-12}$heteroaryl, an optionally substituted $(CH_2)_nC_{3-12}$heterocycloalkyl, —C(O)R$^x$, —OR$^x$, —SR$^x$, —NR$^x$R$^x$, nitro, cyano, $C_{1-6}$haloalkyl, $C_{1-6}$aminoalkyl, $(CH_2)_nC(O)R^x$, $(CH_2)_nC(O)OR^x$, $(CH_2)_nC(O)NR^xR^x$, or —$(CH_2)_nC(O)NR^xR^xS(O)_2R^x$;

R$^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, NHNHR$_2$, or C(NH)NH$_2$; and R$_2$ is H or $C_{1-4}$ alkyl.

In another further embodiment, R$_1$' is selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $C_{1-6}$aralkyl, an optionally substituted $C_{1-6}$heteroaralkyl, an optionally substituted $C_{1-6}$ haloalkyl, an optionally substituted $(CH_2)_nC_{3-12}$heterocycloalkyl, an optionally substituted $(CH_2)_nC_{3-12}$aryl, an optionally substituted $(CH_2)_nC_{3-12}$heteroaryl, an optionally substituted $(CH_2)_nC_{3-12}$cycloalkyl, $(CH_2)_nC(O)R^y$, $(CH_2)_nC(O)OR^y$, $(CH_2)_nC(O)NR^yR^y$, —C(O)R$^y$, —C(S)R$^y$, —C(NR)R$^y$, halo, $C_{1-6}$haloalkyl, —S(O)R$^y$, or —S(O)$_2$R$^y$;

R$^y$, for each occurrence, is independently, H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, or $C_{1-6}$haloalkyl;

In other embodiments, the invention provides a compound of formula VI, or pharmaceutically acceptable salt, solvate or hydrate thereof:

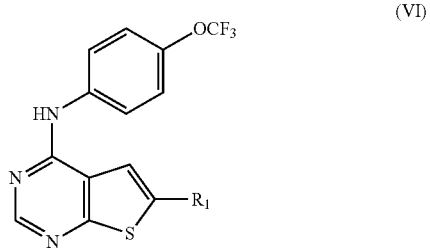

(VI)

wherein
R$_1$ is independently selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $(CH_2)_nC_{3-12}$heterocycloalkyl, —C(O)R$^x$, —OR$^x$, —SR$^x$, —NR$^x$R$^x$, nitro, cyano, $C_{1-6}$haloalkyl, $C_{1-6}$aminoalkyl, $(CH_2)_nC(O)R^x$, $(CH_2)_nC(O)OR^x$, $(CH_2)_nC(O)NR^xR^x$, or —$(CH_2)_nC(O)NR^xR^xS(O)_2R^x$;

R$^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, NHNHR$_2$, C(NH)NH$_2$;

R$_2$ is H or $C_{1-4}$ alkyl; and

Each n is independently 0, 1, or 2.

In still another embodiment, the invention provides a compound of formula VII, or pharmaceutically acceptable salt, solvate or hydrate thereof:

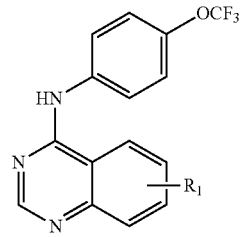

(VII)

wherein
R$_1$ is selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $(CH_2)_nC_{3-12}$heterocycloalkyl, —C(O)R$^x$, —OR$^x$, —SR$^x$, —NR$^x$R$^x$, nitro, cyano, $C_{1-6}$haloalkyl, $C_{1-6}$aminoalkyl, $(CH_2)_nC(O)R^x$, $(CH_2)_nC(O)OR^x$, $(CH_2)_nC(O)NR^xR^x$, or —$(CH_2)_nC(O)NR^xR^xS(O)_2R^x$;

R$^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, NHNHR$_2$, or C(NH)NH$_2$;

R$_2$ is H or $C_{1-4}$ alkyl;
m is 1 or 2; and
each n is independently 0, 1 or 2.

In another embodiment, the invention provides a compound of formula VIII, or pharmaceutically acceptable salt, solvate or hydrate thereof:

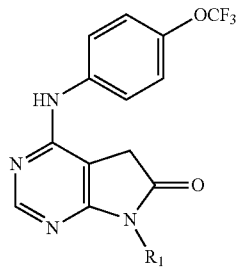

(VIII)

wherein
R$_1$ is selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $C_{1-6}$aralkyl, an optionally substituted $C_{1-6}$heteroaralkyl, an optionally substituted $C_{1-6}$haloalkyl, an optionally substituted $(CH_2)_nC_{3-12}$heterocycloalkyl, an optionally substituted $(CH_2)_nC_{3-12}$aryl, an optionally substituted $(CH_2)_nC_{3-12}$heteroaryl, an optionally substituted $(CH_2)_nC_{3-12}$cycloalkyl, $(CH_2)_nC(O)R^x$, $(CH_2)_nC(O)OR^x$, $(CH_2)_nC(O)NR^xR^x$, —C(O)R$^x$, —C(S)R$^x$, —C(NR)R$^x$, halo, $C_{1-6}$haloalkyl, —S(O)R$^x$, or —S(O)$_2$R$^x$;

R$^x$, for each occurrence, is independently, H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, or $C_{1-6}$haloalkyl; and each n is independently 0, 1 or 2.

In another aspect, the invention provides a compound of formula IX, or pharmaceutically acceptable salt, solvate or hydrate thereof:

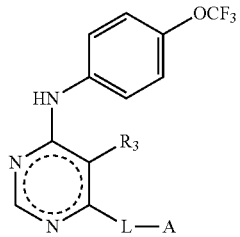

wherein
- $R_3$ is H or $C_{1-4}$ alkyl;
- L is $NR_3$, O, S, S(O), S(O)$_2$, C(O), C(S), C(NR), C(NR$^x$)NR$^x$, C(O)NR$^x$, C(O)NR$^x$NR$^x$, C(O)ONR$^x$, C(O)NR$^x$O, C(O)O, OC(O), OC(O)O, or a bond;
- each $R^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl; NHNHR$_2$, or C(NH)NH$_2$;
- A is an optionally substituted $C_{1-6}$alkyl, an optionally substituted $C_{3-12}$aryl, an optionally substituted $C_{3-12}$heteroaryl, an optionally substituted $C_{3-12}$cycloalkyl, or an optionally substituted $C_{3-12}$heterocycloalkyl.

In one embodiment, A is an optionally substituted $C_{1-6}$alkyl, an optionally substituted $C_{3-12}$aryl, an optionally substituted $C_{3-12}$heteroaryl, or an optionally substituted $C_{3-12}$heterocycloalkyl.

In a further embodiment, A is an optionally substituted phenyl ring, an optionally substituted naphthyl ring, an optionally substituted piperidine ring, an optionally substituted imidazole ring, an optionally substituted pyrazole ring, an optionally substituted 1H-pyrazole ring, an optionally substituted 1H-Pyrrolo[2,3-b]pyridine ring, an optionally substituted pyrimidine ring, an optionally substituted pyrazine ring, an optionally substituted pyridine ring, an optionally substituted indole ring, an optionally substituted 1H-indole ring, an optionally substituted furan ring, an optionally substituted benzo[b]thiophene ring, an optionally substituted dibenzofuran ring, an optionally substituted 1H-Pyridin-2-one ring, an optionally substituted thiazole ring, or an ethyl group.

In another further embodiment, A is optionally substituted with $C_{1-6}$alkyl, $C_{2-6}$alkenyl, $C_{2-6}$alkynyl, $C_{3-12}$cycloalkyl, $C_{3-12}$heterocycloalkyl, $C_{3-14}$aralkyl, $C_{3-14}$heteroaralkyl, $C_{3-12}$aryl, $(CH_2)_pC_{3-12}$aryl, $C_{3-12}$heteroaryl, $(CH_2)_pC_{3-12}$heteroaryl, halogen, haloalkyl, cyano, $(CH_2)_p$CN, nitro, $C_{1-6}$alkoxy, $C_{3-12}$aryloxy, $C_1$-$C_4$ haloalkoxy, $C_1$-$C_6$ haloalkyl, hydroxyl, $C_{1-6}$hydroxylalkyl, $C_{1-6}$carboxyl, CHO, amino, aminoalkyl, dialkylamino, OR$^{15}$, SR$^{15}$, NR$^{17}$R$^{17}$C(O)OR$^{15}$, C(O)NR$^{15}$R$^{16}$, OC(O)NR$^{15}$R$^{16}$, NR$^{15}$C(O)NR$^{15}$R$^{16}$, NR$^{17}$S(O)$_2$R$^{15}$, NR$^{17}$(CH$_2$)$_n$R$^{17}$, C(O)R$^{17}$, C(O)NR$^{17}$R$^{17}$, NR$^{15}$C(O)R$^{17}$, S(O)R$^{17}$, S(O)$_2$R$^{17}$, or S(O)$_2$NR$^{17}$R$^{17}$;
- each $R^{15}$ is independently hydrogen, $C_{3-14}$ aralkyl, $C_{1-6}$ alkyl, $C_{3-12}$ cycloalkyl, $C_{3-12}$ aryl, $C_{3-12}$ heterocycloalkyl, or $C_{3-12}$ heteroaryl;
- each $R^{16}$ is independently hydrogen, $C_{3-14}$ aralkyl, or $C_{1-6}$ alkyl;
- each $R^{17}$ is independently H, $C_{1-6}$ alkyl, $C_{1-6}$ hydroxyalkyl, $C_{1-6}$ alkoxy, $C_{3-12}$ cycloalkyl, $C_{3-12}$aryl, $C_{3-12}$heteroaryl, $C_{3-12}$heterocycloalkyl, hydroxyl, or each $R^{17}$ may form a heterocycloalkyl ring with another $R^{17}$;
- wherein each A, $R^{15}$, $R^{16}$, and $R^{17}$ may be further optionally substituted with $C_{1-6}$ alkyl, $C_{1-6}$ alkoxy, $C_{1-6}$ haloalkoxy, $C_{3-12}$heterocycloalkyl, amino, halogen, $C_{1-6}$ haloalkyl, SO$_2$alkyl, or NHC(O)aryl; and
- each p is independently 0-6.

In another aspect, the invention provides a compound of formula X, or pharmaceutically acceptable salt, solvate or hydrate thereof:

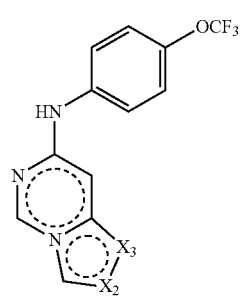

wherein
- each of $X_2$ or $X_3$ is independently NR$_1$, CR$_1$, C(O), O, or S;
- each $R_1$ is independently selected from H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, an optionally substituted $C_{2-6}$aralkyl, an optionally substituted $C_{2-12}$heteroaralkyl, an optionally substituted $C_{1-6}$haloalkyl, an optionally substituted $(CH_2)_nC_{3-12}$aryl, an optionally substituted $(CH_2)_nC_{3-12}$heteroaryl, an optionally substituted $(CH_2)_nC_{3-12}$cycloalkyl, an optionally substituted $(CH_2)_nC_{3-12}$heterocycloalkyl, $C_{1-6}$haloalkyl, $C_{1-6}$aminoalkyl, hal, $(CH_2)_nC(O)R^x$, $(CH_2)_nC(O)OR^x$, $(CH_2)_nC(O)NR^xR^x$, —$(CH_2)_nC(O)NR^xR^xS(O)_2R^x$; —C(O)R$^x$, —C(S)R$^x$, —C(NR)R$^x$, —SR$^x$, —S(O)R$^x$, —S(O)$_2$R$^x$, —OR$^x$, —NR$^xR^x$, nitro, cyano, or absent;
- each $R^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, $C_{1-6}$haloalkyl; NHNHR$_2$, or C(NH)NH$_2$;
- $R_2$ is H or $C_{1-6}$ alkyl; and
- each n is independently 0, 1 or 2.

In one embodiment, the invention provides a compound of formula XI, or pharmaceutically acceptable salt, solvate or hydrate thereof:

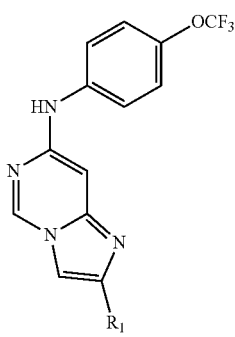

(XI)

wherein
R₁ is independently selected from H, an optionally substituted $C_{1-6}$alkyl, an optionally substituted $C_{3-12}$aryl, or an optionally substituted $C_{3-12}$heteroaryl.

In certain aspects, the present invention is directed towards a method of treating a disease in a subject in which inhibition of kinase activity, particularly Bcr-abl activity, can prevent, inhibit or ameliorate the pathology and/or symptomology of certain disorders and/or diseases, which method comprises administering to the subject a therapeutically effective amount of a compound of the invention or pharmaceutically acceptable salt, solvate or hydrate thereof.

In one aspect, the invention provides a method of treating a kinase activity related disorder in a subject, comprising administering to said subject in need thereof, an effective amount of a compound, or pharmaceutically acceptable salt, solvate or hydrate thereof, of any one of the compounds disclosed herein.

In certain embodiments, the compound is a kinase inhibitor. In a further embodiment, the compound interacts with Bcr-abl. In another further embodiment, the compound targets the binding site of Bcr-abl.

In another embodiment, the subject is identified as being in need of kinase inhibition, and the compound of the invention is administered to the identified subject.

In still another embodiment, the invention provides the method further comprising the step of identifying a subject in need of such treatment for a kinase activity related disorder and administering the compound to the identified subject.

In other embodiments, the invention provides a method wherein the subject is suffering from a cell proliferative disorder or disease. In a further embodiment, the disorder is cancer, tumor, neoplasm, neovascularization, vascularization, cardiovascular disease, metastasis, infection, blood clot, atherosclerosis, melanoma, skin disorder, rheumatoid arthritis, diabetic retinopathy, macular edema, or macular degeneration, inflammatory and arthritic disease, or osteosarcoma. In a further embodiment, the subject is suffering from a solid tumor or disseminated cancer. In another further embodiment, the cancer is leukemia, multiple myeloma or lymphoma. In certain embodiments, the leukemia is Chroic Myelogenous Leukemia.

In another aspect, the invention provides a method of treating cancer in a subject, the method comprising administering to said subject an effective amount of a compound, or pharmaceutically acceptable salt, solvate or hydrate thereof, of any of the compounds disclosed herein.

In one embodiment, the invention provides a method described above further comprising administering an additional therapeutic agent. In a further embodiment, the additional therapeutic agent is an ATP-site inhibitor. In another further embodiment, the ATP-site inhibitor is selected from the following: imatinib (STI571), Nilotinib (AMN107), Dasatinib (BMS-354825), AP234464 (Ariad Pharmaceuticals), AZD0530 (Astrazeneca), and SKI-606 (Wyeth).

In another embodiment, the subject is a mammal. In a further embodiment, the subject is a primate or human.

In one embodiment, the invention provides a method wherein the step of administering the compound comprises administering the compound orally, topically, parentally, intravenously or intramuscularly. In a further embodiment, the method comprises the step of administering an effective amount of a composition comprising the compound and a pharmaceutically suitable excipient.

In certain embodiments, the step of administering the compound comprises administering the compound in a dosage of between about 0.01 μg/kg/day and 100 mg/kg/day.

In another aspect, the invention provides a method of inhibiting kinase activity in a subject, the method comprising the step of administering to the subject a compound, or pharmaceutically acceptable salt, solvate or hydrate thereof, of any one of the compounds disclosed herein.

In other aspects, the invention provides the use of a compound described herein in the manufacture of a medicament for treating a disease in a subject in which kinase activity, particularly Bcr-abl activity, contributes to the pathology and/or symptomology of the disease.

In other aspects, the invention provides a pharmaceutical composition comprising a compound, or pharmaceutically acceptable salt, solvate or hydrate thereof, of any of the compounds disclosed herein. In one embodiment, the invention provides a composition further comprising an additional therapeutic agent. In another embodiment, the additional therapeutic agent is an ATP-site inhibitor. In another further embodiment, the ATP-site inhibitor is selected from the following: imatinib (STI571), Nilotinib (AMN107), Dasatinib (BMS-354825), AP234464 (Ariad Pharmaceuticals), AZD0530 (Astrazeneca), and SKI-606 (Wyeth).

In certain aspects, the invention provides a kit comprising an effective amount of a compound disclosed herein, or pharmaceutically acceptable salt, solvate or hydrate thereof, in unit dosage form, together with instructions for administering the compound to a subject suffering from or susceptible to a cell proliferative disorder.

In certain aspects, the present invention provides a method for inhibiting Bcr-abl activity, the method comprising contacting Bcr-abl with a compound of the invention that binds to a myristoyl binding pocket of Bcr-abl.

In one aspect, the invention provides for a method for identifying a compound which modulates the kinase activity of Bcr-abl, the method comprising:
a) contacting Bcr-abl with a compound under conditions suitable for modulation of the kinase activity of Bcr-abl; and
b) detecting modulation of the kinase activity of Bcr-abl by the compound; wherein the compound is capable of interacting with the myristate binding site of Bcr-abl.

In one embodiment, the interaction of the compound with myristate binding site of Bcr-abl is a binding interaction. In another embodiment, the binding interaction is ionic, covalent, or a non-direct interaction. In still another embodiment, the compound has a binding interaction with Ala452, Tyr454, Glu481, Pro484, Val487, Phe516, Ile521, or Val525 (Number based upon crystal structure with protein databank code: 1OPL, reference: Nagar, B., Hantschel, O., Young, M. A., Scheffzek, K., Veach, D., Bornmann, W., Clarkson, B., Superti-Furga, G., Kuriyan, J. Structural basis for the autoinhibition of c-Abl tyrosine kinase Cell (Cambridge, Mass.) v112 pp. 859-871, 2003.

In other embodiments, the modulation of the activity of the kinase activity is detected by direct binding of the compound to the myristate binding site of Bcr-abl.

In another embodiment, the compound is designed de novo.

In other embodiments, the compound is designed from a known ligand of the myristate binding site of Bcr-abl.

DETAILED DESCRIPTION

Compounds of the Invention

Exemplary compounds of the invention include the following, which are provided structurally in Tables 1-9.
2-(4-(4-(trifluoromethoxy)phenylamino)-1H-pyrazolo[3,4-d]pyrimidin-1-yl)ethanol (1);
(1H-Pyrazolo[3,4-d]pyrimidin-4-yl)-(4-trifluoromethoxy-phenyl)-amine (2);
(1-Ethyl-1H-pyrazolo[3,4-d]pyrimidin-4-yl)-(4-trifluoromethoxy-phenyl)-amine (3);
(1-Ethanesulfonyl-1H-pyrazolo[3,4-d]pyrimidin-4-yl)-(4-trifluoromethoxy-phenyl)-amine (4);
(1-Cyclohexyl-1H-pyrazolo[3,4-d]pyrimidin-4-yl)-(4-trifluoromethoxy-phenyl)-amine (5);
2-[4-(4-Trifluoromethoxy-phenylamino)-pyrazolo[3,4-d]pyrimidin-1-yl]-ethanol (6);
2-[4-(4-Trifluoromethoxy-phenylamino)-pyrazolo[3,4-d]pyrimidin-1-yl]-acetamide (7);
3-[4-(4-Trifluoromethoxy-phenylamino)-pyrazolo[3,4-d]pyrimidin-1-yl]-propionamide (8);
[1-(Tetrahydro-furan-3-ylmethyl)-1H-pyrazolo[3,4-d]pyrimidin-4-yl]-(4-trifluoromethoxy-phenyl)-amine (9);
3-Dimethylamino-2-[4-(4-trifluoromethoxy-phenylamino)-pyrazolo[3,4-d]pyrimidin-1-yl]-propionitrile (10);
(1-Butyl-1H-pyrazolo[3,4-d]pyrimidin-4-yl)-(4-trifluoromethoxy-phenyl)-amine (11);
(1-tert-Butyl-1H-pyrazolo[3,4-d]pyrimidin-4-yl)-(4-trifluoromethoxy-phenyl)-amine (12);
[1-(2,2,2-Trifluoro-ethyl)-1H-pyrazolo[3,4-d]pyrimidin-4-yl]-(4-trifluoromethoxy-phenyl)-amine (13);
(1-Benzyl-1H-pyrazolo[3,4-d]pyrimidin-4-yl)-(4-trifluoromethoxy-phenyl)-amine (14);
(1-Phenethyl-1H-pyrazolo[3,4-d]pyrimidin-4-yl)-(4-trifluoromethoxy-phenyl)-amine (15);
[1-(3-Fluoro-4-trifluoromethyl-benzyl)-1H-pyrazolo[3,4-d]pyrimidin-4-yl]-(4-trifluoromethoxy-phenyl)-amine (16);
[1-(3-Bromo-benzyl)-1H-pyrazolo[3,4-d]pyrimidin-4-yl]-(4-trifluoromethoxy-phenyl)-amine (17);
3-[4-(4-Trifluoromethoxy-phenylamino)-pyrazolo[3,4-d]pyrimidin-1-ylmethyl]-phenol (18);
(1-Pyridin-3-ylmethyl-1H-pyrazolo[3,4-d]pyrimidin-4-yl)-(4-trifluoromethoxy-phenyl)-amine (19);
(1-Pyridin-2-ylmethyl-1H-pyrazolo[3,4-d]pyrimidin-4-yl)-(4-trifluoromethoxy-phenyl)-amine (20);
(1-Pyridin-4-ylmethyl-1H-pyrazolo[3,4-d]pyrimidin-4-yl)-(4-trifluoromethoxy-phenyl)-amine (21);
2-{2-[4-(4-Trifluoromethoxy-phenylamino)-pyrazolo[3,4-d]pyrimidin-1-yl]-ethyl}-isoindole-1,3-dione (22);
[1-(2-Amino-ethyl)-1H-pyrazolo[3,4-d]pyrimidin-4-yl]-(4-trifluoromethoxy-phenyl)-amine (23);
(4-Trifluoromethoxy-phenyl)-[1-(4-trifluoro methyl-pyridin-2-yl)-1H-pyrazolo[3,4-d]pyrimidin-4-yl]-amine (24);
[1-(2,3-Dimethyl-phenyl)-1H-pyrazolo[3,4-d]pyrimidin-4-yl]-(4-trifluoromethoxy-phenyl)-amine (25);
[1-(2-Fluoro-phenyl)-1H-pyrazolo[3,4-d]pyrimidin-4-yl]-(4-trifluoromethoxy-phenyl)-amine (26);
[1-(2,4-Dichloro-phenyl)-1H-pyrazolo[3,4-d]pyrimidin-4-yl]-(4-trifluoromethoxy-phenyl)-amine (27);
[1-(2-Ethyl-phenyl)-1H-pyrazolo[3,4-d]pyrimidin-4-yl]-(4-trifluoromethoxy-phenyl)-amine (28);
(1-Pyridin-2-yl-1H-pyrazolo[3,4-d]pyrimidin-4-yl)-(4-trifluoromethoxy-phenyl)-amine (29);
3-[4-(4-Trifluoromethoxy-phenylamino)-pyrazolo[3,4-d]pyrimidin-1-yl]-benzenesulfonamide (30);

TABLE 1

Compounds of formula II.

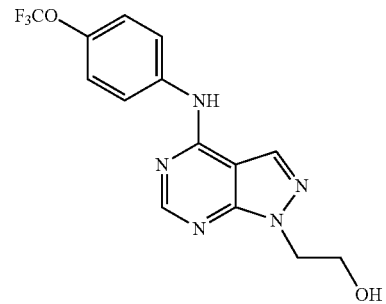 [SMILES: OCCn1ncc2c(Nc3ccc(OC(F)(F)F)cc3)ncnc21]

(1)

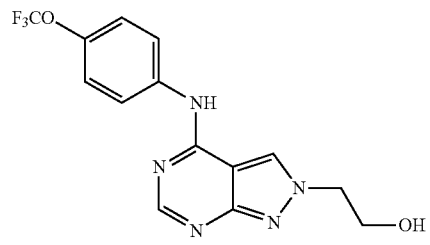 [SMILES: OCCn1cc2c(Nc3ccc(OC(F)(F)F)cc3)ncnc2n1]

(2)

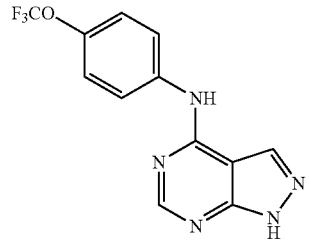 [SMILES: FC(F)(F)Oc1ccc(Nc2ncnc3[nH]ncc23)cc1]

(3)

TABLE 1-continued
Compounds of formula II.
(4)
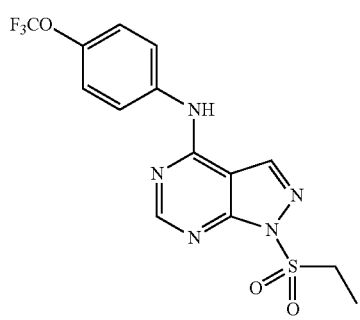 [SMILES: CCS(=O)(=O)n1ncc2c(Nc3ccc(OC(F)(F)F)cc3)ncnc21]
(5)
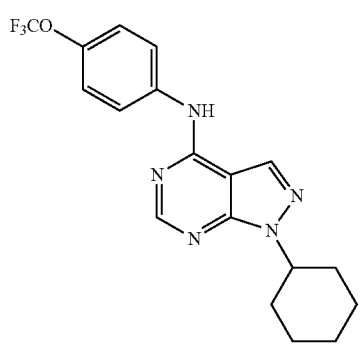 [SMILES: FC(F)(F)Oc1ccc(Nc2ncnc3c2cnn3C2CCCCC2)cc1]
(6)
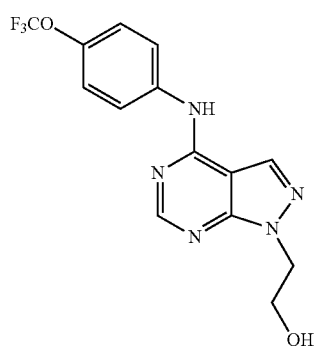 [SMILES: OCCn1ncc2c(Nc3ccc(OC(F)(F)F)cc3)ncnc21]
(7)
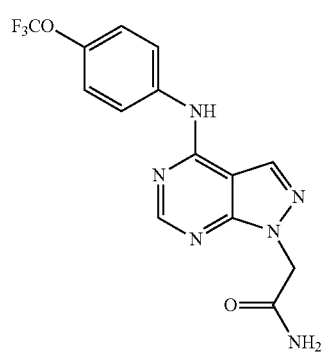 [SMILES: NC(=O)Cn1ncc2c(Nc3ccc(OC(F)(F)F)cc3)ncnc21]
TABLE 1-continued
Compounds of formula II.
(8)
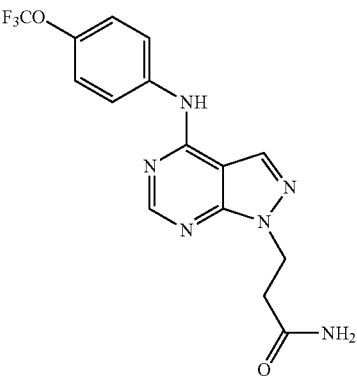 [SMILES: NC(=O)CCn1ncc2c(Nc3ccc(OC(F)(F)F)cc3)ncnc21]
(9)
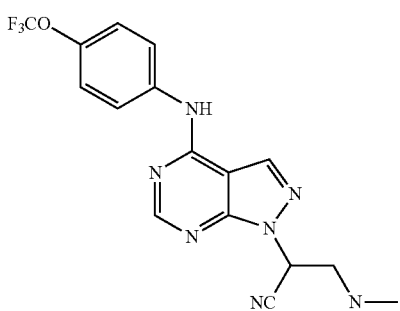
(10)
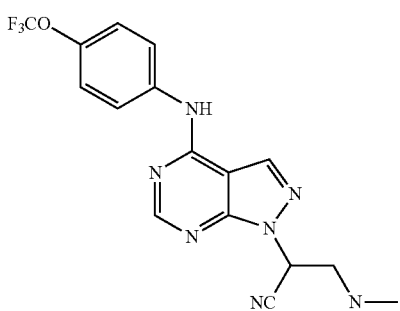
(11)
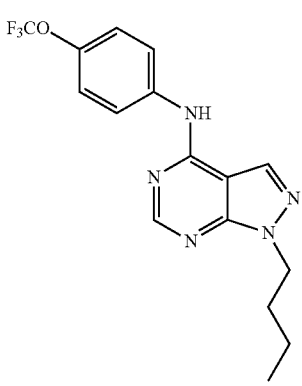 [SMILES: CCCCn1ncc2c(Nc3ccc(OC(F)(F)F)cc3)ncnc21]

TABLE 1-continued
Compounds of formula II.
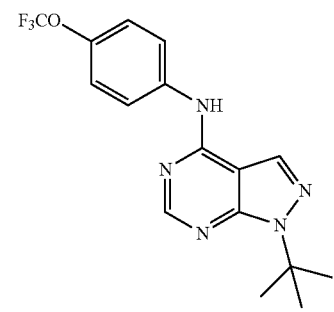 [SMILES: CC(C)(C)n1ncc2c(Nc3ccc(OC(F)(F)F)cc3)ncnc21]
(12)
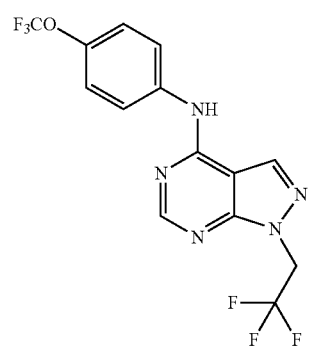 [SMILES: FC(F)(F)Cn1ncc2c(Nc3ccc(OC(F)(F)F)cc3)ncnc21]
(13)
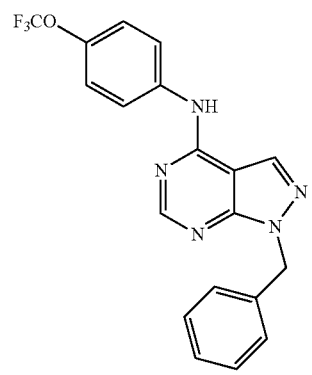 [SMILES: FC(F)(F)Oc1ccc(Nc2ncnc3c2cnn3Cc2ccccc2)cc1]
(14)
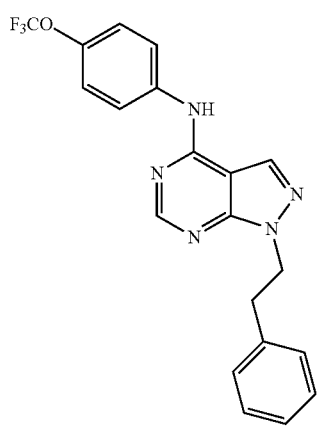 [SMILES: FC(F)(F)Oc1ccc(Nc2ncnc3c2cnn3CCc2ccccc2)cc1]
(15)
TABLE 1-continued
Compounds of formula II.
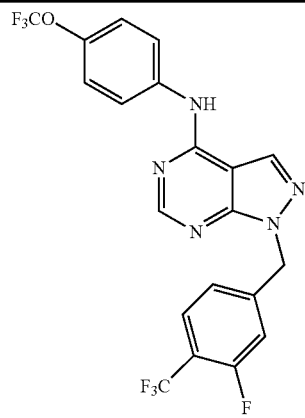
(16)
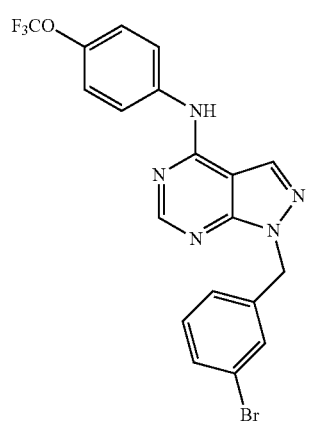 [SMILES: FC(F)(F)Oc1ccc(Nc2ncnc3c2cnn3Cc2cccc(Br)c2)cc1]
(17)
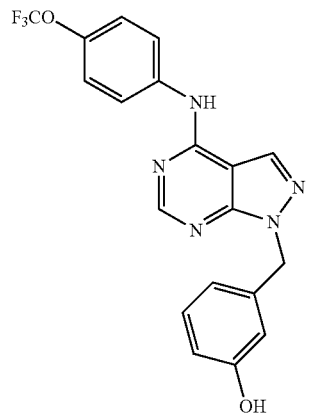 [SMILES: Oc1cccc(Cn2ncc3c(Nc4ccc(OC(F)(F)F)cc4)ncnc32)c1]
(18)
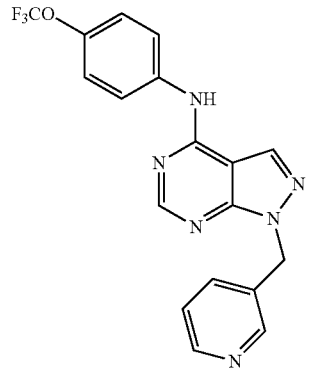 [SMILES: FC(F)(F)Oc1ccc(Nc2ncnc3c2cnn3Cc2cccnc2)cc1]
(19)

TABLE 1-continued
Compounds of formula II.
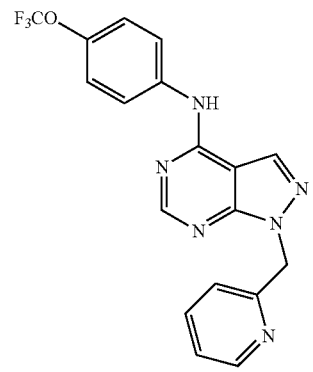 [SMILES: FC(F)(F)Oc1ccc(Nc2ncnc3c2cnn3Cc2ccccn2)cc1] (20)
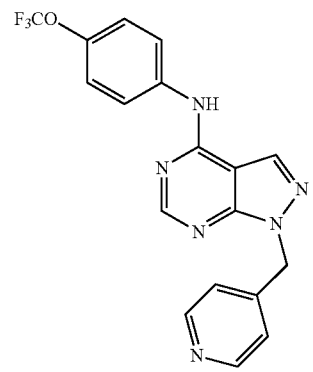 (21)
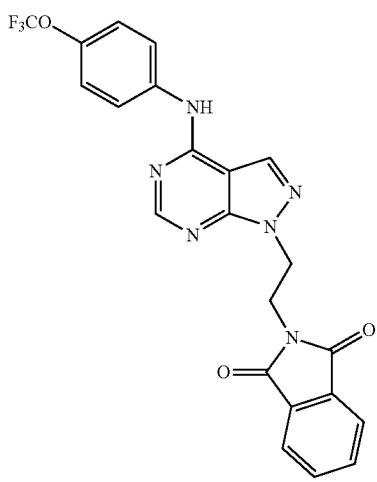 [SMILES: O=C1c2ccccc2C(=O)N1CCn1ncc2c(Nc3ccc(OC(F)(F)F)cc3)ncnc21] (22)
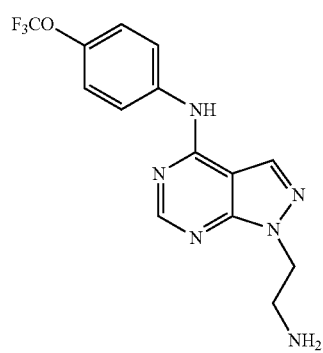 [SMILES: NCCn1ncc2c(Nc3ccc(OC(F)(F)F)cc3)ncnc21] (23)
TABLE 1-continued
Compounds of formula II.
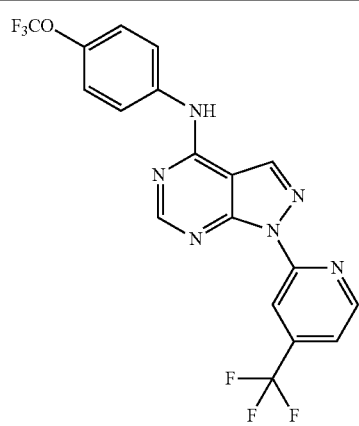 (24)
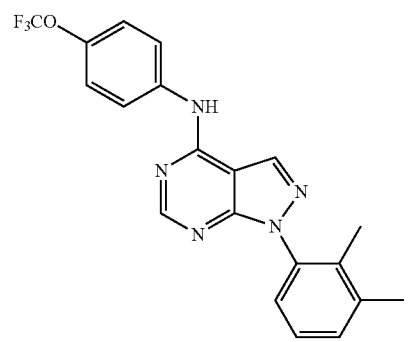 [SMILES: Cc1cccc(-n2ncc3c(Nc4ccc(OC(F)(F)F)cc4)ncnc32)c1C] (25)
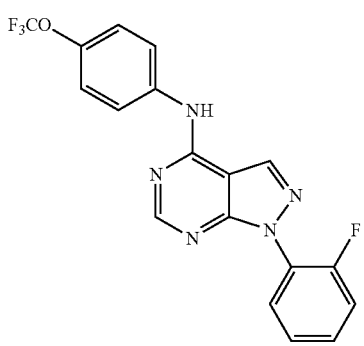 [SMILES: Fc1ccccc1-n1ncc2c(Nc3ccc(OC(F)(F)F)cc3)ncnc21] (26)
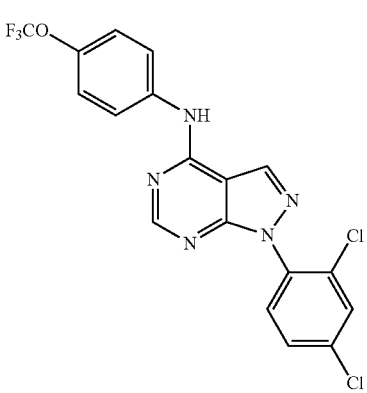 [SMILES: FC(F)(F)Oc1ccc(Nc2ncnc3c2cnn3-c2ccc(Cl)cc2Cl)cc1] (27)

TABLE 1-continued

Compounds of formula II.

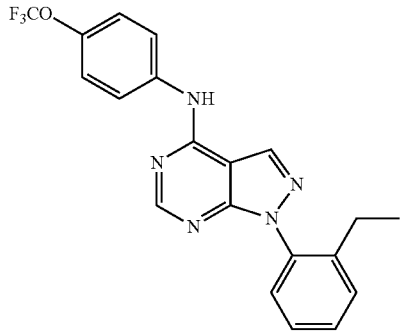 [SMILES: CCc1ccccc1-n1ncc2c(Nc3ccc(OC(F)(F)F)cc3)ncnc21]
(28)

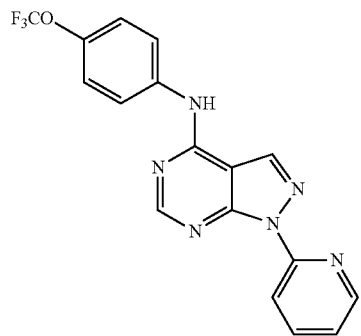 [SMILES: FC(F)(F)Oc1ccc(Nc2ncnc3c2cnn3-c2ccccn2)cc1]
(29)

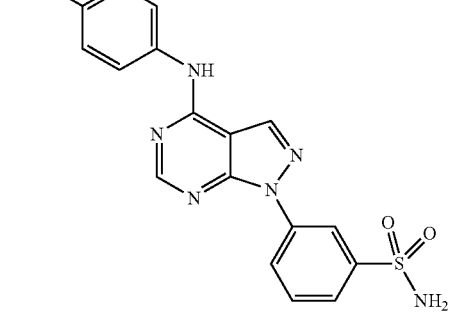
(30)

2-(4-(4-(trifluoromethoxy)phenylamino)-2H-pyrazolo[3,4-d]pyrimidin-2-yl)ethanol (31);
(2-Ethyl-2H-pyrazolo[3,4-d]pyrimidin-4-yl)-(4-trifluoromethoxy-phenyl)-amine (32);
(2-Cyclohexyl-2H-pyrazolo[3,4-d]pyrimidin-4-yl)-(4-trifluoromethoxy-phenyl)-amine (33);
2-[4-(4-Trifluoromethoxy-phenylamino)-pyrazolo[3,4-d]pyrimidin-2-yl]-ethanol (34);
2-[4-(4-Trifluoromethoxy-phenylamino)-pyrazolo[3,4-d]pyrimidin-2-yl]-acetamide (35);
[2-(Tetrahydro-furan-3-ylmethyl)-2H-pyrazolo[3,4-d]pyrimidin-4-yl]-(4-trifluoromethoxy-phenyl)-amine (36);
(2-Butyl-2H-pyrazolo[3,4-d]pyrimidin-4-yl)-(4-trifluoromethoxy-phenyl)-amine (37);
[2-(2,2,2-Trifluoro-ethyl)-2H-pyrazolo[3,4-d]pyrimidin-4-yl]-(4-trifluoromethoxy-phenyl)-amine (38);
(2-Benzyl-2H-pyrazolo[3,4-d]pyrimidin-4-yl)-(4-trifluoromethoxy-phenyl)-amine (39);
(2-Phenethyl-2H-pyrazolo[3,4-d]pyrimidin-4-yl)-(4-trifluoromethoxy-phenyl)-amine (40);
[2-(3-Fluoro-4-trifluoromethyl-benzyl)-2H-pyrazolo[3,4-d]pyrimidin-4-yl]-(4-trifluoromethoxy-phenyl)-amine (41);
[2-(3-Bromo-benzyl)-2H-pyrazolo[3,4-d]pyrimidin-4-yl]-(4-trifluoromethoxy-phenyl)-amine (42);
3-[4-(4-Trifluoromethoxy-phenylamino)-pyrazolo[3,4-d]pyrimidin-2-ylmethyl]-phenol (43);
(2-Pyridin-3-ylmethyl-2H-pyrazolo[3,4-d]pyrimidin-4-yl)-(4-trifluoromethoxy-phenyl)-amine (44);
(4-Trifluoromethoxy-phenyl)-[2-(4-trifluoromethyl-pyridin-2-yl)-2H-pyrazolo[3,4-d]pyrimidin-4-yl]-amine (45);
[2-(2,3-Dimethyl-phenyl)-2H-pyrazolo[3,4-d]pyrimidin-4-yl]-(4-trifluoromethoxy-phenyl)-amine (46);
[2-(2-Fluoro-phenyl)-2H-pyrazolo[3,4-d]pyrimidin-4-yl]-(4-trifluoromethoxy-phenyl)-amine (47);
[2-(2,4-Dichloro-phenyl)-2H-pyrazolo[3,4-d]pyrimidin-4-yl]-(4-trifluoromethoxy-phenyl)-amine (48);
[2-(2-Ethyl-phenyl)-2H-pyrazolo[3,4-d]pyrimidin-4-yl]-(4-trifluoromethoxy-phenyl)-amine (49);
(2-Pyridin-2-yl-2H-pyrazolo[3,4-d]pyrimidin-4-yl)-(4-trifluoromethoxy-phenyl)-amine (50);

TABLE 2

Compounds of formula III.

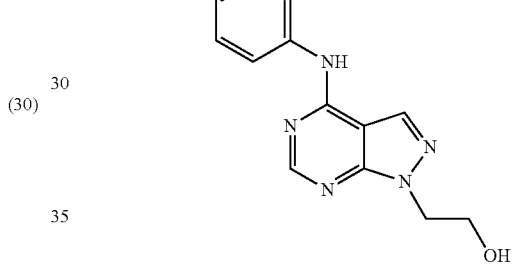
(31)

(32)

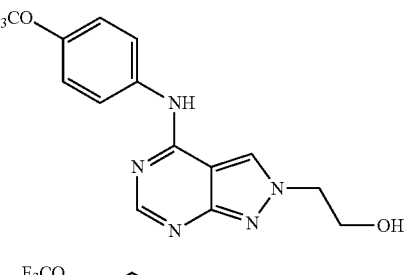
(33)

TABLE 2-continued
Compounds of formula III.
(34) 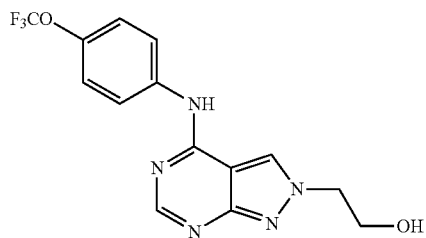 [SMILES: OCCn1cc2c(Nc3ccc(OC(F)(F)F)cc3)ncnc2n1]
(35) 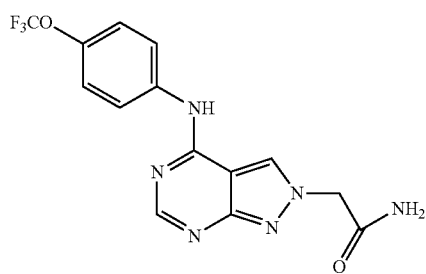 [SMILES: NC(=O)Cn1cc2c(Nc3ccc(OC(F)(F)F)cc3)ncnc2n1]
(36) 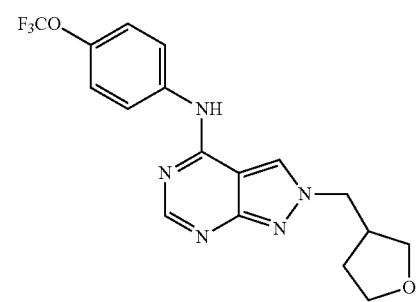 [SMILES: FC(F)(F)Oc1ccc(Nc2ncnc3nn(CC4CCOC4)cc23)cc1]
(37) 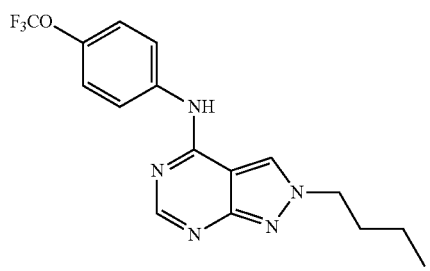 [SMILES: CCCCn1cc2c(Nc3ccc(OC(F)(F)F)cc3)ncnc2n1]
(38) 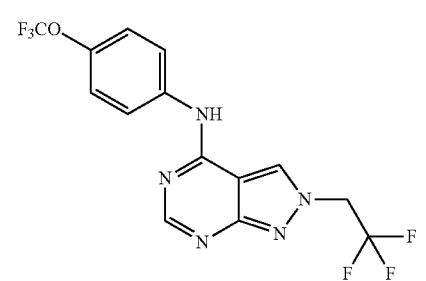 [SMILES: FC(F)(F)Cn1cc2c(Nc3ccc(OC(F)(F)F)cc3)ncnc2n1]
(39) 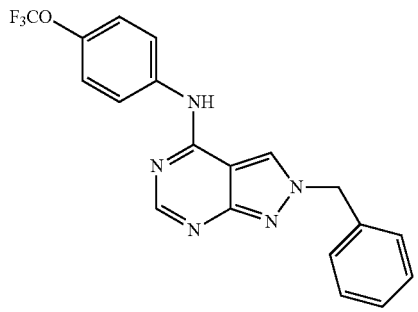 [SMILES: FC(F)(F)Oc1ccc(Nc2ncnc3nn(Cc4ccccc4)cc23)cc1]
(40) 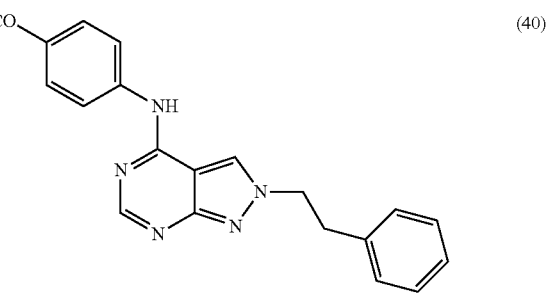
(41) 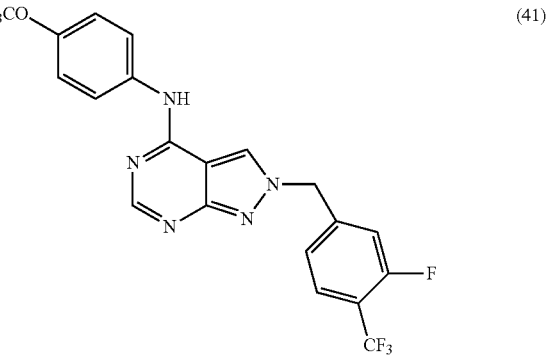
(42) 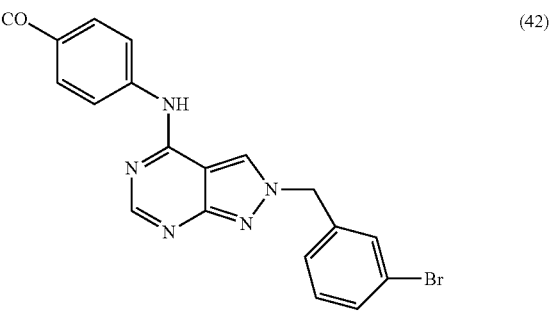
(43) 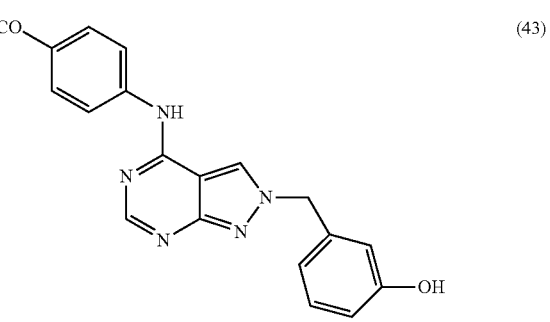

TABLE 2-continued
Compounds of formula III.
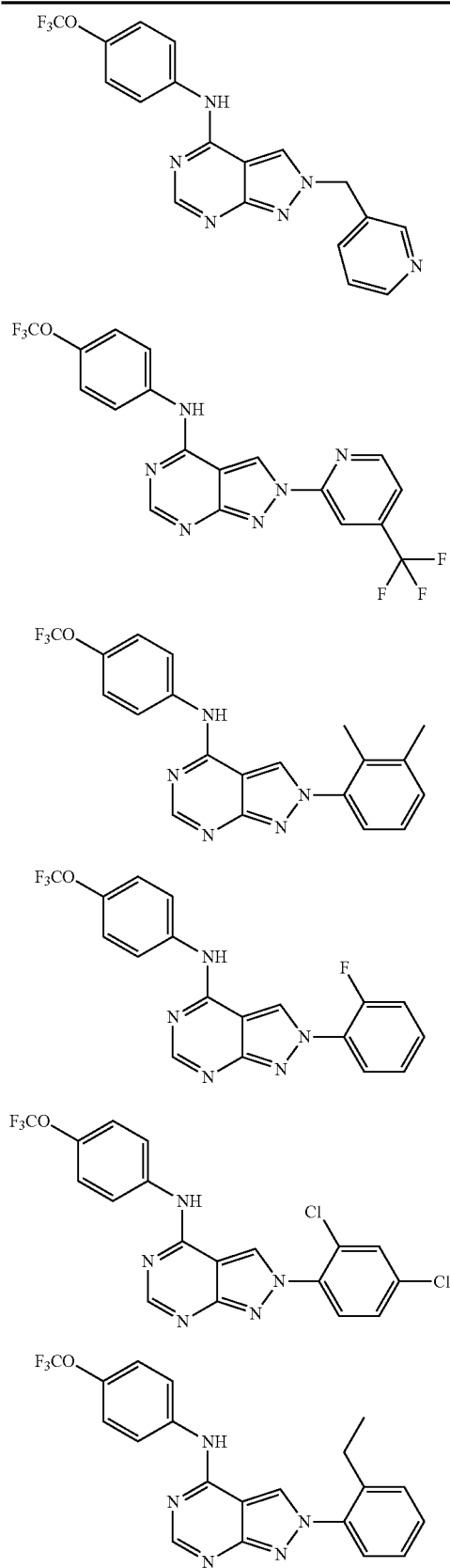
(44) (45) (46) (47) (48) (49)
TABLE 2-continued
Compounds of formula III.
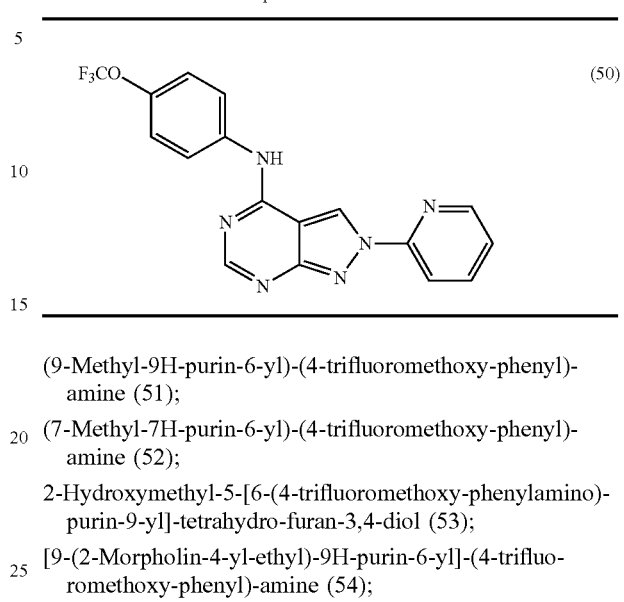
(50)
(9-Methyl-9H-purin-6-yl)-(4-trifluoromethoxy-phenyl)-amine (51);
(7-Methyl-7H-purin-6-yl)-(4-trifluoromethoxy-phenyl)-amine (52);
2-Hydroxymethyl-5-[6-(4-trifluoromethoxy-phenylamino)-purin-9-yl]-tetrahydro-furan-3,4-diol (53);
[9-(2-Morpholin-4-yl-ethyl)-9H-purin-6-yl]-(4-trifluoromethoxy-phenyl)-amine (54);
TABLE 3
Compounds of formula IV.
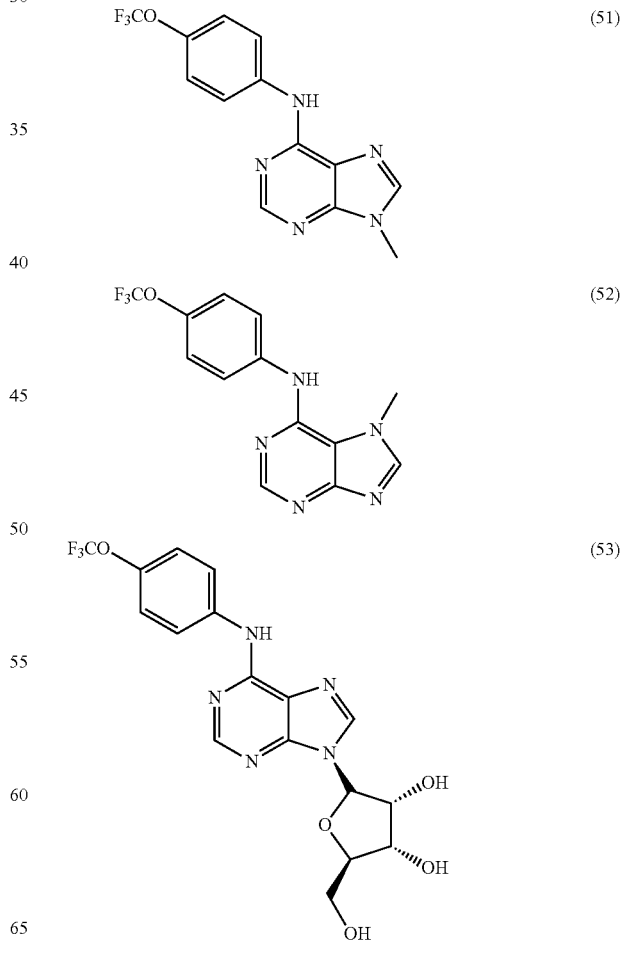
(51) (52) (53)

TABLE 3-continued

Compounds of formula IV.

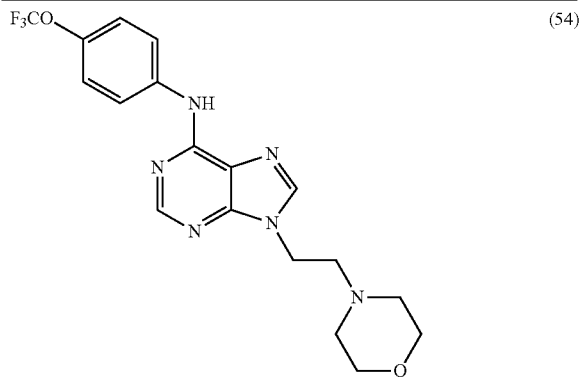
(54)

N-(2-Morpholin-4-yl-ethyl)-3-[4-(4-trifluoromethoxy-phenylamino)-pyrrolo[2,3-d]pyrimidin-7-yl]-propionamide (55);
2-Hydroxymethyl-5-[4-(4-trifluoromethoxy-phenylamino)-pyrrolo[2,3-d]pyrimidin-7-yl]-tetrahydro-furan-3,4-diol (56);
(7H-Pyrrolo[2,3-d]pyrimidin-4-yl)-(4-trifluoromethoxy-phenyl)-amine (57);
(7-Methyl-7H-pyrrolo[2,3-d]pyrimidin-4-yl)-(4-trifluoromethoxy-phenyl)-aminev (58);
2-[4-(4-Trifluoromethoxy-phenylamino)-pyrrolo[2,3-d]pyrimidin-7-yl]-ethanol (59);
[7-(2-Morpholin-4-yl-ethyl)-7H-pyrrolo[2,3-d]pyrimidin-4-yl]-(4-trifluoromethoxy-phenyl)-amine (60);
[7-(4-Methoxy-benzyl)-7H-pyrrolo[2,3-d]pyrimidin-4-yl]-(4-trifluoromethoxy-phenyl)-amine (61);
3-[4-(4-Trifluoromethoxy-phenylamino)-pyrrolo[2,3-d]pyrimidin-7-yl]-propionamide (62);
N-Ethyl-3-[4-(4-trifluoromethoxy-phenylamino)-pyrrolo[2,3-d]pyrimidin-7-yl]-propionamide (63);
N-(3-Methoxy-propyl)-3-[4-(4-trifluoromethoxy-phenylamino)-pyrrolo[2,3-d]pyrimidin-7-yl]-propionamide (64);
N-(2-Morpholin-4-yl-ethyl)-3-[4-(4-trifluoromethoxy-phenylamino)-pyrrolo[2,3-d]pyrimidin-7-yl]-propionamide (65);
7-Methyl-4-(4-trifluoromethoxy-phenylamino)-7H-pyrrolo[2,3-d]pyrimidine-6-carboxylic acid ethyl ester (66);
(4-Bromo-piperidin-1-yl)-[7-methyl-4-(4-trifluoromethoxy-phenylamino)-7H-pyrrolo[2,3-d]pyrimidin-6-yl]-methanone (67);
1-[7-Methyl-4-(4-trifluoromethoxy-phenylamino)-7H-pyrrolo[2,3-d]pyrimidine-6-carbonyl]-piperidine-4-carboxylic acid amide (68);
1-[7-Methyl-4-(4-trifluoromethoxy-phenylamino)-7H-pyrrolo[2,3-d]pyrimidine-6-carbonyl]-piperidine-3-carboxylic acid amide (69);
1-[7-Methyl-4-(4-trifluoromethoxy-phenylamino)-7H-pyrrolo[2,3-d]pyrimidine-6-carbonyl]-piperidine-3-carboxylic acid ethyl ester (70);
(3-Hydroxymethyl-piperidin-1-yl)-[7-methyl-4-(4-trifluoromethoxy-phenylamino)-7H-pyrrolo[2,3-d]pyrimidin-6-yl]-methanone (71);
8-[7-Methyl-4-(4-trifluoromethoxy-phenylamino)-7H-pyrrolo[2,3-d]pyrimidine-6-carbonyl]-1-phenyl-1,3,8-triazaspiro[4.5]decan-4-one (72);
[7-Methyl-4-(4-trifluoromethoxy-phenylamino)-7H-pyrrolo[2,3-d]pyrimidin-6-yl]-methanol (73);
(2-Methoxymethyl-pyrrolidin-1-yl)-[7-methyl-4-(4-trifluoromethoxy-phenylamino)-7H-pyrrolo[2,3-d]pyrimidin-6-yl]-methanone (74);
7-Methyl-4-(4-trifluoromethoxy-phenylamino)-7H-pyrrolo[2,3-d]pyrimidine-6-carboxylic acid amide (75);
7-Methyl-4-(4-trifluoromethoxy-phenylamino)-7H-pyrrolo[2,3-d]pyrimidine-6-carboxylic acid ethylamide (76);
7-Methyl-4-(4-trifluoromethoxy-phenylamino)-7H-pyrrolo[2,3-d]pyrimidine-6-carboxylic acid (1-ethyl-pyrrolidin-2-yl)-amide (77);
N-[7-Methyl-4-(4-trifluoromethoxy-phenylamino)-7H-pyrrolo[2,3-d]pyrimidine-6-carbonyl]-guanidine (78);
7-Methyl-4-(4-trifluoromethoxy-phenylamino)-7H-pyrrolo[2,3-d]pyrimidine-6-carboxylic acid (4-diethylamino-1-methyl-butyl)-amide (79);
4-(2-Bromo-4-trifluoromethoxy-phenylamino)-1-(2-morpholin-4-yl-ethyl)-1H-pyrrolo[2,3-b]pyridine-5-carbaldehyde (80);

TABLE 4

Compounds of formula V.

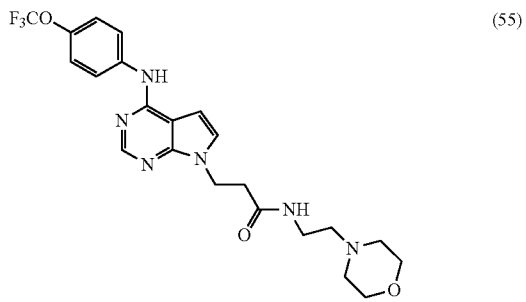
(55)

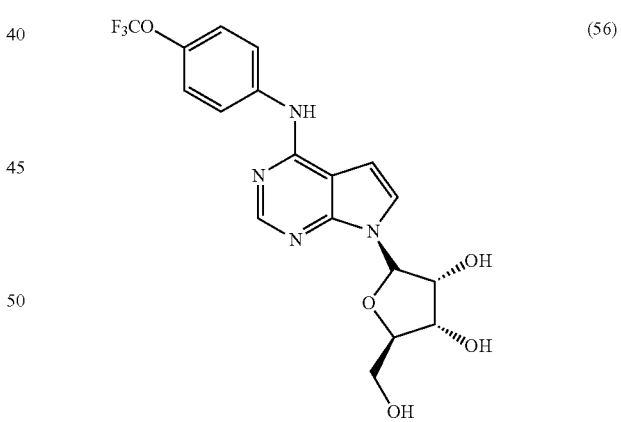
(56)

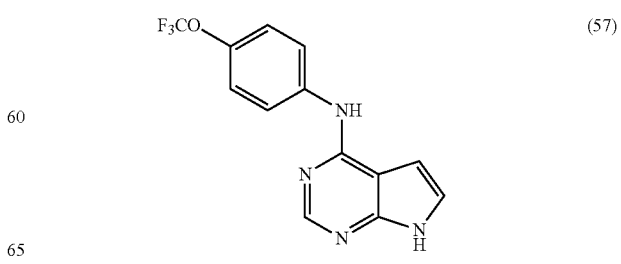
(57)

TABLE 4-continued
Compounds of formula V.
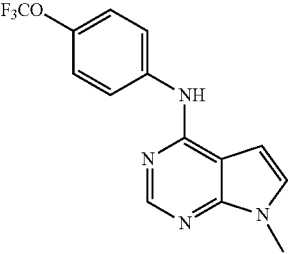 [SMILES: Cn1ccc2c(Nc3ccc(OC(F)(F)F)cc3)ncnc21] (58)
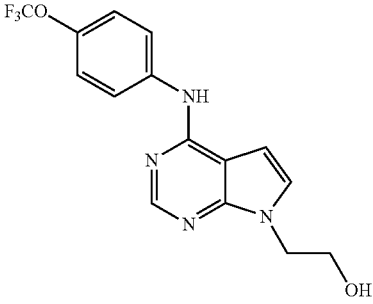 [SMILES: OCCn1ccc2c(Nc3ccc(OC(F)(F)F)cc3)ncnc21] (59)
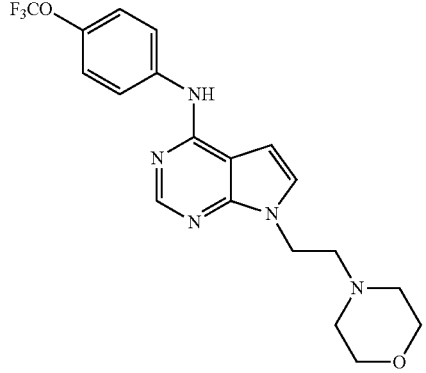 [SMILES: FC(F)(F)Oc1ccc(Nc2ncnc3c2ccn3CCN2CCOCC2)cc1] (60)
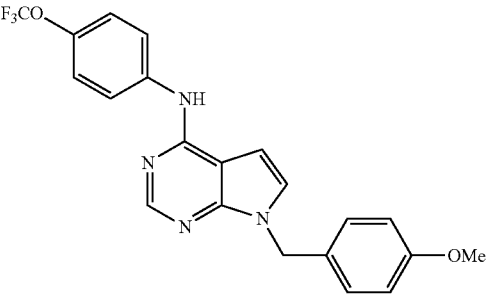 [SMILES: COc1ccc(Cn2ccc3c(Nc4ccc(OC(F)(F)F)cc4)ncnc32)cc1] (61)
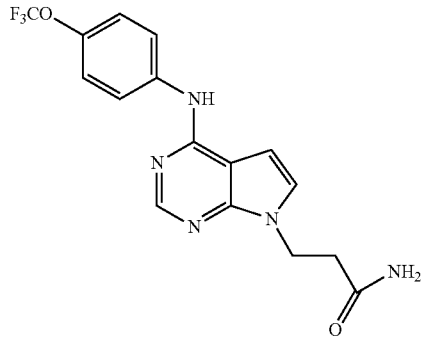 [SMILES: NC(=O)CCn1ccc2c(Nc3ccc(OC(F)(F)F)cc3)ncnc21] (62)
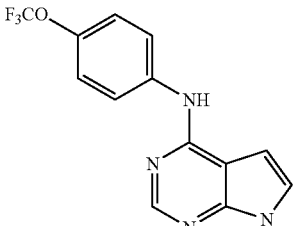 (63)
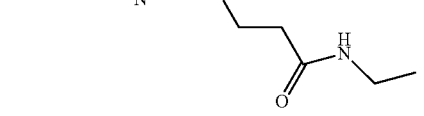 (64)
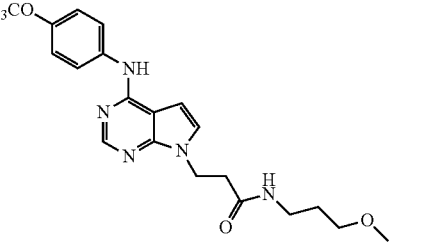 (65)
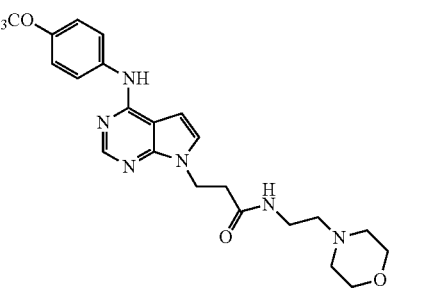 (66)
 (67)

TABLE 4-continued
Compounds of formula V.
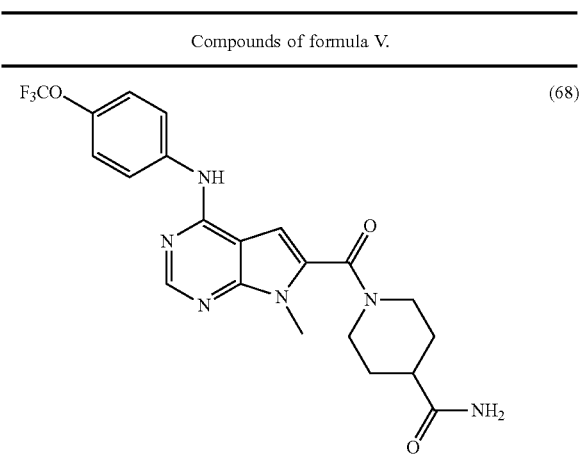 (68)
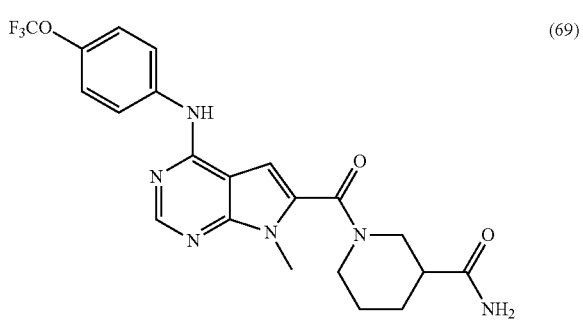 (69)
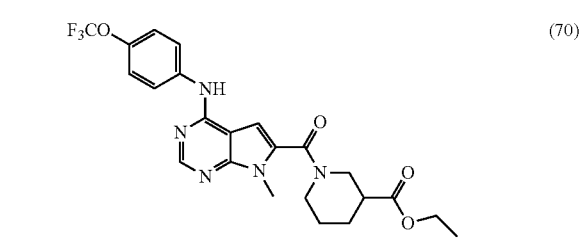 (70)
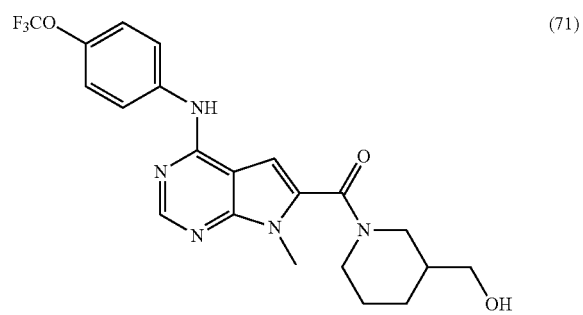 (71)
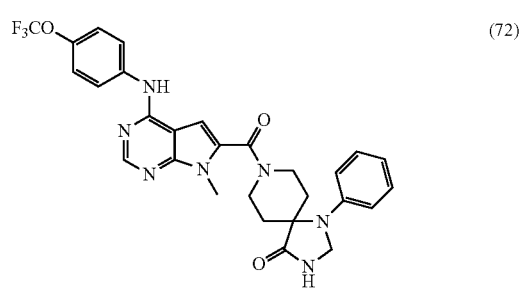 (72)
TABLE 4-continued
Compounds of formula V.
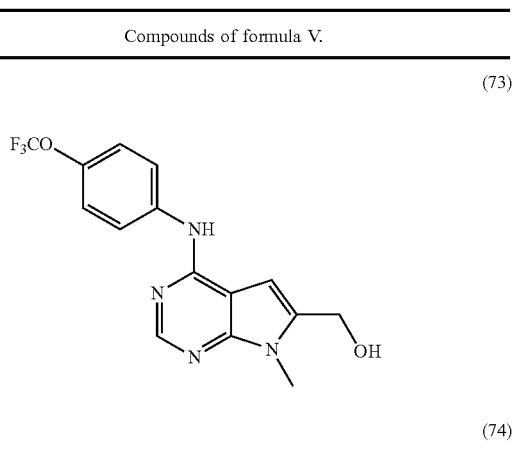 (73)
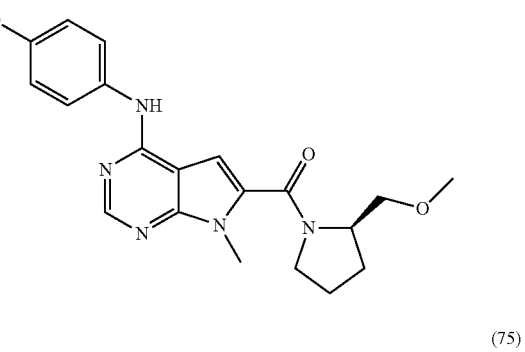 (74)
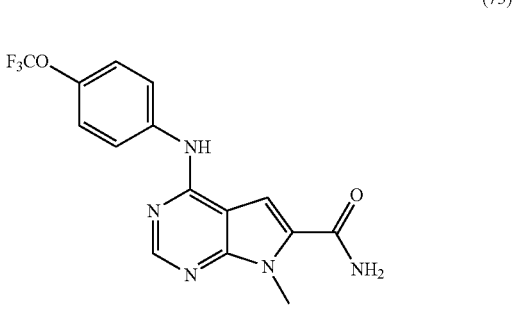 (75)
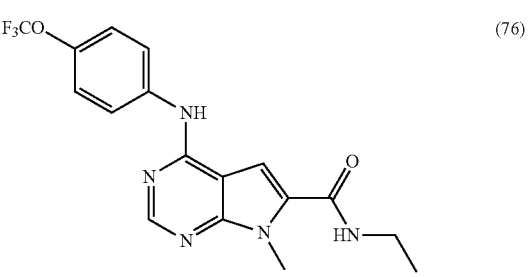 (76)
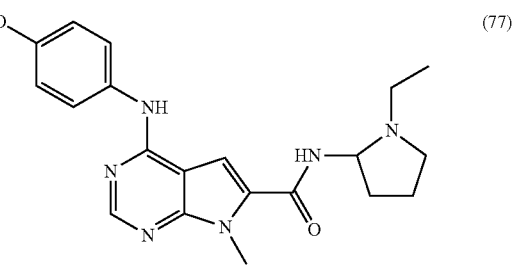 (77)

TABLE 4-continued

Compounds of formula V.

(78)

(79)

(80)

N-(2-hydroxyethyl)-4-(4-(trifluoromethoxy)phenylamino) thieno[2,3-d]pyrimidine-6-carboxamide (81);
Thieno[2,3-d]pyrimidin-4-yl-(4-trifluoromethoxy-phenyl)-amine (82);
(6-Methyl-thieno[2,3-d]pyrimidin-4-yl)-(4-trifluoromethoxy-phenyl)-amine (83);

4-(4-Trifluoromethoxy-phenylamino)-thieno[2,3-d]pyrimidine-6-carboxylic acid methyl ester (84);
4-(4-Trifluoromethoxy-phenylamino)-thieno[2,3-d]pyrimidine-6-carboxylic acid (85);
4-(4-Trifluoromethoxy-phenylamino)-thieno[2,3-d]pyrimidine-6-carboxylic acid (2-morpholin-4-yl-ethyl)-amide (86);
[4-(4-Trifluoromethoxy-phenylamino)-thieno[2,3-d]pyrimidin-6-yl]-methanol (87);
4-(4-Trifluoromethoxy-phenylamino)-thieno[2,3-d]pyrimidine-6-carboxylic acid ethylamide (88);
4-(4-Trifluoromethoxy-phenylamino)-thieno[2,3-d]pyrimidine-6-carboxylic acid (2-hydroxy-ethyl)-amide (89);
[6-(3-Dimethylamino-pyrrolidin-1-ylmethyl)-thieno[2,3-d]pyrimidin-4-yl]-(4-trifluoromethoxy-phenyl)-amine (90);
(3-Dimethylamino-pyrrolidin-1-yl)-[4-(4-trifluoromethoxy-phenylamino)-thieno[2,3-d]pyrimidin-6-yl]-methanone (91);
4-(4-Trifluoromethoxy-phenylamino)-thieno[2,3-d]pyrimidine-6-carboxylic acid (1-benzyl-pyrrolidin-3-yl)-amide (92);
(2-Hydroxymethyl-pyrrolidin-1-yl)-[4-(4-trifluoromethoxy-phenylamino)-thieno[2,3-d]pyrimidin-6-yl]-methanone (93);
Piperazin-1-yl-[4-(4-trifluoromethoxy-phenylamino)-thieno[2,3-d]pyrimidin-6-yl]-methanone (94);
(4-Pyrrolidin-1-yl-piperazin-1-yl)-[4-(4-trifluoromethoxy-phenylamino)-thieno[2,3-d]pyrimidin-6-yl]-methanone (95);
[4-(4-Trifluoromethoxy-phenylamino)-thieno[2,3-d]pyrimidin-6-yl]-[4-(3-trifluoromethyl-phenyl)-piperazin-1-yl]-methanone (96);
4-(4-Trifluoromethoxy-phenylamino)-thieno[2,3-d]pyrimidine-6-carboxylic acid (2-morpholin-4-yl-ethyl)-amide (97);
(4-Methyl-piperazin-1-yl)-[4-(4-trifluoromethoxy-phenylamino)-thieno[2,3-d]pyrimidin-6-yl]-methanone (98);
(4-Hydroxy-piperidin-1-yl)-[4-(4-trifluoromethoxy-phenylamino)-thieno[2,3-d]pyrimidin-6-yl]-methanone (99);
(4-Methoxy-piperidin-1-yl)-[4-(4-trifluoromethoxy-phenylamino)-thieno[2,3-d]pyrimidin-6-yl]-methanone (100);
4-(4-Trifluoromethoxy-phenylamino)-thieno[2,3-d]pyrimidine-6-carboxylic acid [2-methyl-5-(3-trifluoromethyl-benzoylamino)-phenyl]-amide (101);

TABLE 5

Compounds of formula VI.

(81)

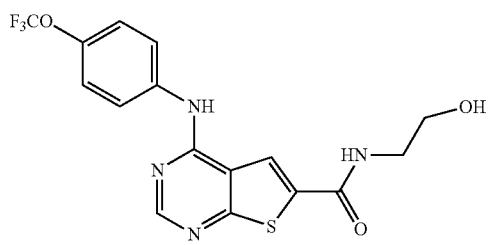 [SMILES: O=C(NCCO)c1cc2c(Nc3ccc(OC(F)(F)F)cc3)ncnc2s1]

TABLE 5-continued
Compounds of formula VI.
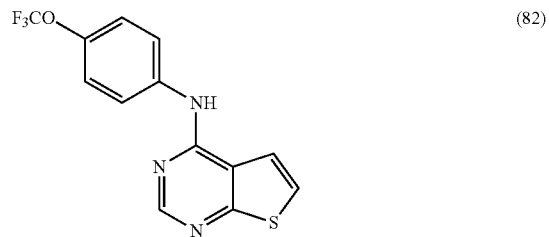
(82)
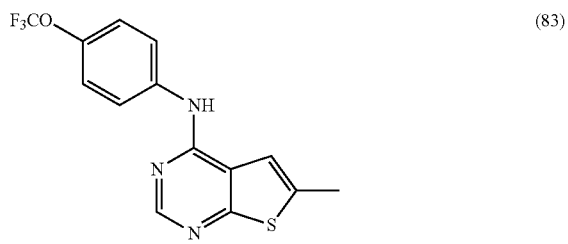
(83)
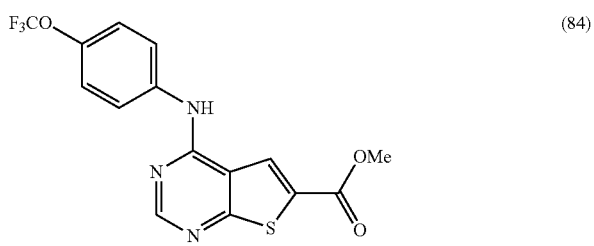
(84)
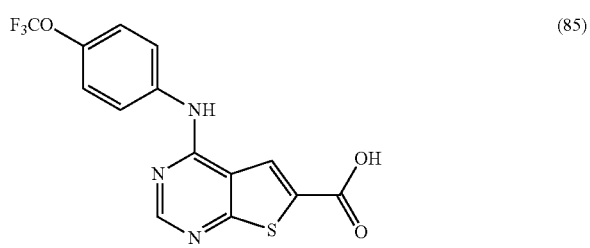
(85)
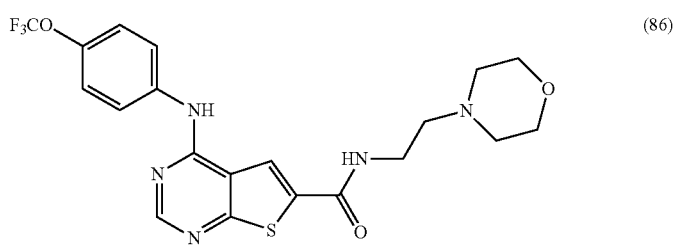
(86)
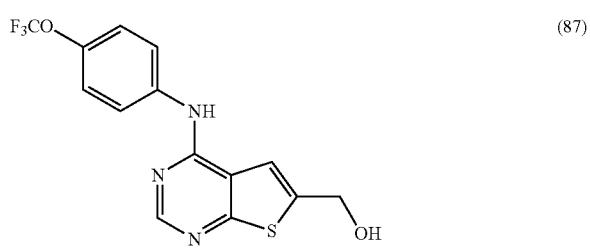
(87)

TABLE 5-continued
Compounds of formula VI.
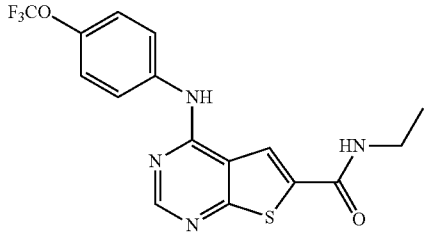 [SMILES: CCNC(=O)c1cc2c(Nc3ccc(OC(F)(F)F)cc3)ncnc2s1]
(88)
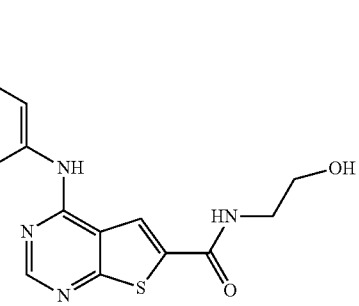
(89)
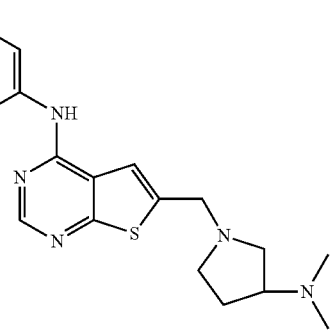
(90)
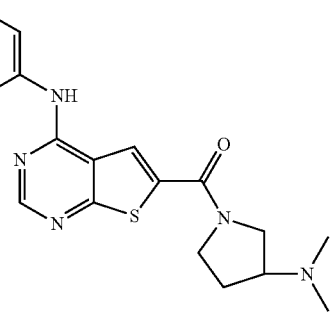
(91)
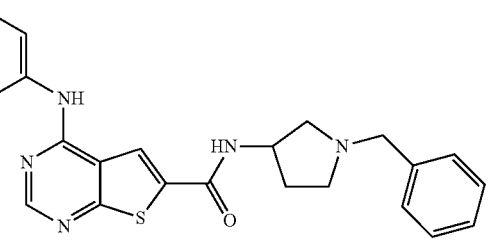
(92)

TABLE 5-continued
Compounds of formula VI.
(93)
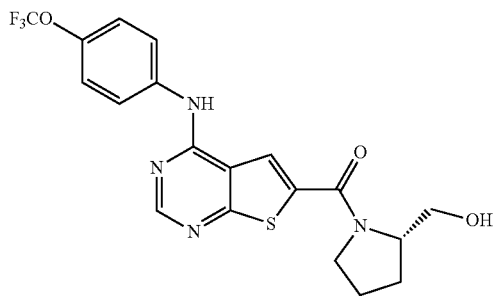 [SMILES: O=C(c1cc2c(Nc3ccc(OC(F)(F)F)cc3)ncnc2s1)N1CCC[C@H]1CO]
(94)
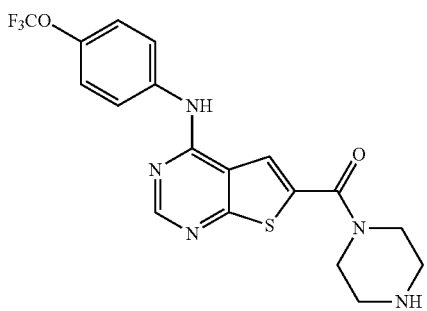 [SMILES: O=C(c1cc2c(Nc3ccc(OC(F)(F)F)cc3)ncnc2s1)N1CCNCC1]
(95)
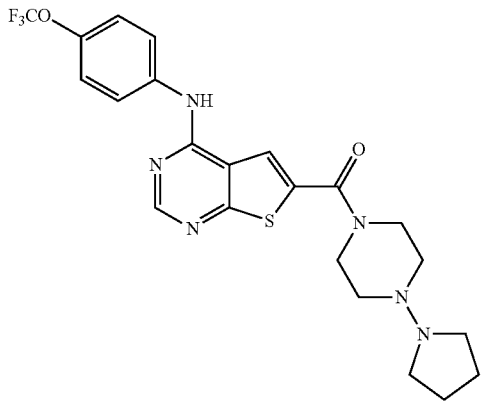 [SMILES: O=C(c1cc2c(Nc3ccc(OC(F)(F)F)cc3)ncnc2s1)N1CCN(N2CCCC2)CC1]
(96)
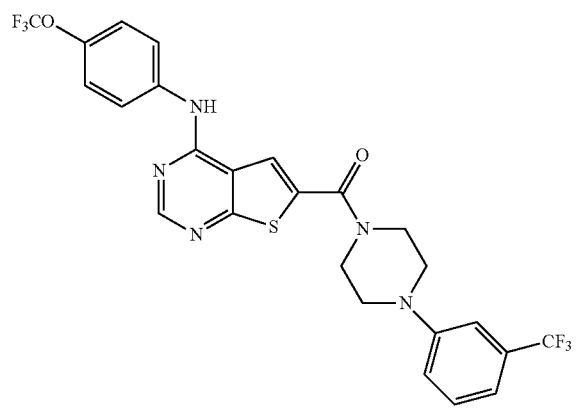 [SMILES: O=C(c1cc2c(Nc3ccc(OC(F)(F)F)cc3)ncnc2s1)N1CCN(c2cccc(C(F)(F)F)c2)CC1]

TABLE 5-continued
Compounds of formula VI.
(97)
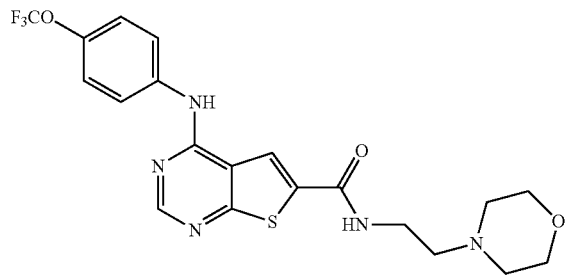 [SMILES: O=C(NCCN1CCOCC1)c1cc2c(Nc3ccc(OC(F)(F)F)cc3)ncnc2s1]
(98)
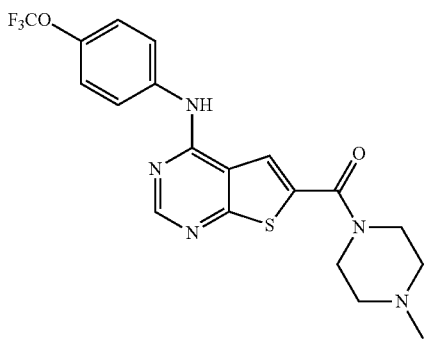 [SMILES: CN1CCN(C(=O)c2cc3c(Nc4ccc(OC(F)(F)F)cc4)ncnc3s2)CC1]
(99)
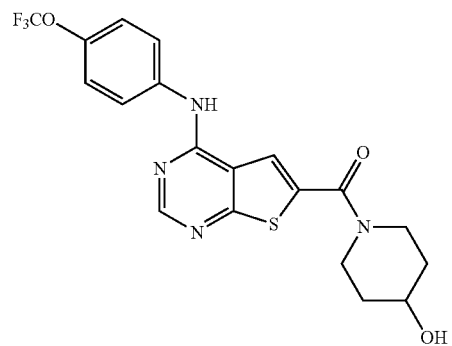 [SMILES: O=C(c1cc2c(Nc3ccc(OC(F)(F)F)cc3)ncnc2s1)N1CCC(O)CC1]

TABLE 5-continued

Compounds of formula VI.

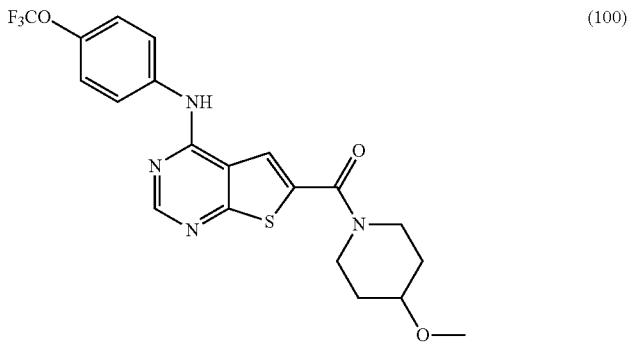

(100)

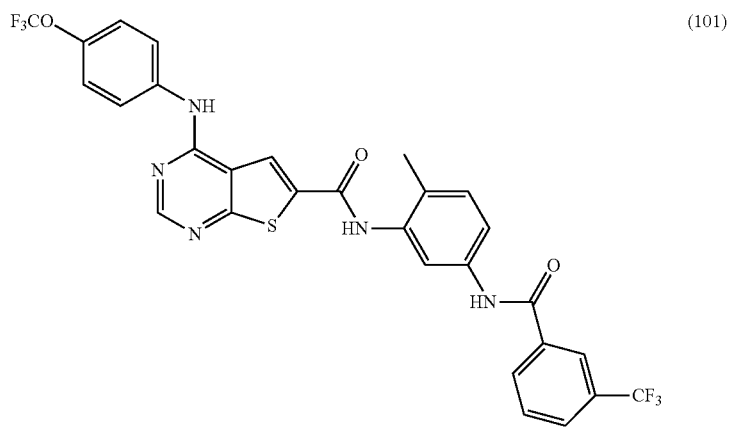

(101)

4-(4-(trifluoromethoxy)phenylamino)-N-(2-hydroxyethyl) quinazoline-7-carboxamide (102);
4-(4-Trifluoromethoxy-phenylamino)-quinazoline-7-carboxylic acid methyl ester (103);
[4-(4-Trifluoromethoxy-phenylamino)-quinazolin-7-yl]-methanol (104);
(7-Diethylaminomethyl-quinazolin-4-yl)-(4-trifluoromethoxy-phenyl)-amine (105);
4-(4-Trifluoromethoxy-phenylamino)-quinazoline-7-carboxylic acid diethylamide (106);
[4-(Furan-3-carbonyl)-piperazin-1-yl]-[4-(4-trifluoromethoxy-phenylamino)-quinazolin-7-yl]-methanone (107);
4-(4-Trifluoromethoxy-phenylamino)-quinazoline-7-carboxylic acid (3-trifluoromethyl-phenyl)-amide (108);
4-(4-Trifluoromethoxy-phenylamino)-quinazoline-7-carboxylic acid (3-methoxy-propyl)-amide (109);
4-(4-Trifluoromethoxy-phenylamino)-quinazoline-7-carboxylic acid N'-ethyl-hydrazide (110);
(2-{[4-(4-Trifluoromethoxy-phenylamino)-quinazoline-7-carbonyl]-amino}-thiazol-5-yl)-acetic acid ethyl ester (111);
(4-Methoxy-piperidin-1-yl)-[4-(4-trifluoromethoxy-phenylamino)-quinazolin-7-yl]-methanone (112);
(3-Hydroxy-pyrrolidin-1-yl)-[4-(4-trifluoromethoxy-phenylamino)-quinazolin-7-yl]-methanone (113);
(2-Hydroxymethyl-pyrrolidin-1-yl)-[4-(4-trifluoromethoxy-phenylamino)-quinazolin-7-yl]-methanone (114);
(3-Dimethylamino-pyrrolidin-1-yl)-[4-(4-trifluoromethoxy-phenylamino)-quinazolin-7-yl]-methanone (115);
4-(4-Trifluoromethoxy-phenylamino)-quinazoline-7-carboxylic acid (2-hydroxy-ethyl)-methyl-amide (116);
4-(4-Trifluoromethoxy-phenylamino)-quinazoline-7-carboxylic acid methyl-(1-methyl-piperidin-4-yl)-amide (117);
4-Methyl-N-[4-(4-trifluoromethoxy-phenylamino)-quinazoline-7-carbonyl]-benzenesulfonamide (118);
2-Methyl-propane-2-sulfonic acid [4-(4-trifluoromethoxy-phenylamino)-quinazoline-7-carbonyl]-amide (119);
(4-Methyl-[1,4]diazepan-1-yl)-[4-(4-trifluoromethoxy-phenylamino)-quinazolin-7-yl]-methanone (120);
(3,5-Dimethyl-piperazin-1-yl)-[4-(4-trifluoromethoxy-phenylamino)-quinazolin-7-yl]-methanone (121);
(4-Hydroxy-piperidin-1-yl)-[4-(4-trifluoromethoxy-phenylamino)-quinazolin-7-yl]-methanone (122);
4-(4-Trifluoromethoxy-phenylamino)-quinazoline-7-carboxylic acid methyl-(2-methylamino-ethyl)-amide (123);
4-(4-Trifluoromethoxy-phenylamino)-quinazoline-7-carboxylic acid (2-hydroxy-ethyl)-amide (124);
1-Phenyl-8-[4-(4-trifluoromethoxy-phenylamino)-quinazoline-7-carbonyl]-1,3,8-triaza-spiro[4.5]decan-4-one (125);
(4-Bromo-piperidin-1-yl)-[4-(4-trifluoromethoxy-phenylamino)-quinazolin-7-yl]-methanone (126);
1-[4-(4-Trifluoromethoxy-phenylamino)-quinazoline-7-carbonyl]-piperidine-4-carboxylic acid amide (127);
1-[4-(4-Trifluoromethoxy-phenylamino)-quinazoline-7-carbonyl]-piperidine-3-carboxylic acid amide (128);
1-[4-(4-Trifluoromethoxy-phenylamino)-quinazoline-7-carbonyl]-piperidine-3-carboxylic acid ethyl ester (129);
(3-Hydroxymethyl-piperidin-1-yl)-[4-(4-trifluoromethoxy-phenylamino)-quinazolin-7-yl]-methanone (130);

TABLE 6
Compounds of formula VII.
(102)
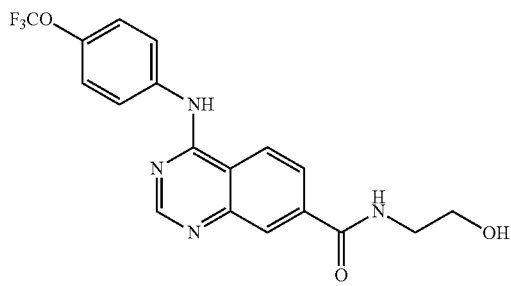 [SMILES: O=C(NCCO)c1ccc2c(Nc3ccc(OC(F)(F)F)cc3)ncnc2c1]
(103)
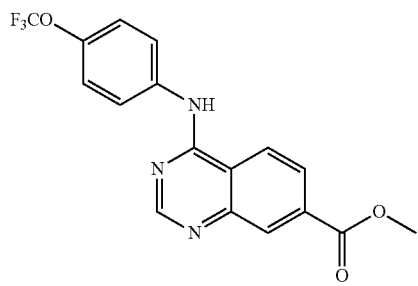 [SMILES: COC(=O)c1ccc2c(Nc3ccc(OC(F)(F)F)cc3)ncnc2c1]
(104)
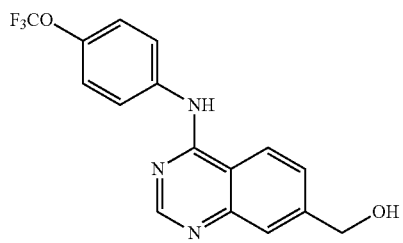 [SMILES: OCc1ccc2c(Nc3ccc(OC(F)(F)F)cc3)ncnc2c1]
(105)
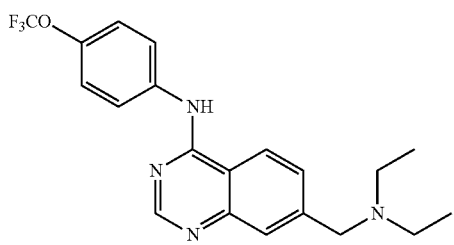 [SMILES: CCN(CC)Cc1ccc2c(Nc3ccc(OC(F)(F)F)cc3)ncnc2c1]
(106)
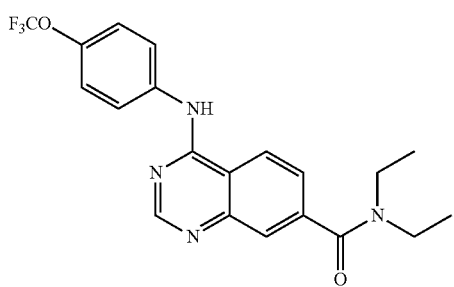 [SMILES: CCN(CC)C(=O)c1ccc2c(Nc3ccc(OC(F)(F)F)cc3)ncnc2c1]

TABLE 6-continued
Compounds of formula VII.
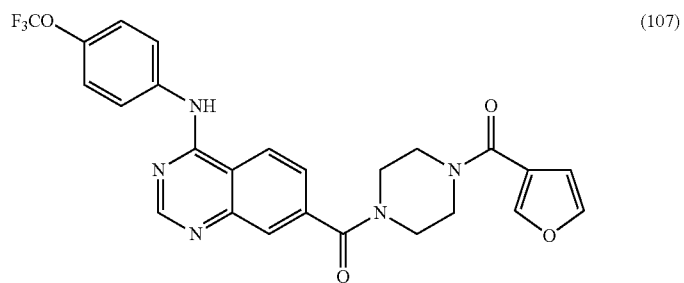 (107)
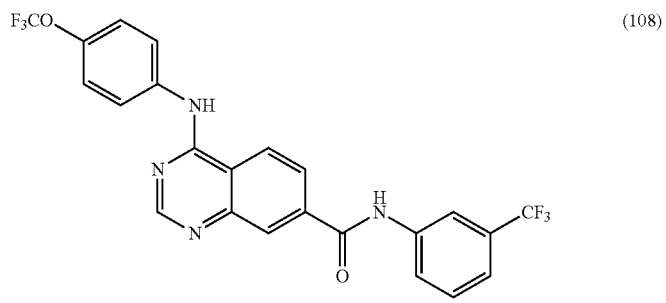 (108)
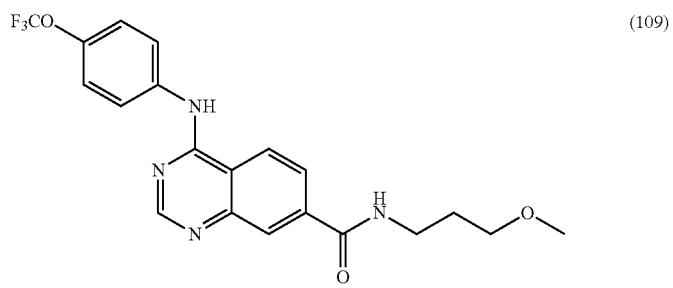 (109)
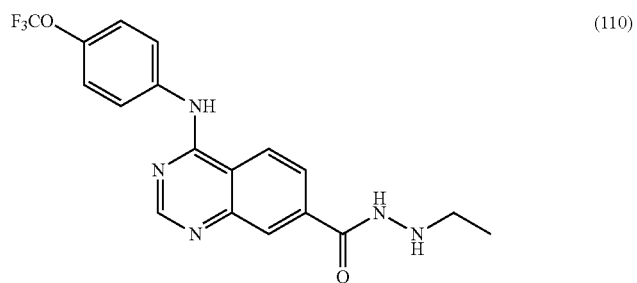 (110)
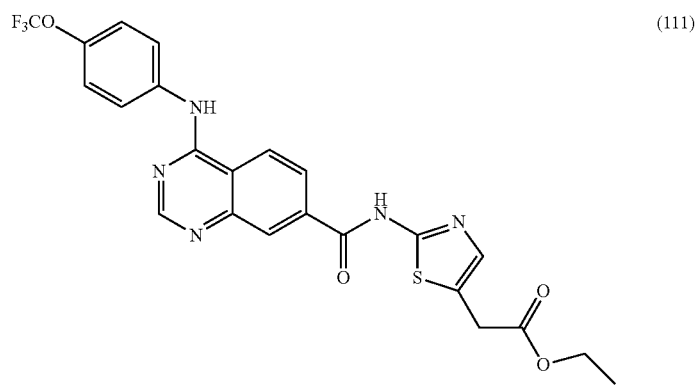 (111)

TABLE 6-continued
Compounds of formula VII.
(112)
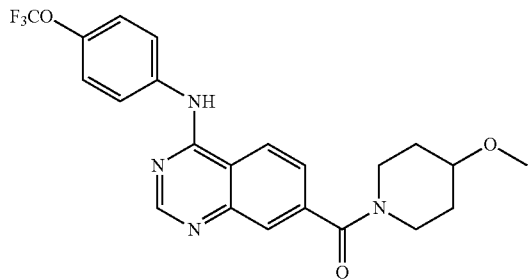 [SMILES: COC1CCN(C(=O)c2ccc3c(Nc4ccc(OC(F)(F)F)cc4)ncnc3c2)CC1]
(113)
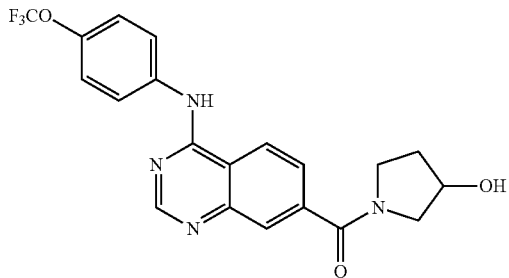 [SMILES: O=C(c1ccc2c(Nc3ccc(OC(F)(F)F)cc3)ncnc2c1)N1CCC(O)C1]
(114)
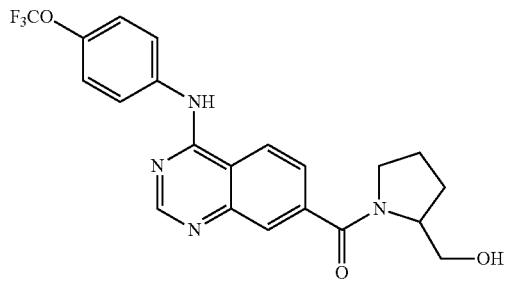 [SMILES: O=C(c1ccc2c(Nc3ccc(OC(F)(F)F)cc3)ncnc2c1)N1CCCC1CO]
(115)
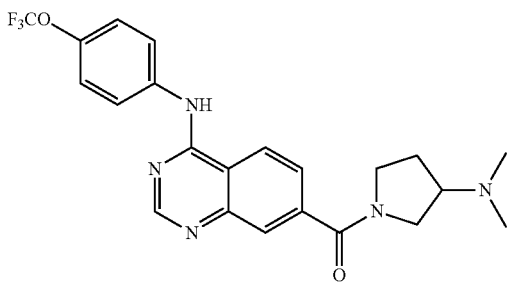 [SMILES: CN(C)C1CCN(C(=O)c2ccc3c(Nc4ccc(OC(F)(F)F)cc4)ncnc3c2)C1]
(116)
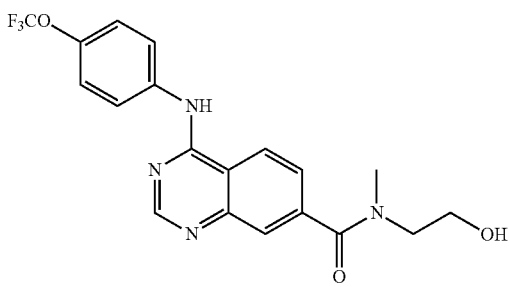

TABLE 6-continued
Compounds of formula VII.
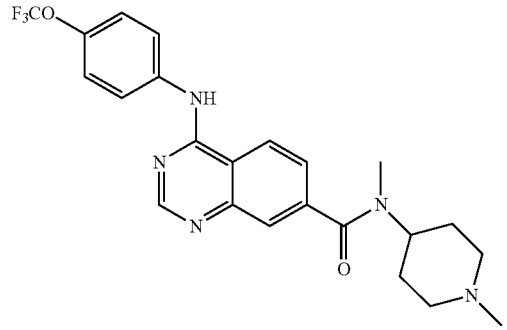 [SMILES: CN1CCC(N(C)C(=O)c2ccc3c(Nc4ccc(OC(F)(F)F)cc4)ncnc3c2)CC1]
(117)
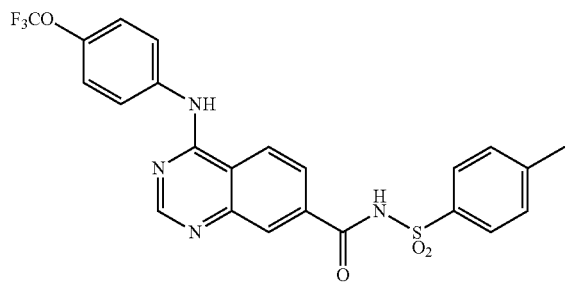 [SMILES: Cc1ccc(S(=O)(=O)NC(=O)c2ccc3c(Nc4ccc(OC(F)(F)F)cc4)ncnc3c2)cc1]
(118)
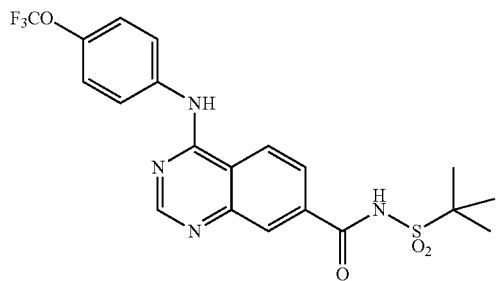 [SMILES: CC(C)(C)S(=O)(=O)NC(=O)c1ccc2c(Nc3ccc(OC(F)(F)F)cc3)ncnc2c1]
(119)
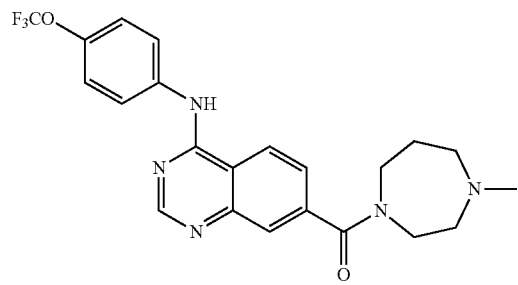 [SMILES: CN1CCCN(C(=O)c2ccc3c(Nc4ccc(OC(F)(F)F)cc4)ncnc3c2)CC1]
(120)
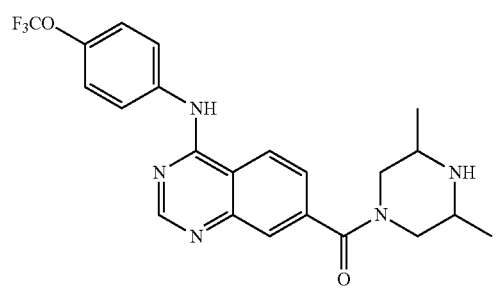 [SMILES: CC1CN(C(=O)c2ccc3c(Nc4ccc(OC(F)(F)F)cc4)ncnc3c2)CC(C)N1]
(121)

TABLE 6-continued
Compounds of formula VII.
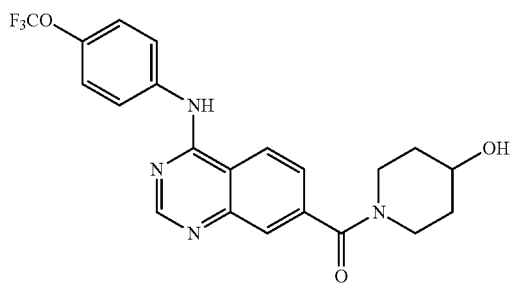 [SMILES: O=C(c1ccc2c(Nc3ccc(OC(F)(F)F)cc3)ncnc2c1)N1CCC(O)CC1]
(122)
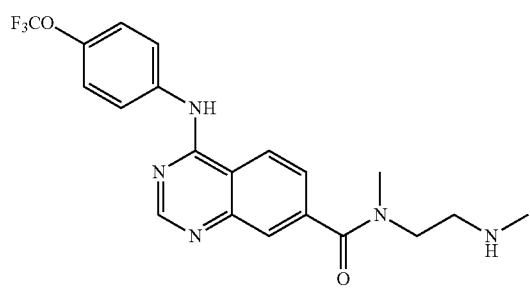 [SMILES: CNCCN(C)C(=O)c1ccc2c(Nc3ccc(OC(F)(F)F)cc3)ncnc2c1]
(123)
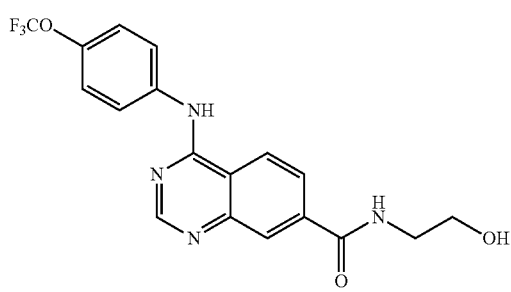 [SMILES: O=C(NCCO)c1ccc2c(Nc3ccc(OC(F)(F)F)cc3)ncnc2c1]
(124)
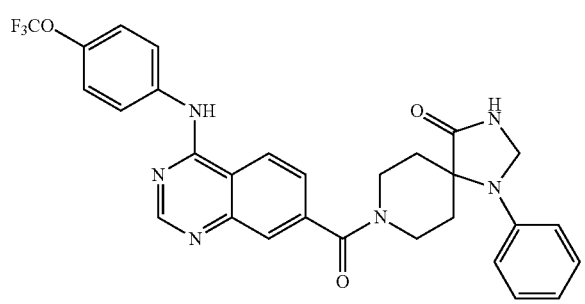 [SMILES: O=C(c1ccc2c(Nc3ccc(OC(F)(F)F)cc3)ncnc2c1)N1CCC2(CC1)C(=O)NCN2c1ccccc1]
(125)
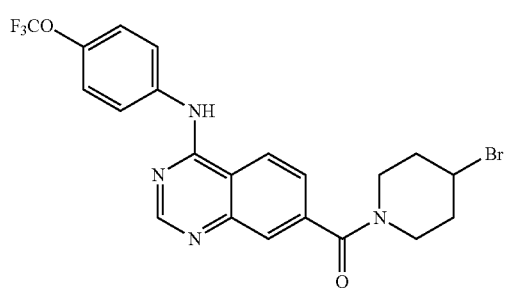 [SMILES: O=C(c1ccc2c(Nc3ccc(OC(F)(F)F)cc3)ncnc2c1)N1CCC(Br)CC1]
(126)

TABLE 6-continued
Compounds of formula VII.
(127)
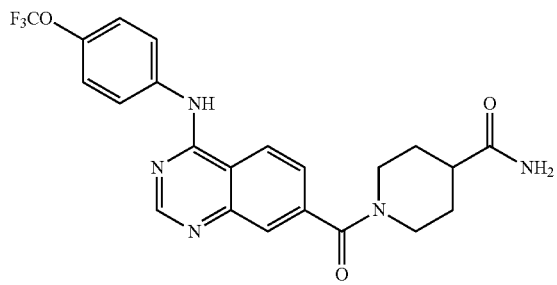 [SMILES: NC(=O)C1CCN(C(=O)c2ccc3c(Nc4ccc(OC(F)(F)F)cc4)ncnc3c2)CC1]
(128)
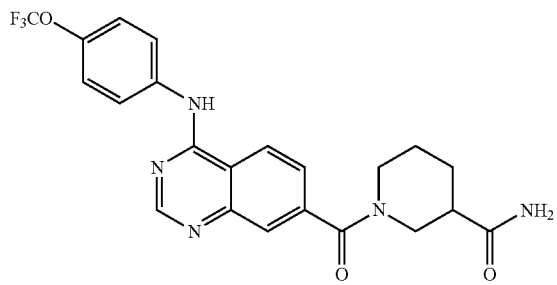 [SMILES: NC(=O)C1CCCN(C(=O)c2ccc3c(Nc4ccc(OC(F)(F)F)cc4)ncnc3c2)C1]
(129)
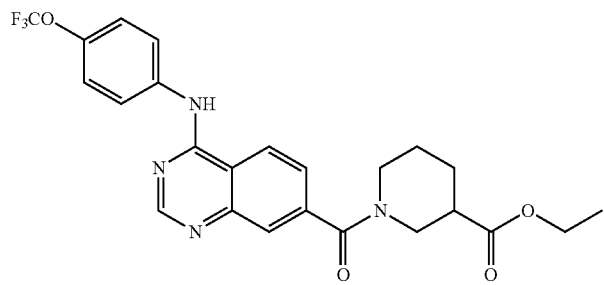 [SMILES: CCOC(=O)C1CCCN(C(=O)c2ccc3c(Nc4ccc(OC(F)(F)F)cc4)ncnc3c2)C1]
(130)
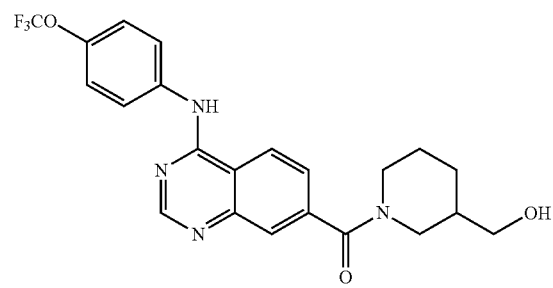 [SMILES: O=C(c1ccc2c(Nc3ccc(OC(F)(F)F)cc3)ncnc2c1)N1CCCC(CO)C1]

4-(4-Trifluoromethoxy-phenylamino)-5,7-dihydro-pyrrolo
[2,3-d]pyrimidin-6-one (131);
7-Methyl-4-(4-trifluoromethoxy-phenylamino)-5,7-dihydro-pyrrolo[2,3-d]pyrimidin-6-one (132);

TABLE 7

Compounds of formula VIII.

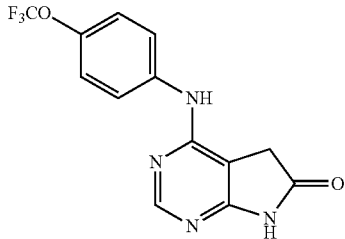 [SMILES: O=C1Cc2c(ncnc2Nc2ccc(OC(F)(F)F)cc2)N1]
(131)

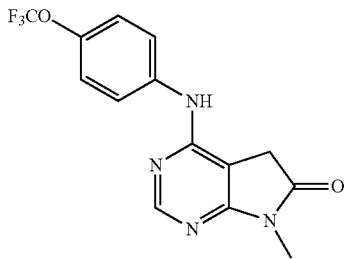 [SMILES: CN1C(=O)Cc2c(Nc3ccc(OC(F)(F)F)cc3)ncnc21]
(132)

4-(6-(4-(trifluoromethoxy)phenylamino)-5-methylpyrimidin-4-yl)-N-(2-morpholinoethyl) benzamide (133);
6-(1H-pyrrolo[2,3-b]pyridin-1-yl)-N-(4-(trifluoromethoxy)phenyl)pyrimidin-4-amine (134);
N-(4-(trifluoromethoxy)phenyl)-6-(1,3,5-trimethyl-1H-pyrazol-4-yl)pyrimidin-4-amine (135);
4-[6-(4-Trifluoromethoxy-phenylamino)-pyrimidin-4-yl]-benzenesulfonamide (136);
4-[5-Methyl-6-(4-trifluoromethoxy-phenylamino)-pyrimidin-4-yl]-benzenesulfonamide (137);
N-Methyl-4-[5-methyl-6-(4-trifluoromethoxy-phenylamino)-pyrimidin-4-yl]-benzenesulfonamide (138);
N-Ethyl-4-[6-(4-trifluoromethoxy-phenylamino)-pyrimidin-4-yl]-benzenesulfonamide (139);
N-(2-Hydroxy-ethyl)-4-[6-(4-trifluoromethoxy-phenylamino)-pyrimidin-4-yl]-benzenesulfonamide (140);
[6-(4-Methanesulfonyl-phenyl)-pyrimidin-4-yl]-(4-trifluoromethoxy-phenyl)-amine (141);
[6-(4-Methanesulfonyl-phenyl)-5-methyl-pyrimidin-4-yl]-(4-trifluoromethoxy-phenyl)-amine (142);
{6-[4-(Propane-2-sulfonyl)-phenyl]-pyrimidin-4-yl}-(4-trifluoromethoxy-phenyl)-amine (143);
{5-Methyl-6-[4-(propane-2-sulfonyl)-phenyl]-pyrimidin-4-yl}-(4-trifluoromethoxy-phenyl)-amine (144);
N,N-Diethyl-4-[6-(4-trifluoromethoxy-phenylamino)-pyrimidin-4-yl]-benzenesulfonamide (145);
N,N-Diethyl-4-[5-methyl-6-(4-trifluoromethoxy-phenylamino)-pyrimidin-4-yl]-benzenesulfonamide (146);
{6-[4-(Piperidine-1-sulfonyl)-phenyl]-pyrimidin-4-yl}-(4-trifluoromethoxy-phenyl)-amine (147);
4-Methyl-N-{4-[6-(4-trifluoromethoxy-phenylamino)-pyrimidin-4-yl]-phenyl}-benzenesulfonamide (148);
4-Methyl-N-{4-[5-methyl-6-(4-trifluoromethoxy-phenylamino)-pyrimidin-4-yl]-phenyl}-benzenesulfonamide (149);
{6-[4-(Morpholine-4-sulfonyl)-phenyl]-pyrimidin-4-yl}-(4-trifluoromethoxy-phenyl)-amine (150);
N-{4-[6-(4-Trifluoromethoxy-phenylamino)-pyrimidin-4-yl]-phenyl}-methanesulfonamide (151);
Ethanesulfonic acid {4-[6-(4-trifluoromethoxy-phenylamino)-pyrimidin-4-yl]-phenyl}-amide (152);
Butane-1-sulfonic acid {4-[6-(4-trifluoromethoxy-phenylamino)-pyrimidin-4-yl]-phenyl}-amide (153);
Propane-2-sulfonic acid {4-[6-(4-trifluoromethoxy-phenylamino)-pyrimidin-4-yl]-phenyl}-amide (154);
Pentane-2-sulfonic acid {4-[6-(4-trifluoromethoxy-phenylamino)-pyrimidin-4-yl]-phenyl}-amide (155);
N-(2-Hydroxy-ethyl)-4-[5-methyl-6-(4-trifluoromethoxy-phenylamino)-pyrimidin-4-yl]-benzamide (156);
4-[5-Methyl-6-(4-trifluoromethoxy-phenylamino)-pyrimidin-4-yl]-N-(2-morpholin-4-yl-ethyl)-benzamide (157);
N-(3-Methoxy-propyl)-4-[5-methyl-6-(4-trifluoromethoxy-phenylamino)-pyrimidin-4-yl]-benzamide (158);
N-{3-[5-Methyl-6-(4-trifluoromethoxy-phenylamino)-pyrimidin-4-yl]-phenyl}-acetamide (159);
3-[5-Methyl-6-(4-trifluoromethoxy-phenylamino)-pyrimidin-4-yl]-benzamide (160);
3-[5-Methyl-6-(4-trifluoromethoxy-phenylamino)-pyrimidin-4-yl]-benzoic acid (161);
(6-Biphenyl-4-yl-pyrimidin-4-yl)-(4-trifluoromethoxy-phenyl)-amine (162);
(6-Biphenyl-4-yl-5-methyl-pyrimidin-4-yl)-(4-trifluoromethoxy-phenyl)-amine (163);
[6-(5-Methoxy-naphthalen-2-yl)-pyrimidin-4-yl]-(4-trifluoromethoxy-phenyl)-amine (164);
[6-(5-Methoxy-naphthalen-2-yl)-5-methyl-pyrimidin-4-yl]-(4-trifluoromethoxy-phenyl)-amine (165);
{3-[6-(4-Trifluoromethoxy-phenylamino)-pyrimidin-4-yl]-phenyl}-acetonitrile (166);
[6-(3-Nitro-phenyl)-pyrimidin-4-yl]-(4-trifluoromethoxy-phenyl)-amine (167);
4-Methoxy-N-{4-[6-(4-trifluoromethoxy-phenylamino)-pyrimidin-4-yl]-phenyl}-benzamide (168);
[6-(4-Aminomethyl-phenyl)-5-methyl-pyrimidin-4-yl]-(4-trifluoromethoxy-phenyl)-amine (169);
5-Bromo-N-(2-morpholin-4-yl-ethyl)-N'-(4-trifluoromethoxy-phenyl)-pyrimidine-4,6-diamine (170);
1-[5-Bromo-6-(4-trifluoromethoxy-phenylamino)-pyrimidin-4-yl]-piperidine-3-carboxylic acid amide (171);
{6-[2-(2-Morpholin-4-yl-ethylamino)-imidazol-1-yl]-pyrimidin-4-yl}-(4-trifluoromethoxy-phenyl)-amine (172);
(4-Trifluoromethoxy-phenyl)-{6-[2-(4-trifluoromethoxy-phenylamino)-imidazol-1-yl]-pyrimidin-4-yl}-amine (173);
N-(5-Cyclopropyl-1H-pyrazol-3-yl)-N'-(4-trifluoromethoxy-phenyl)-pyrimidine-4,6-diamine (174);
[6-(3-Amino-5-cyclopropyl-pyrazol-1-yl)-pyrimidin-4-yl]-(4-trifluoromethoxy-phenyl)-amine (175);
N-(4-Trifluoromethoxy-phenyl)-N'-[1-(3-trifluoromethyl-phenyl)-1H-imidazol-2-yl]-pyrimidine-4,6-diamine (176);
(6-Pyrrolo[2,3-b]pyridin-1-yl-pyrimidin-4-yl)-(4-trifluoromethoxy-phenyl)-amine (177);
[6-(1H-Pyrazol-4-yl)-pyrimidin-4-yl]-(4-trifluoromethoxy-phenyl)-amine (178);
[6-(1-Methyl-1H-pyrazol-4-yl)-pyrimidin-4-yl]-(4-trifluoromethoxy-phenyl)-amine (179);
[6-(1-Isobutyl-1H-pyrazol-4-yl)-pyrimidin-4-yl]-(4-trifluoromethoxy-phenyl)-amine (180);
[6-(1-Isobutyl-1H-pyrazol-4-yl)-5-methyl-pyrimidin-4-yl]-(4-trifluoromethoxy-phenyl)-amine (181);
(4-Trifluoromethoxy-phenyl)-[6-(1,3,5-trimethyl-1H-pyrazol-4-yl)-pyrimidin-4-yl]-amine (182);

{6-[1-(4-Methanesulfonyl-benzyl)-1H-pyrazol-4-yl]-pyrimidin-4-yl}-(4-trifluoromethoxy-phenyl)-amine (183);
[6-(1-Ethanesulfonyl-1H-pyrazol-4-yl)-pyrimidin-4-yl]-(4-trifluoromethoxy-phenyl)-amine (184);
[6-(1-Pyridin-4-ylmethyl-1H-pyrazol-4-yl)-pyrimidin-4-yl]-(4-trifluoromethoxy-phenyl)-amine (185);
N6-(2-Morpholin-4-yl-ethyl)-N6'-(4-trifluoromethoxy-phenyl)-[4,4']bipyrimidinyl-6,6'-diamine (186);
[5-Methyl-6-(1-methyl-1H-pyrazol-4-yl)-pyrimidin-4-yl]-(4-trifluoromethoxy-phenyl)-amine (187);
[6-(5-Methyl-1-phenyl-1H-pyrazol-4-yl)-pyrimidin-4-yl]-(4-trifluoromethoxy-phenyl)-amine (188);
[5-Methyl-6-(5-methyl-1-phenyl-1H-pyrazol-4-yl)-pyrimidin-4-yl]-(4-trifluoromethoxy-phenyl)-amine (189);
[6-(1H-Indol-4-yl)-pyrimidin-4-yl]-(4-trifluoromethoxy-phenyl)-amine (190);
[6-(1H-Indol-3-yl)-pyrimidin-4-yl]-(4-trifluoromethoxy-phenyl)-amine (191);
[6-(1H-Indol-5-yl)-pyrimidin-4-yl]-(4-trifluoromethoxy-phenyl)-amine (192);
4-[6-(4-Trifluoromethoxy-phenylamino)-pyrimidin-4-yl]-furan-2-carbaldehyde (193);
(6-Benzo[b]thiophen-4-yl-pyrimidin-4-yl)-(4-trifluoromethoxy-phenyl)-amine (194);
[6-(1H-Indol-4-yl)-5-methyl-pyrimidin-4-yl]-(4-trifluoromethoxy-phenyl)-amine (195);
(6-Dibenzofuran-4-yl-pyrimidin-4-yl)-(4-trifluoromethoxy-phenyl)-amine (196);
[6-(1-Benzyl-1H-pyrazol-4-yl)-pyrimidin-4-yl]-(4-trifluoromethoxy-phenyl)-amine (197);
[6-(1-Benzyl-1H-pyrazol-4-yl)-5-methyl-pyrimidin-4-yl]-(4-trifluoromethoxy-phenyl)-amine (198);
N6,N6'-Bis-(4-trifluoromethoxy-phenyl)-[4,4']bipyrimidinyl-6,6'-diamine (199);
N6-(2-Morpholin-4-yl-ethyl)-N6'-(4-trifluoromethoxy-phenyl)-[4,4']bipyrimidinyl-6,6'-diamine (200);
N-(4-Methyl-3-{1-[6-(4-trifluoromethoxy-phenylamino)-pyrimidin-4-yl]-1H-imidazol-2-ylamino}-phenyl)-benzamide (201);
N-(4-Methyl-3-{1-[6-(4-trifluoromethoxy-phenylamino)-pyrimidin-4-yl]-1H-imidazol-2-ylamino}-phenyl)-4-morpholin-4-ylmethyl-3-trifluoromethyl-benzamide (202);
[6-(1-Pyridin-3-ylmethyl-1H-pyrazol-4-yl)-pyrimidin-4-yl]-(4-trifluoromethoxy-phenyl)-amine (203);
[6-(1H-Pyrrolo[2,3-b]pyridin-4-yl)-pyrimidin-4-yl]-(4-trifluoromethoxy-phenyl)-amine (204);
4-[6-(4-Trifluoromethoxy-phenylamino)-pyrimidin-4-yl]-1H-pyridin-2-one (205);
[6-(2-Methyl-thiazol-4-yl)-pyrimidin-4-yl]-(4-trifluoromethoxy-phenyl)-amine (206);
2-Fluoro-5-[6-(4-trifluoromethoxy-phenylamino)-pyrimidin-4-yl]-benzaldehyde (207);
{6-[2-(4-Methyl-piperazin-1-yl)-pyridin-4-yl]-pyrimidin-4-yl}-(4-trifluoromethoxy-phenyl)-amine (208);

TABLE 8

Compounds of formula IX.

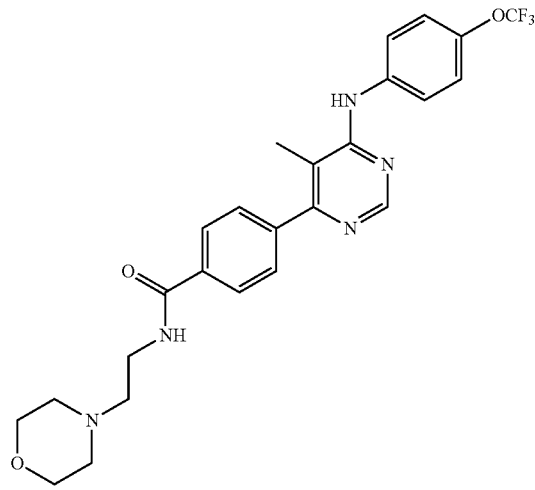 [SMILES: Cc1c(Nc2ccc(OC(F)(F)F)cc2)ncnc1-c1ccc(C(=O)NCCN2CCOCC2)cc1]

(133)

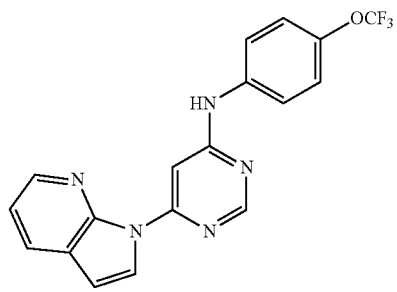 [SMILES: FC(F)(F)Oc1ccc(Nc2cc(-n3ccc4cccnc43)ncn2)cc1]

(134)

TABLE 8-continued
Compounds of formula IX.
(135)
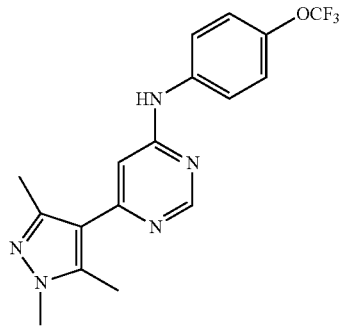 [SMILES: Cc1nn(C)c(C)c1-c1cc(Nc2ccc(OC(F)(F)F)cc2)ncn1]
(136)
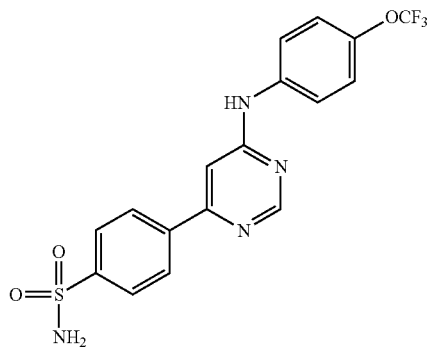 [SMILES: NS(=O)(=O)c1ccc(-c2cc(Nc3ccc(OC(F)(F)F)cc3)ncn2)cc1]
(137)
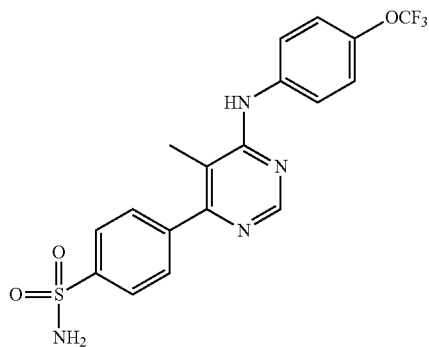 [SMILES: Cc1c(Nc2ccc(OC(F)(F)F)cc2)ncnc1-c1ccc(S(N)(=O)=O)cc1]
(138)
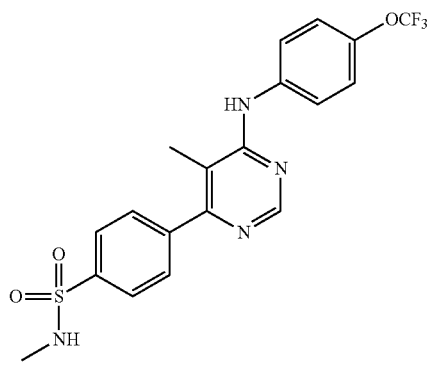

TABLE 8-continued
Compounds of formula IX.
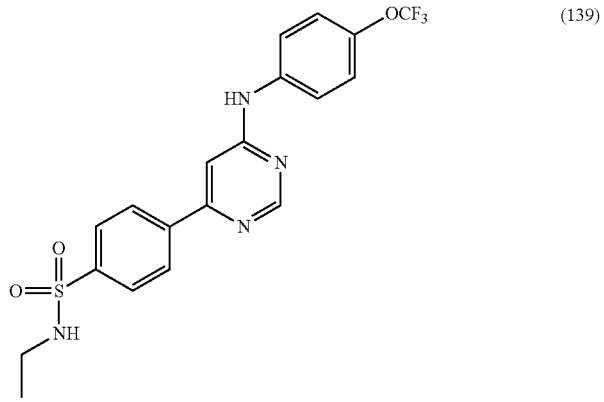 (139)
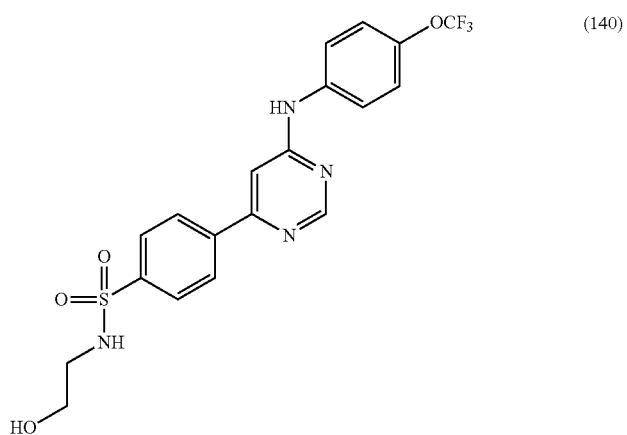 (140)
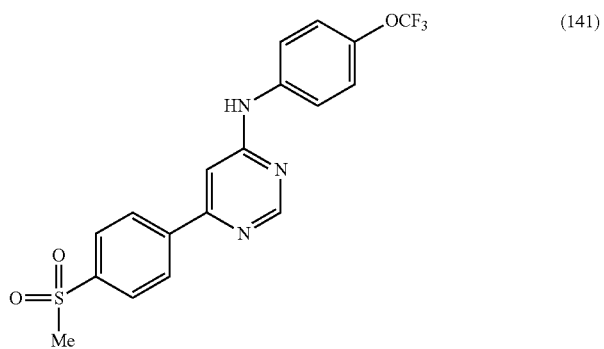 (141)
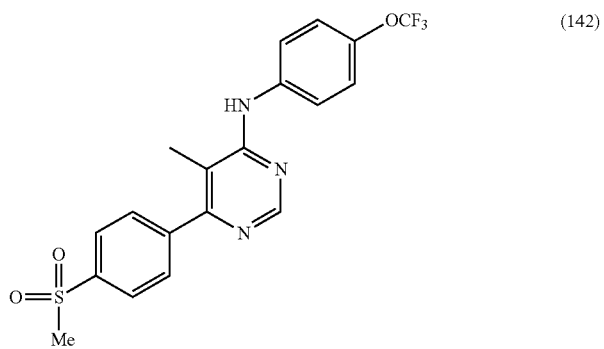 (142)

TABLE 8-continued
Compounds of formula IX.
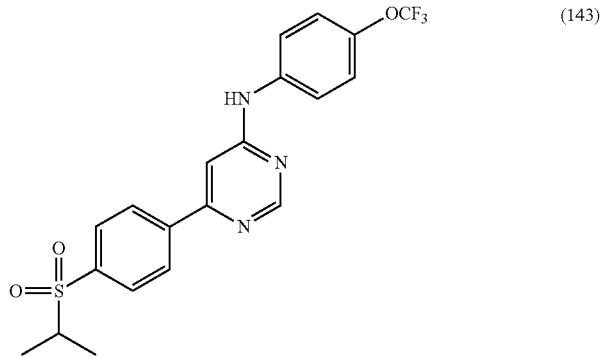
(143)
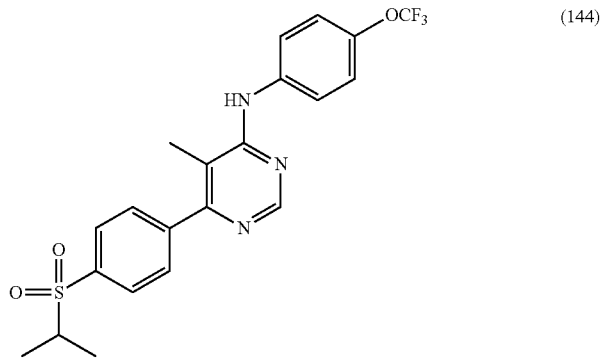
(144)
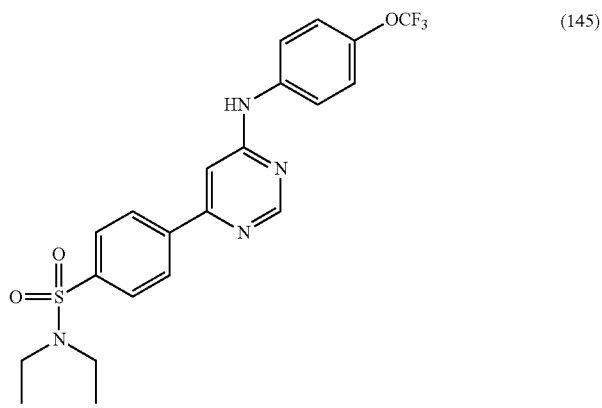
(145)
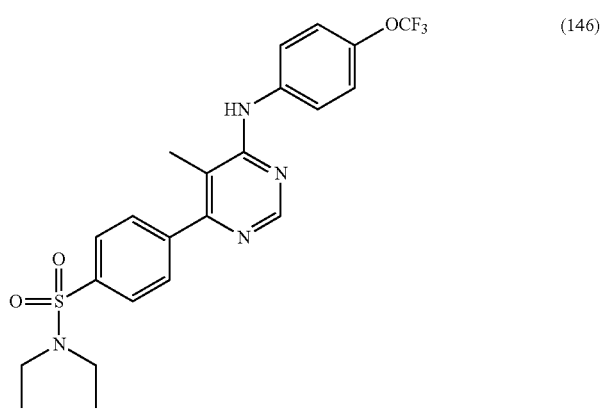
(146)

TABLE 8-continued
Compounds of formula IX.
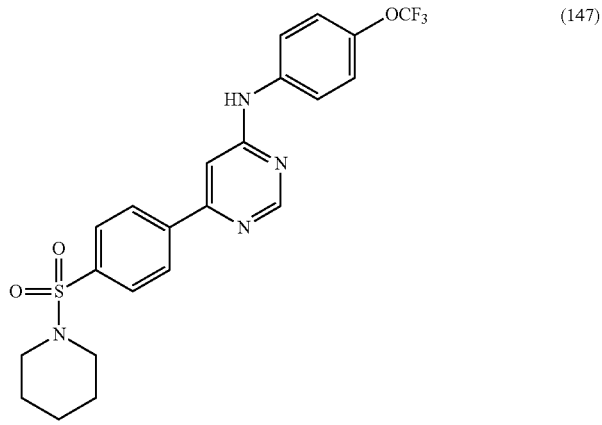 (147)
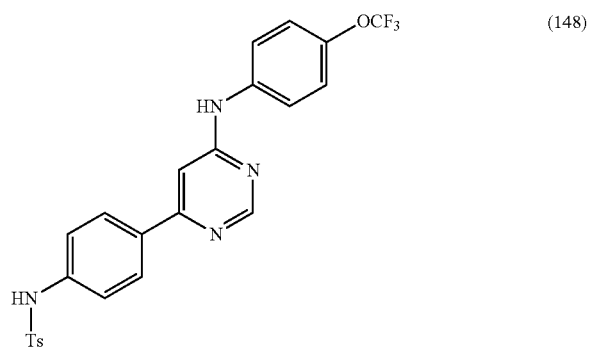 (148)
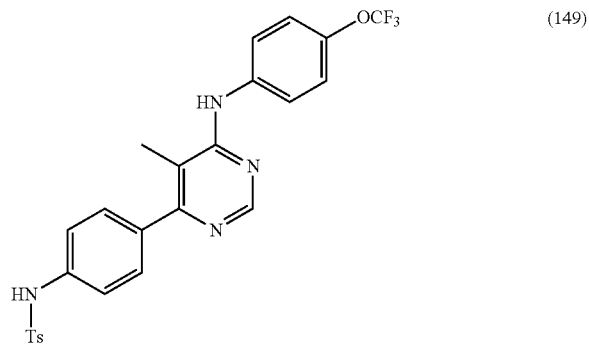 (149)
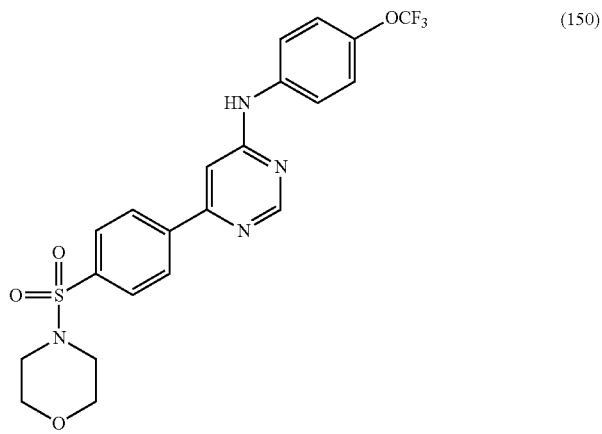 (150)

TABLE 8-continued
Compounds of formula IX.
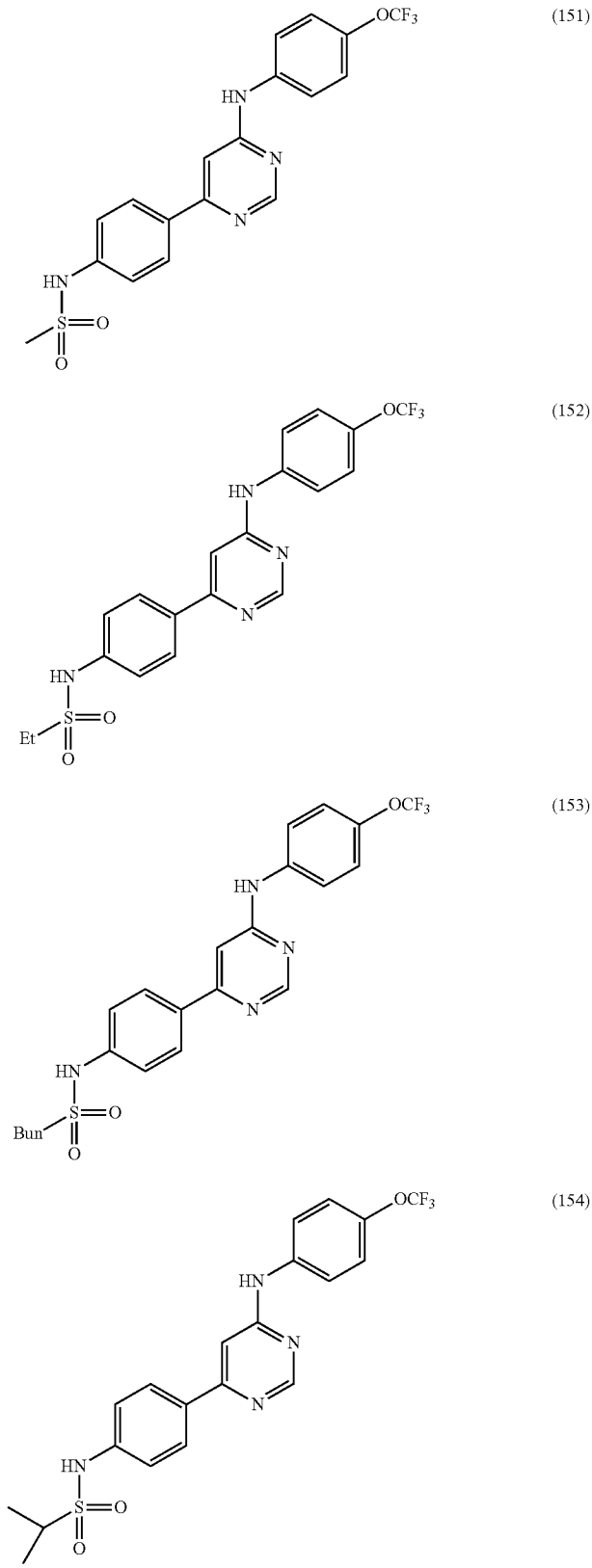
(151)
(152)
(153)
(154)

TABLE 8-continued
Compounds of formula IX.
(155)
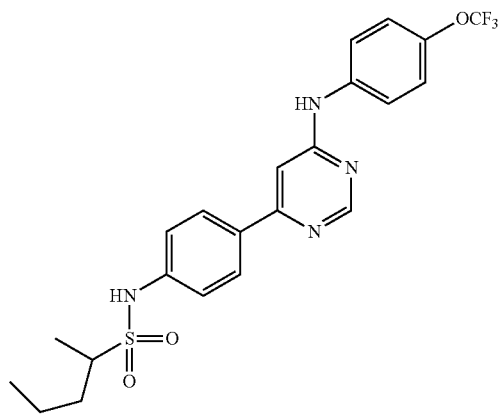 [SMILES: CCCC(C)S(=O)(=O)Nc1ccc(-c2cc(Nc3ccc(OC(F)(F)F)cc3)ncn2)cc1]
(156)
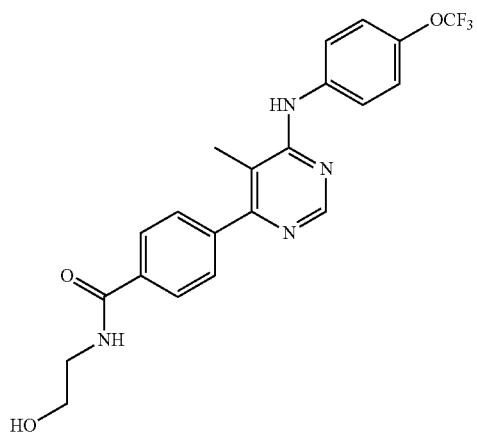 [SMILES: Cc1c(Nc2ccc(OC(F)(F)F)cc2)ncnc1-c1ccc(C(=O)NCCO)cc1]
(157)
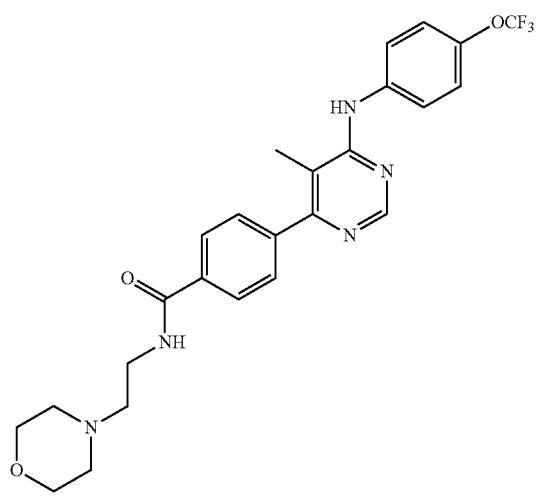 [SMILES: Cc1c(Nc2ccc(OC(F)(F)F)cc2)ncnc1-c1ccc(C(=O)NCCN2CCOCC2)cc1]

TABLE 8-continued
Compounds of formula IX.
(158)
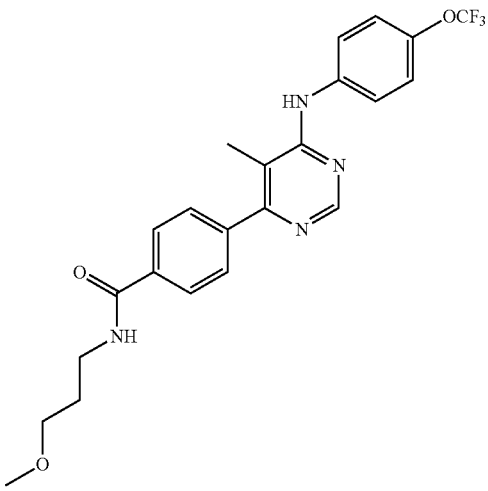 [SMILES: COCCCNC(=O)c1ccc(-c2ncnc(Nc3ccc(OC(F)(F)F)cc3)c2C)cc1]
(159)
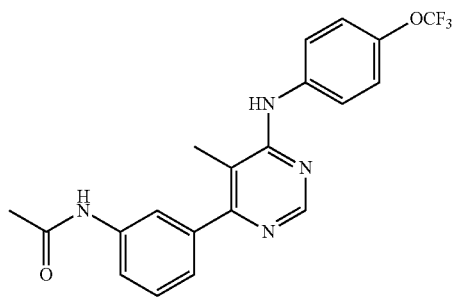 [SMILES: CC(=O)Nc1cccc(-c2ncnc(Nc3ccc(OC(F)(F)F)cc3)c2C)c1]
(160)
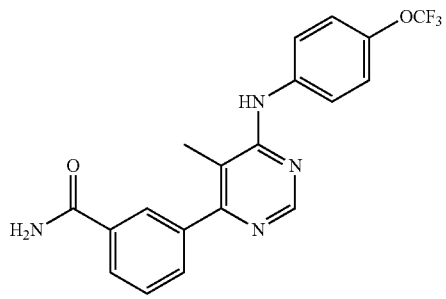 [SMILES: Cc1c(Nc2ccc(OC(F)(F)F)cc2)ncnc1-c1cccc(C(N)=O)c1]
(161)
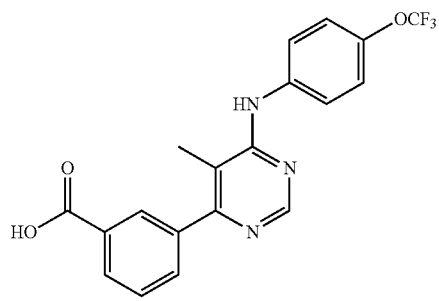 [SMILES: Cc1c(Nc2ccc(OC(F)(F)F)cc2)ncnc1-c1cccc(C(=O)O)c1]

TABLE 8-continued
Compounds of formula IX.
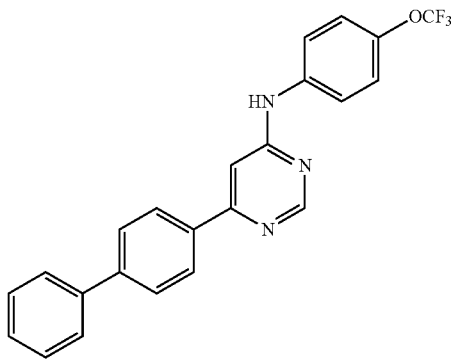 [SMILES: FC(F)(F)Oc1ccc(Nc2cc(-c3ccc(-c4ccccc4)cc3)ncn2)cc1]
(162)
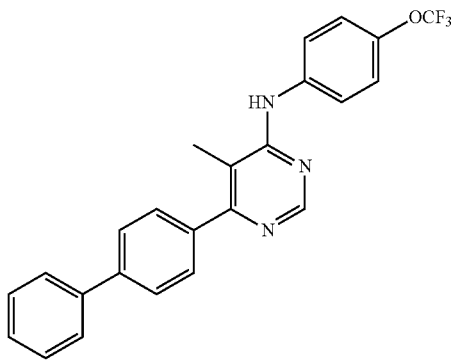 [SMILES: Cc1c(Nc2ccc(OC(F)(F)F)cc2)ncnc1-c1ccc(-c2ccccc2)cc1]
(163)
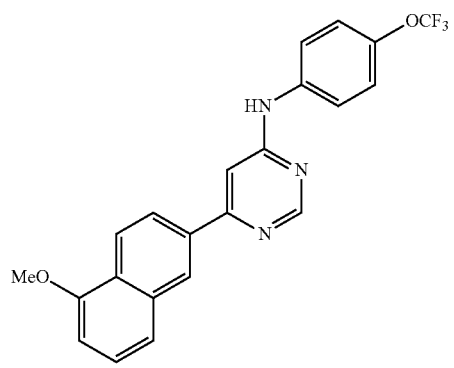 [SMILES: COc1cccc2cc(-c3cc(Nc4ccc(OC(F)(F)F)cc4)ncn3)ccc12]
(164)
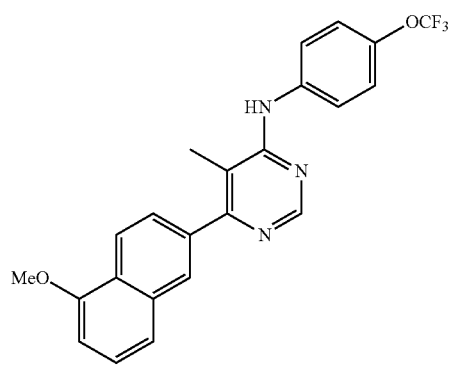 [SMILES: COc1cccc2cc(-c3ncnc(Nc4ccc(OC(F)(F)F)cc4)c3C)ccc12]
(165)

TABLE 8-continued
Compounds of formula IX.
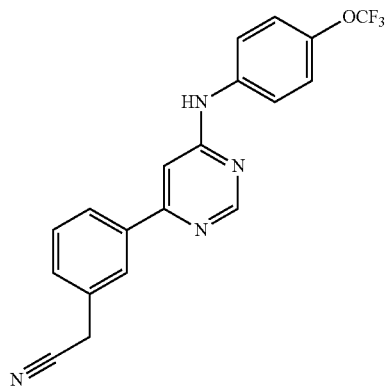 [SMILES: N#CCc1cccc(-c2cc(Nc3ccc(OC(F)(F)F)cc3)ncn2)c1]
(166)
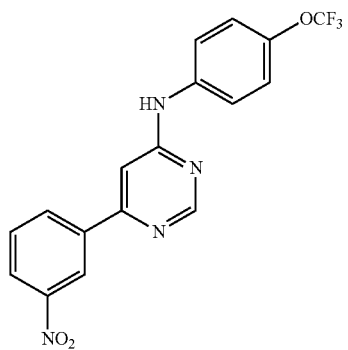 [SMILES: O=[N+]([O-])c1cccc(-c2cc(Nc3ccc(OC(F)(F)F)cc3)ncn2)c1]
(167)
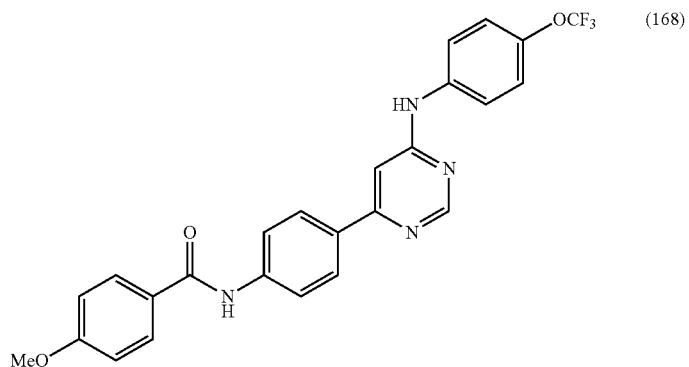
(168)
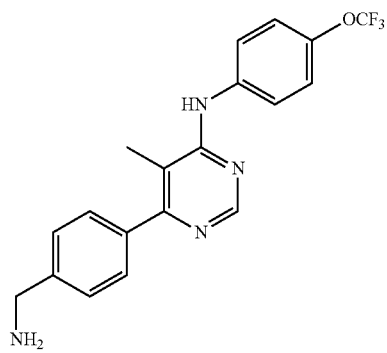 [SMILES: Cc1c(Nc2ccc(OC(F)(F)F)cc2)ncnc1-c1ccc(CN)cc1]
(169)

TABLE 8-continued
Compounds of formula IX.
(170)
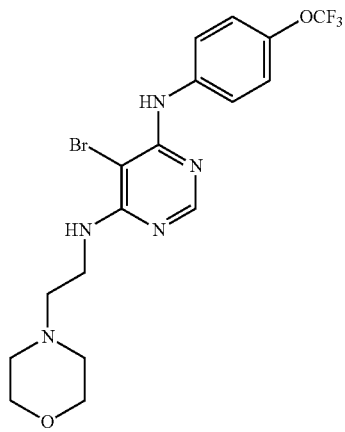 [SMILES: FC(F)(F)Oc1ccc(Nc2ncnc(NCCN3CCOCC3)c2Br)cc1]
(171)
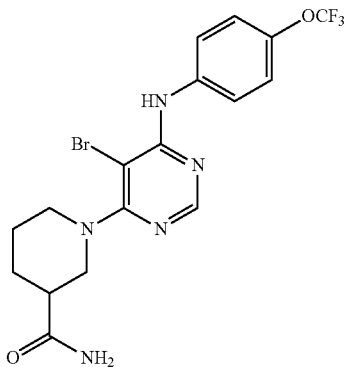 [SMILES: NC(=O)C1CCCN(c2ncnc(Nc3ccc(OC(F)(F)F)cc3)c2Br)C1]
(172)
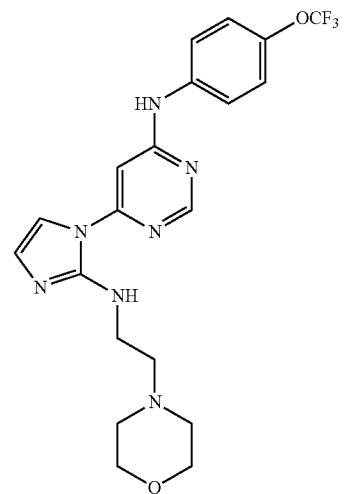 [SMILES: FC(F)(F)Oc1ccc(Nc2cc(-n3ccnc3NCCN3CCOCC3)ncn2)cc1]

TABLE 8-continued
Compounds of formula IX.
(173)
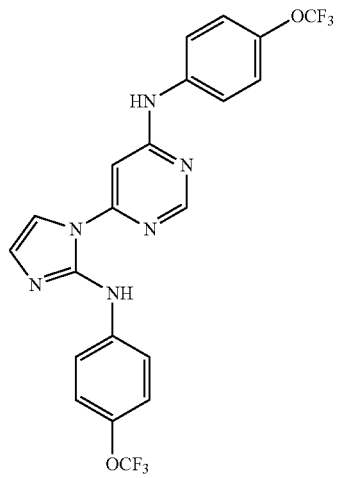 [SMILES: FC(F)(F)Oc1ccc(Nc2cc(-n3ccnc3Nc3ccc(OC(F)(F)F)cc3)ncn2)cc1]
(174)
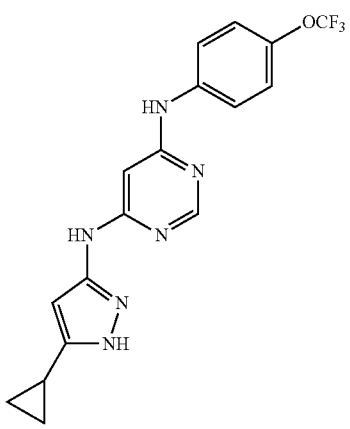 [SMILES: FC(F)(F)Oc1ccc(Nc2cc(Nc3cc(C4CC4)[nH]n3)ncn2)cc1]
(175)
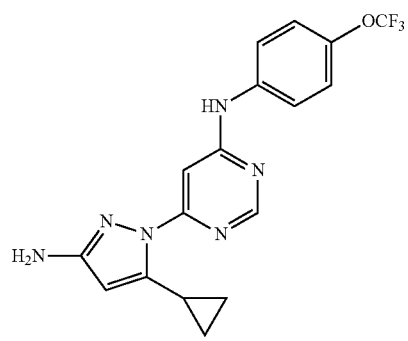 [SMILES: Nc1cc(C2CC2)n(-c2cc(Nc3ccc(OC(F)(F)F)cc3)ncn2)n1]

TABLE 8-continued
Compounds of formula IX.
(176)
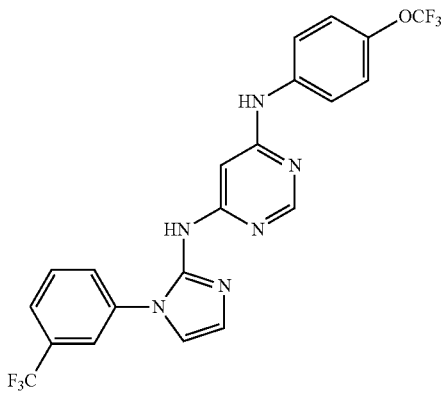 [SMILES: FC(F)(F)Oc1ccc(Nc2cc(Nc3nccn3-c3cccc(C(F)(F)F)c3)ncn2)cc1]
(177)
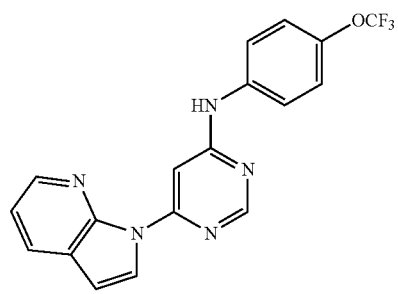 [SMILES: FC(F)(F)Oc1ccc(Nc2cc(-n3ccc4cccnc43)ncn2)cc1]
(178)
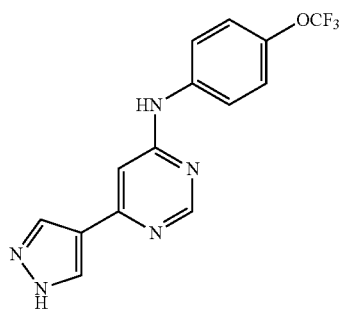 [SMILES: FC(F)(F)Oc1ccc(Nc2cc(-c3cn[nH]c3)ncn2)cc1]
(179)
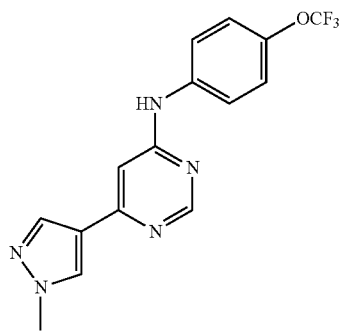 [SMILES: Cn1cc(-c2cc(Nc3ccc(OC(F)(F)F)cc3)ncn2)cn1]

83
TABLE 8-continued
Compounds of formula IX.
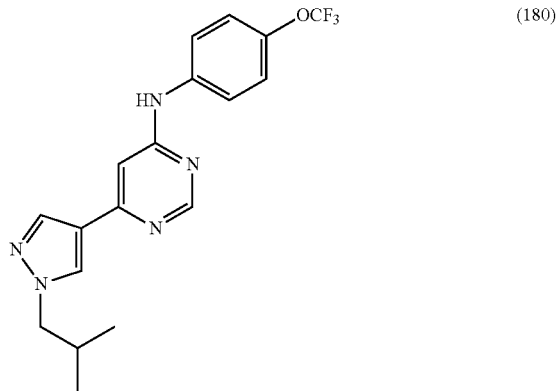 (180)
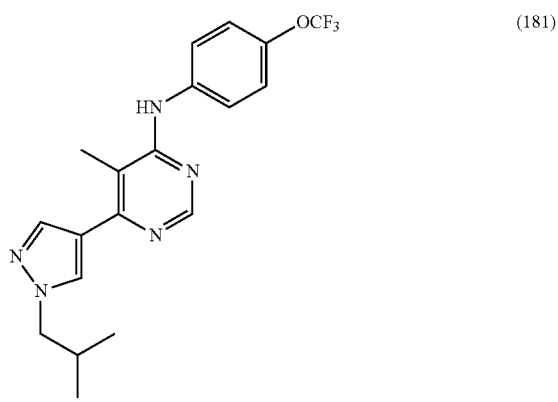 (181)
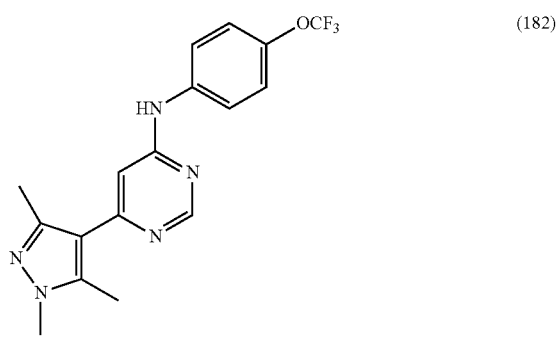 (182)
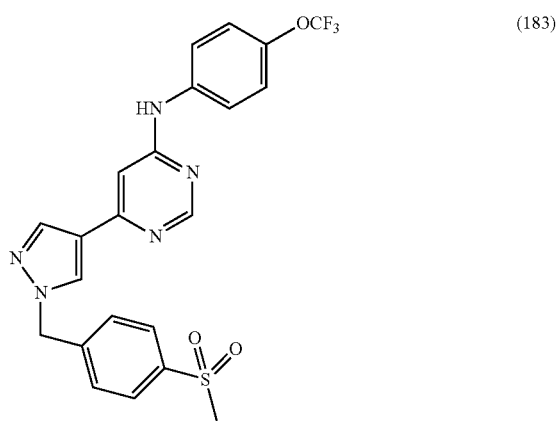 (183)
84

TABLE 8-continued
Compounds of formula IX.
(184)
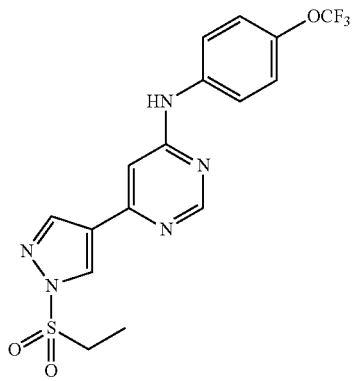 [SMILES: CCS(=O)(=O)n1cc(-c2cc(Nc3ccc(OC(F)(F)F)cc3)ncn2)cn1]
(185)
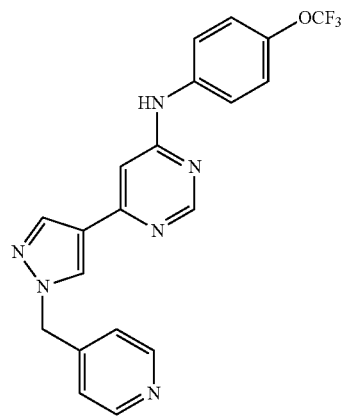 [SMILES: FC(F)(F)Oc1ccc(Nc2cc(-c3cnn(Cc4ccncc4)c3)ncn2)cc1]
(186)
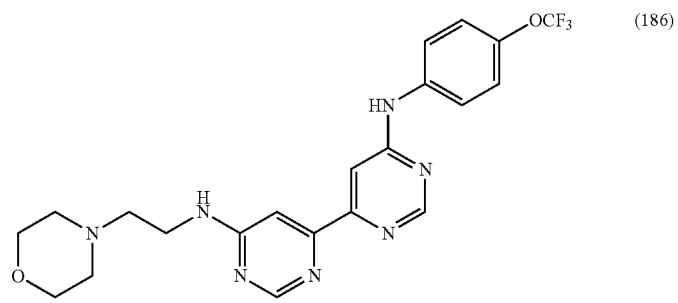
(187)
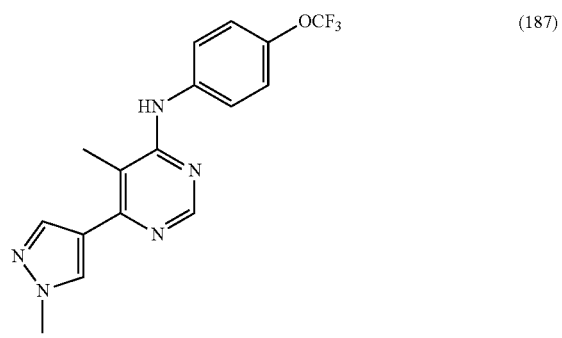

TABLE 8-continued
Compounds of formula IX.
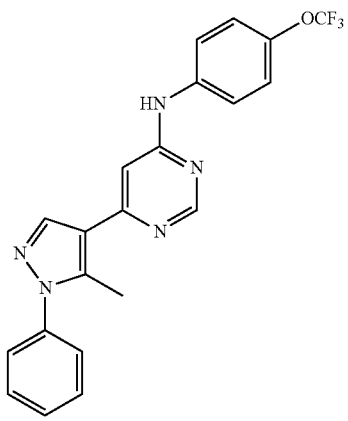 [SMILES: Cc1c(-c2cc(Nc3ccc(OC(F)(F)F)cc3)ncn2)cnn1-c1ccccc1]
(188)
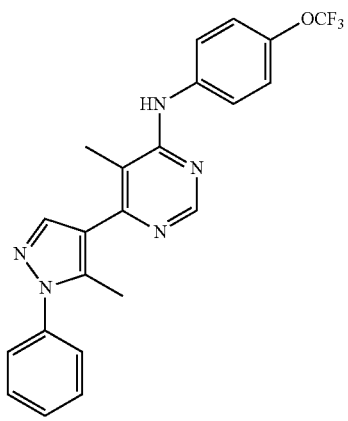 [SMILES: Cc1c(Nc2ccc(OC(F)(F)F)cc2)ncnc1-c1cnn(-c2ccccc2)c1C]
(189)
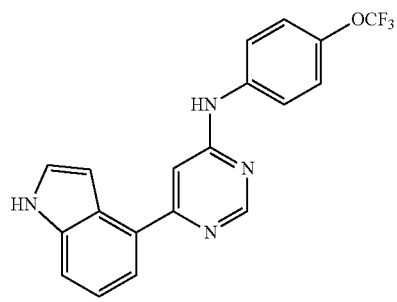
(190)
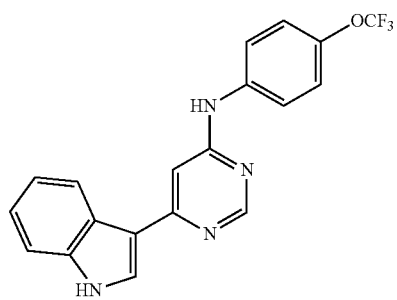 [SMILES: FC(F)(F)Oc1ccc(Nc2cc(-c3c[nH]c4ccccc34)ncn2)cc1]
(191)

TABLE 8-continued
Compounds of formula IX.
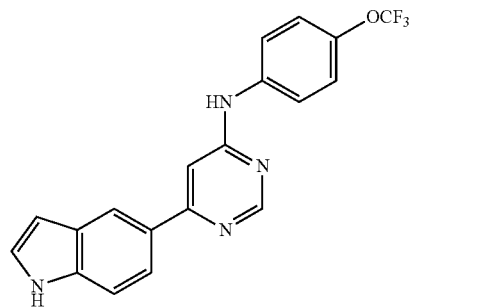 [SMILES: FC(F)(F)Oc1ccc(Nc2cc(-c3ccc4[nH]ccc4c3)ncn2)cc1] (192)
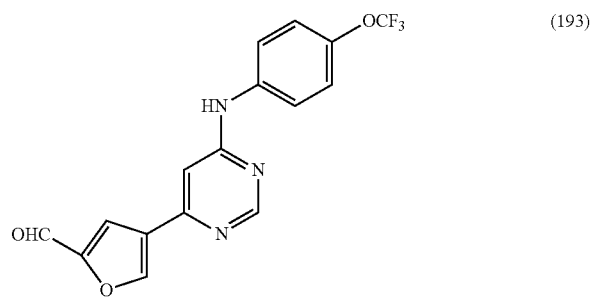 (193)
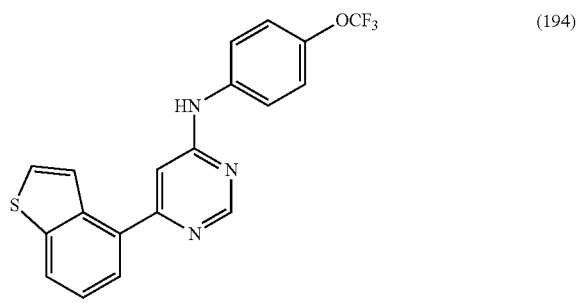 (194)
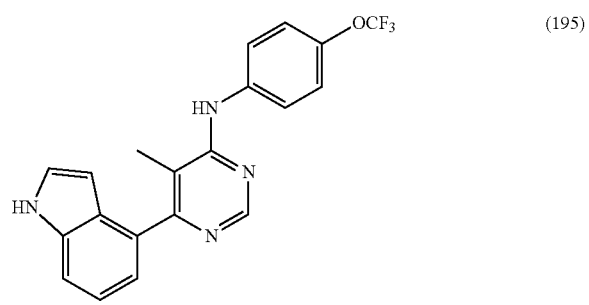 (195)
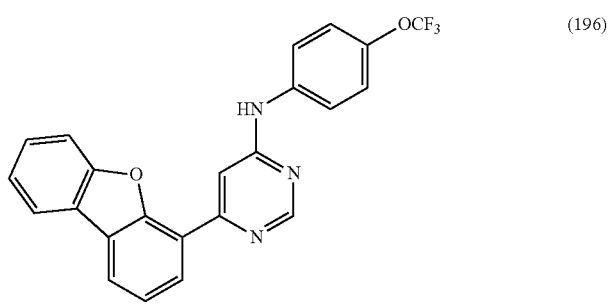 (196)

TABLE 8-continued
Compounds of formula IX.
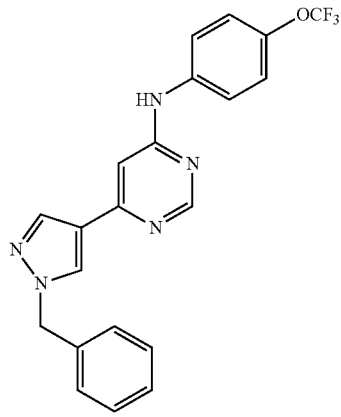 [SMILES: FC(F)(F)Oc1ccc(Nc2cc(-c3cnn(Cc4ccccc4)c3)ncn2)cc1] (197)
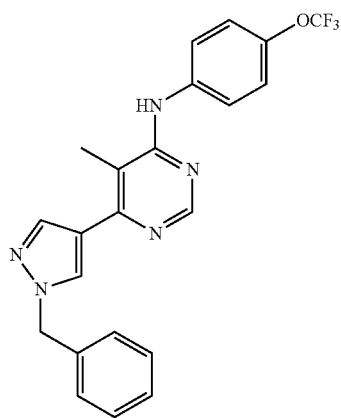 [SMILES: Cc1c(Nc2ccc(OC(F)(F)F)cc2)ncnc1-c1cnn(Cc2ccccc2)c1] (198)
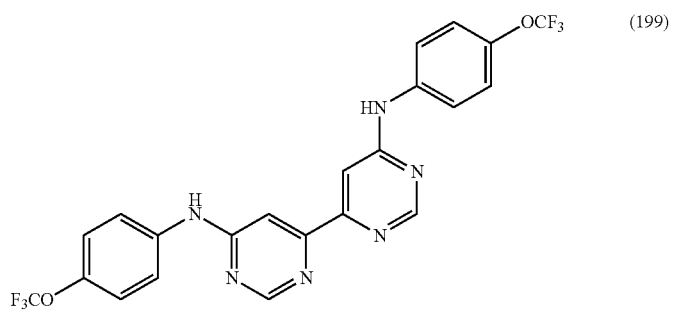 (199)
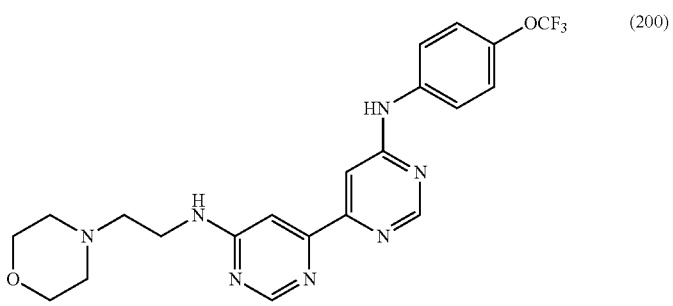 (200)

TABLE 8-continued
Compounds of formula IX.
(201)
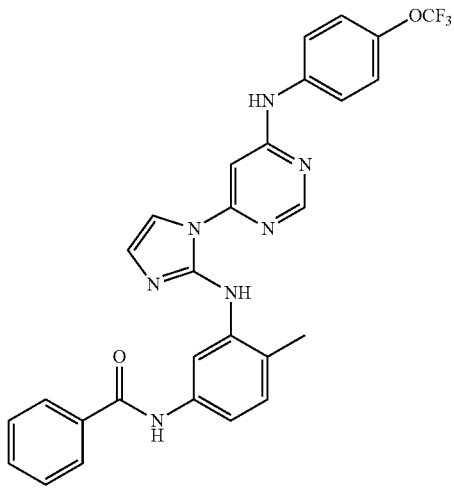 [SMILES: Cc1ccc(NC(=O)c2ccccc2)cc1Nc1nccn1-c1cc(Nc2ccc(OC(F)(F)F)cc2)ncn1]
(202)
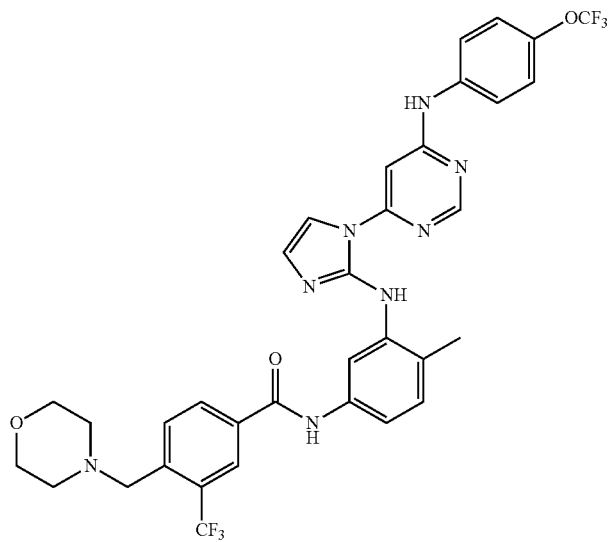 [SMILES: Cc1ccc(NC(=O)c2ccc(CN3CCOCC3)c(C(F)(F)F)c2)cc1Nc1nccn1-c1cc(Nc2ccc(OC(F)(F)F)cc2)ncn1]
(203)
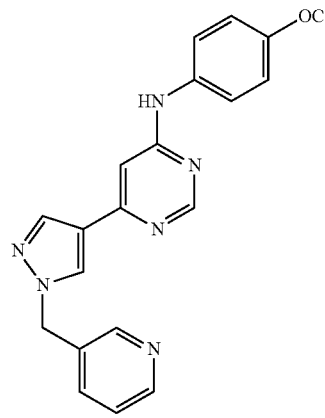

TABLE 8-continued
Compounds of formula IX.
(204)
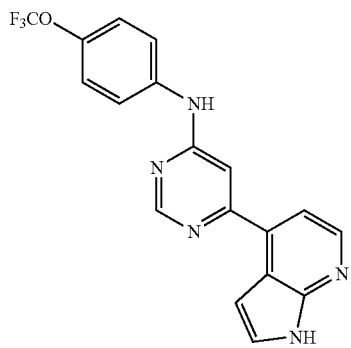 [SMILES: FC(F)(F)Oc1ccc(Nc2cc(-c3ccnc4[nH]ccc34)ncn2)cc1]
(205)
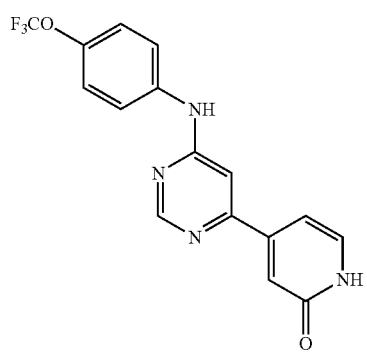 [SMILES: O=c1cc(-c2cc(Nc3ccc(OC(F)(F)F)cc3)ncn2)cc[nH]1]
(206)
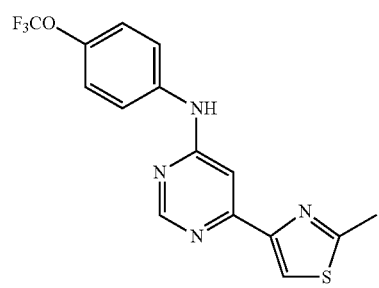 [SMILES: Cc1nc(-c2cc(Nc3ccc(OC(F)(F)F)cc3)ncn2)cs1]

TABLE 8-continued

Compounds of formula IX.

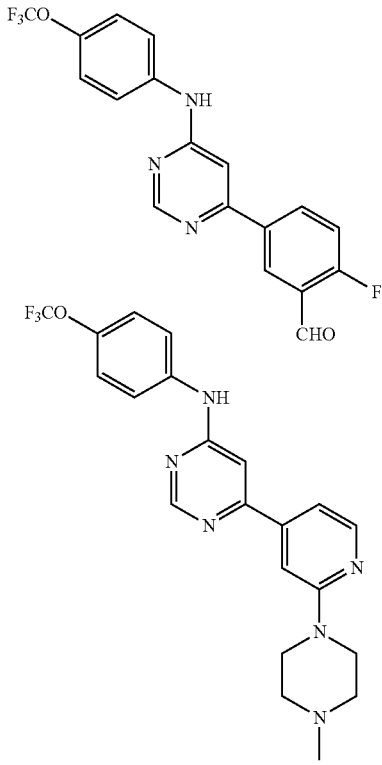

(207)

(208)

2-(3-nitrophenyl)-N-(4-(trifluoromethoxy)phenyl)imidazo[1,2-c]pyrimidin-7-amine (209);

2-Hydroxy-3-[7-(4-trifluoromethoxy-phenylamino)-imidazo[1,2-c]pyrimidin-2-yl]-benzamide (210);

TABLE 9

Compounds of formula X.

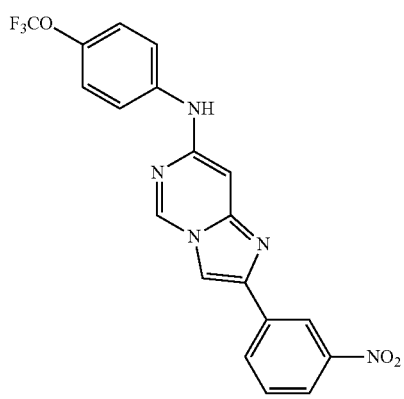 [SMILES: O=[N+]([O-])c1cccc(-c2cn3cnc(Nc4ccc(OC(F)(F)F)cc4)cc3n2)c1]

(209)

TABLE 9-continued

Compounds of formula X.

(210)

Synthesis of Compounds of the Invention

The compounds of formulae II and III were formed over a two-step reaction. First a chlorinated heteroaryl compound was coupled with a haloalkoxy substituted aniline derivative under basic conditions. The resulting compound was then treated with a hydrazine derivative to provide a mixture of compounds of formulae II and III, which were separated by chromatography (Scheme 1). Alternatively, hydrazine is added followed by addition of an electrophile under basic conditions to provide the compounds of formulae II and III.

Scheme 1

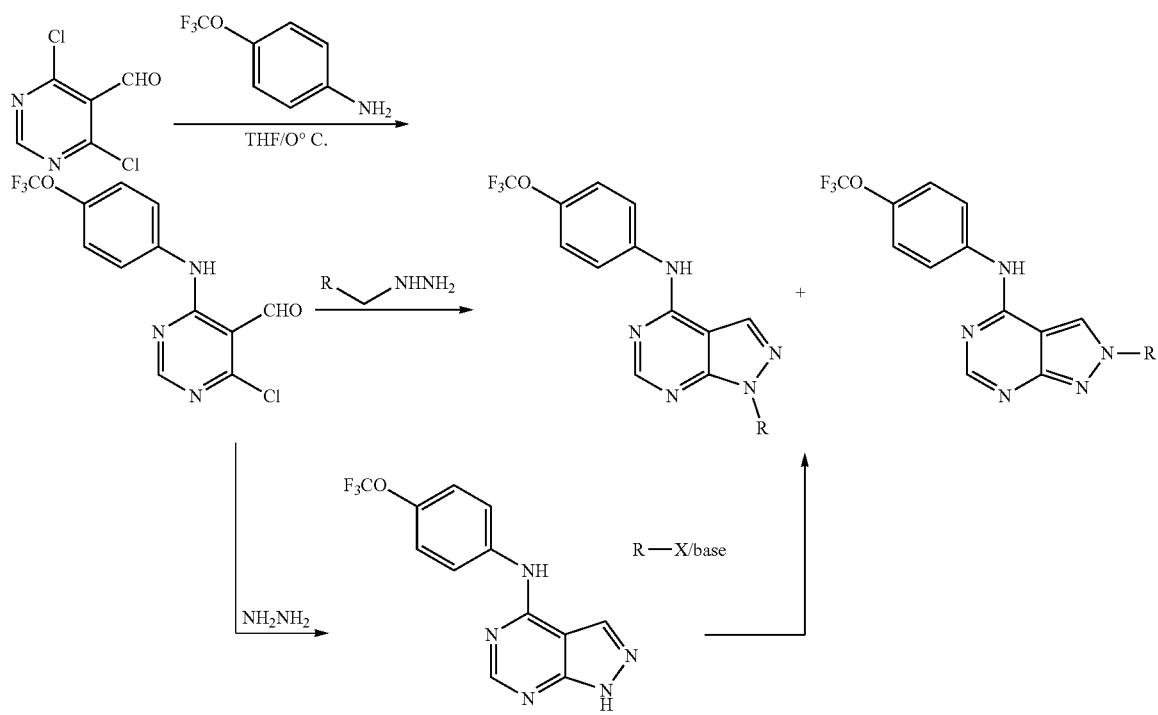

Compounds of formulae IV and V were prepared by reacting a halogenated fused bicyclic heteroaryl compound with an optionally substituted chlorinated alkyl group under basic conditions. The resulting substituted amine was coupled at the heteroaryl chloro position with an aniline derivative to provide the compounds of formulae IV or V (Scheme 2). Scheme 2 also provides for functional group modification of the side chain of the substituted amine to provide the variously substituted compounds of the invention.

-continued

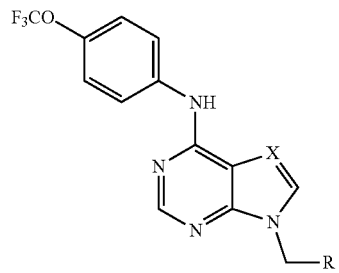

Scheme 2

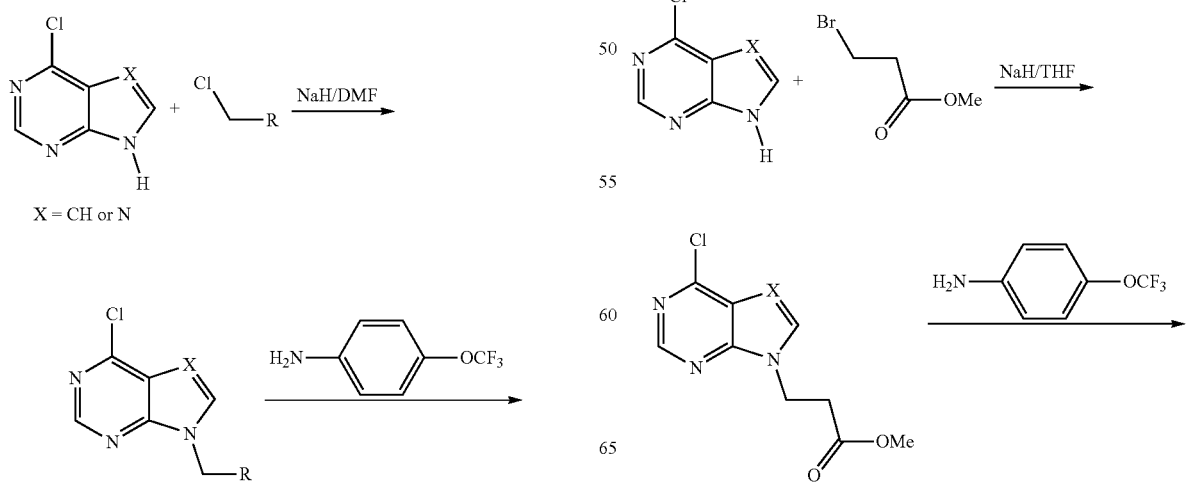

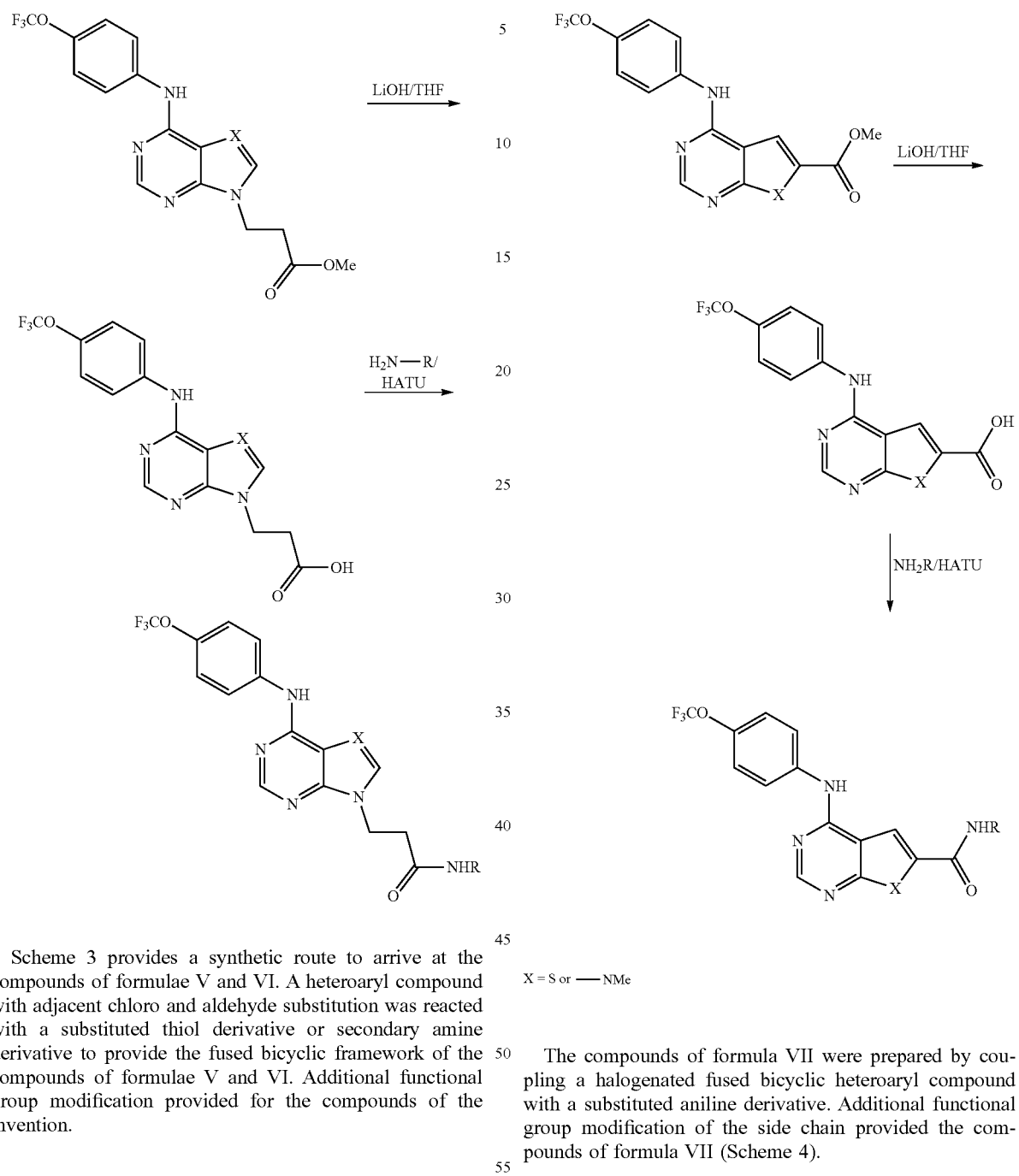

Scheme 3 provides a synthetic route to arrive at the compounds of formulae V and VI. A heteroaryl compound with adjacent chloro and aldehyde substitution was reacted with a substituted thiol derivative or secondary amine derivative to provide the fused bicyclic framework of the compounds of formulae V and VI. Additional functional group modification provided for the compounds of the invention.

X = S or —NMe

The compounds of formula VII were prepared by coupling a halogenated fused bicyclic heteroaryl compound with a substituted aniline derivative. Additional functional group modification of the side chain provided the compounds of formula VII (Scheme 4).

Scheme 3

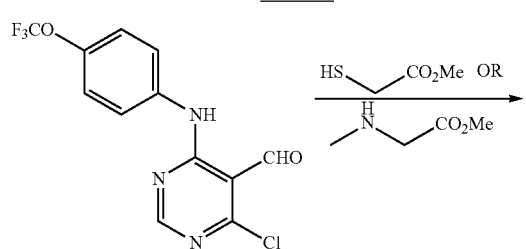

Scheme 4

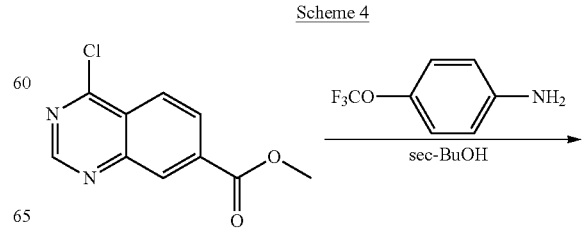

103
-continued

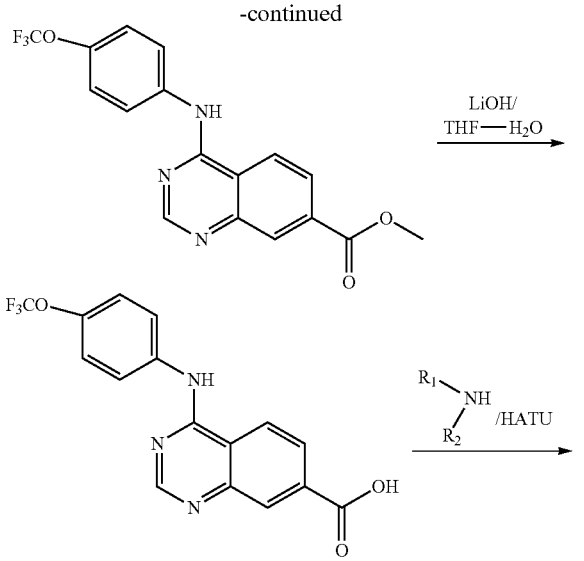

104
-continued

The compounds of formula IX were synthesized by initially coupling a dihalogenated heteroaryl compound with an aniline derivative, followed by another coupling under Mitsunobu conditions to provide the compounds of formula IX. Alternatively, in the second step, a second halo group on the heteroaryl ring is displaced by a nucleophile under basic conditions to provide a compound of formula IX (Scheme 5).

Scheme 5

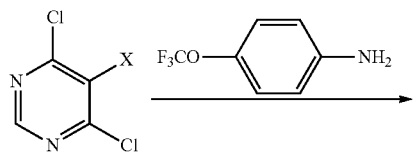

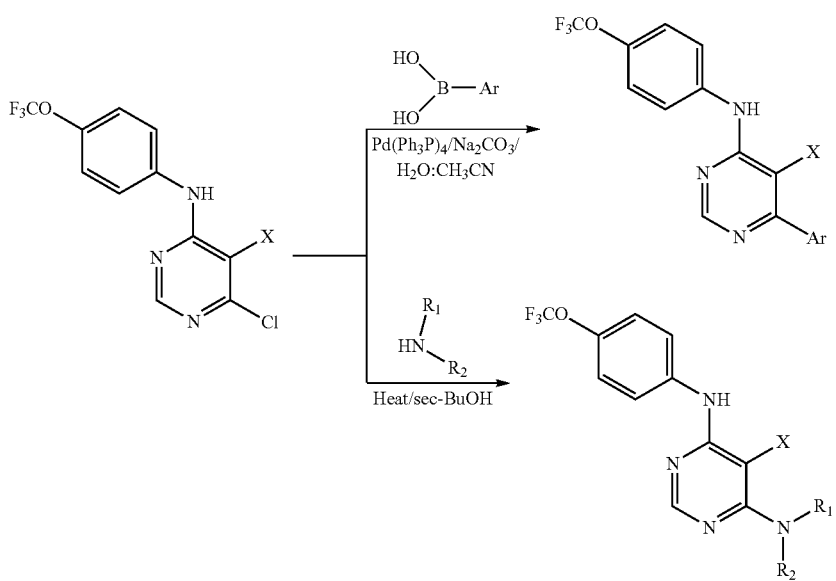

X = Me or Br

In addition to Scheme 5, compounds of formula IX were also made by reactions described in Scheme 6, wherein the product of the initial coupling is further coupled under Mitsunobu conditions to a heteroaryl group, which is then subjected to functional group modification.

Scheme 6

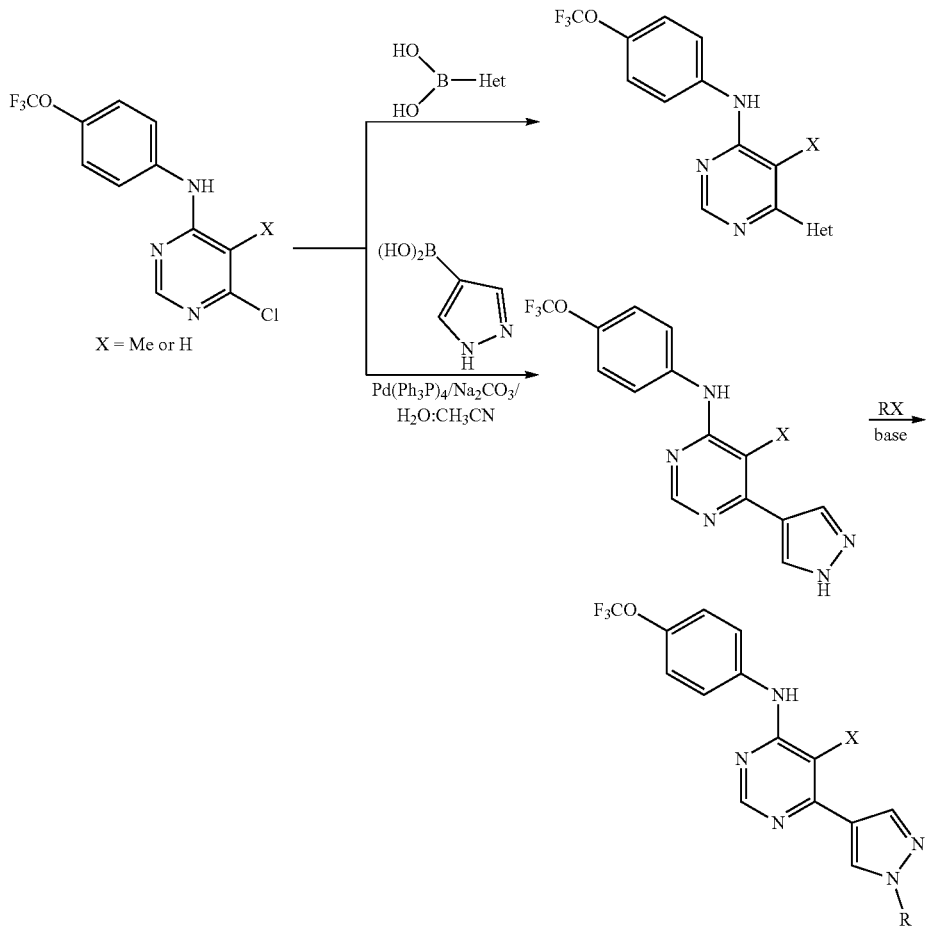

The aryl-substituted fused bicyclic compounds of formula X were synthesized according to Scheme 7. A heteroaryl compound substituted with a halo group and an amino group was reacted with an alpha halo carbonyl compound, which produced a bicyclic heteroaryl compound. Subsequent coupling with an aniline derivative providing the compound of formula X.

Scheme 7

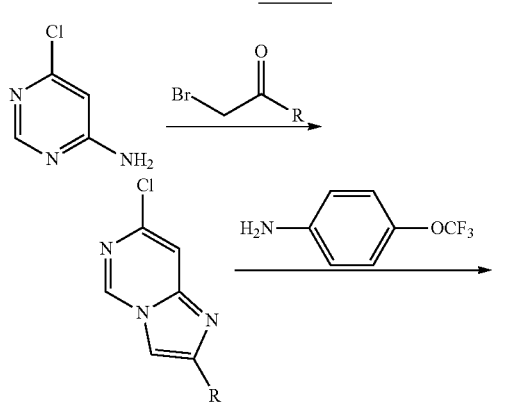

-continued

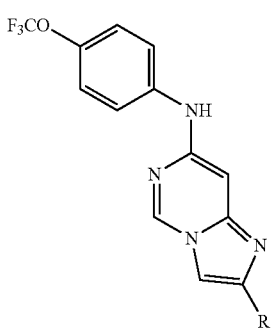

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treatment or prevention of disorders disclosed herein). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

Nucleophilic agents are known in the art and are described in the chemical texts and treatises referred to herein. The chemicals used in the aforementioned methods may include, for example, solvents, reagents, catalysts, protecting group and deprotecting group reagents and the like. The methods described above may also additionally include steps, either before or after the steps described specifically herein, to add or remove suitable protecting groups in order to ultimately allow synthesis of the compound of the formulae described herein. The methods delineated herein contemplate converting compounds of one formula to compounds of another formula. The process of converting refers to one or more chemical transformations, which can be performed in situ, or with isolation of intermediate compounds. The transformations can include reacting the starting compounds or intermediates with additional reagents using techniques and protocols known in the art, including those in the references cited herein. Intermediates can be used with or without purification (e.g., filtration, distillation, crystallization, chromatography). Other embodiments relate to the intermediate compounds delineated herein, and their use in the methods (e.g., treatment, synthesis) delineated herein.

Methods of Treatment

The compounds of the invention in free form or in pharmaceutically acceptable salt form, exhibit valuable pharmacological properties, for example, as indicated by the in vitro tests described within "Assays", infra, and are therefore indicated for therapy of diseases and disorders associated with Bcr-abl activity. For Bcr-abl, compounds of the invention preferably show an $IC_{50}$ in the range of $1\times10^{-10}$ to $1\times10^{-5}$ M, preferably less than 1 μM for wild-type Bcr-abl and at least two other Bcr-abl mutants (mutants selected from G250E, E255V, T315I, F317L and M351T).

The invention also provides a method for preventing or treating diseases or conditions comprising abnormal cell growth in a subject, including a human, comprising administering to the subject a compound of the invention in an amount effective to inhibit PDGF-R, c-Kit and/or Bcr-abl activity.

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis.

Compounds of the invention can inhibit PDGF-R and are, therefore, also suitable for the treatment of tumor diseases, which are delineated infra.

The compounds of the present invention also inhibit cellular processes involving stem-cell factor (SCF, also known as the c-kit ligand or steel factor), such as SCF receptor (kit) autophosphorylation and the SCF-stimulated activation of MAPK kinase (mitogen-activated protein kinase). The compounds of the present invention thus inhibit also the autophosphorylation of SCF receptor (and c-kit, a proto-oncogene). M07e cells are a human promegakaryocytic leukemia cell line, which depends on SCF for proliferation. A compound of the invention inhibits the autophosphorylationof SCF-R in the micromolar range.

Also abl kinase, especially v-abl kinase, is inhibited by compounds of the present invention. By analogy, the compounds of the present invention also inhibit Bcr-abl kinase and are thus suitable for the treatment of Bcr-abl-positive cancer and tumor diseases, such as leukemias (especially chronic myeloid leukemia and acutelymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

Furthermore, the present invention provides a method for inhibiting Bcr-abl activity, the method comprising contacting Bcr-abl with a compound of the invention that binds to a myristoyl binding pocket of Bcr-abl.

In addition, the compounds of the present invention can be used in combination with other anti-tumor agents.

Treatment of Diseases

The term "tumor" is used to describe an abnormal growth in tissue which occurs when cellular proliferation is more rapid than normal tissue and continues to grow after the stimuli that initiated the new growth cease. Tumors generally exhibit partial or complete lack of structural organization and functional coordination with the normal tissue, and usually form a distinct mass of tissue which may be benign (benign tumor) or malignant (carcinoma). Tumors tend to be highly vascularized.

The term "cancer" is used as a general term herein to describe malignant tumors or carcinoma. These malignant tumors may invade surrounding tissues, may metastasize to several sites and are likely to recur after attempted removal and to cause death of the patient unless adequately treated. As used herein, the terms carcinoma and cancer are subsumed under the term tumor.

Diseases or disorders treated, ameliorated or prevented by the instant invention include the following: sarcomas, neoplasia, internal malignancies such as eye or ocular cancer, rectal cancer, colon cancer, cervical cancer, prostate cancer, breast cancer and bladder cancer, benign and malignant tumors, including various cancers such as, anal and oral cancers, stomach, rectal, liver, pancreatic, lung, cervix uteri, corpus uteri, ovary, prostate, testis, renal, mouth/pharynx, esophageal, larynx, kidney, brain/cns (e.g., gliomas), head and neck, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, lymphoma, neurofibromatosis, tuberous sclerosis (each of which conditions produces benign tumors of the skin), hemangiomas, lymphangiogenesis, rhabdomyosarcomas, retinoblastoma, osteosarcoma, acoustic neuroma, neurofibroma, trachoma, pyogenic granulomas, blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen, psoriasis, acne, rosacea, warts, eczema, neurofibromatosis, Sturge-Weber syndrome, venous ulcers of the skin, tuberous sclerosis, chronic inflammatory disease, arthritis, lupus, scleroderma, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium, keratitis sicca, Sjogren's, phylectenulosis, syphilis, Mycobacteria infections, lipid degeneration, chemical burns, bacterial ulcers, fungal ulcers, herpes simplex infections, herpes zoster infections, protozoan infections, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, corneal graft rejection, diabetic retinopathy, macular edema, macular degeneration, sickle cell anemia, sarcoid, pseudoxanthoma elasticum, Paget's disease, vein occlusion, artery occlusion, carotid obstructive disease, chronic uveitis/vitritis, Lyme disease, systemic lupus erythematosus, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma, post-laser complications, rubeosis (neovascularization of the ankle), diseases caused by the abnormal proliferation of fibrovascular or fibrous tissue including all forms of proliferative vitreoretinopathy, whether or not associated with diabetes, neovascular disease, pannus, diabetic macular edema, vascular retinopathy, retinal degeneration, inflammatory diseases of the retina, proliferative vitreoretinopathy, diseases associated with rubeosis (neovascularization of the ankle), diseases caused by the abnormal proliferation of fibrovascular or fibrous tissue including all forms of proliferative vitreoretinopathy, Crohn's disease and ulcerative colitis, sarcoidosis, osteoarthritis, inflammatory bowel diseases, skin lesions, Osler-Weber-Rendu disease, or hereditary hemorrhagic telangiectasia, osteoarthritis, Sarcoidosis, skin lesions, acquired immune deficiency syndrome, and small bowel obstruction.

In a particular embodiment, the inhibition of the kinase activity of Bcr-abl is an important aspect of the present invention. More particularly, the present invention relates to methods for treating cancers, including Chronic Myelogenous Leukemia, comprising exposing the cancer to an inhibitory or therapeutically effective amount or concentration of at least one of the disclosed compounds. This method may be used therapeutically, in comparison tests such as assays for determining the activities of related analogs as well as for determining the susceptibility of a patient's cancer to one or more of the compounds according to the present invention.

Kinase inhibiting compounds of the present invention are used to treat, ameliorate or prevent, among others, benign and malignant tumors, including various cancers such as, Chronic Myelogenous Leukemia, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others. In addition, conditions such as neurofibromatosis, tuberous sclerosis (each of which conditions produces benign tumors of the skin), hemangiomas and lymphangiogenesis, among others, may be treated effectively with compounds according to the present invention.

The compounds of the invention are useful in treating non-malignant proliferative disorders, such as atherosclerosis, thrombosis, psoriasis, scleroderma, and fibrosis, as well as for the protection of stem cells, for example to combat the hemotoxic effect of chemotherapeutic agents, such as 5-fluoruracil, and in asthma. It can especially be used for the treatment of diseases, which respond to an inhibition of the PDGF-R kinase.

Methods for treating, ameliorating, or preventing skin disorders such as psoriasis, acne, rosacea, warts, eczema, hemangiomas, lymphangiogenesis, neurofibromatosis, Sturge-Weber syndrome, venous ulcers of the skin, tuberous sclerosis, chronic inflammatory disease and arthritis, as well as inflammation such as chronic inflammatory disease, including arthritis, lupus and scleroderma are also contemplated by the present invention, such methods comprising administering a therapeutically effective amount of one or more of the disclosed compounds to a subject in need of such treatment.

Diseases associated with neovascularization include optic disc neovascularization, iris neovascularization, retinal neovascularization, choroidal neovascularization, corneal neovascularization, and intravitreal neovascularization.

Diseases associated with corneal neovascularization and retinal/choroidal neovascularization that can be treated, ameliorated, or prevented, according to the present invention include but are not limited to, diabetic retinopathy, retinopathy of prematurity, corneal graft rejection, neovascular glaucoma and retrolental fibroplasias, epidemic keratoconjunctivitis, vitamin A deficiency, contact lens overwear, atopic keratitis, superior limbic keratitis, pterygium keratitis sicca, Sjogren's, acne rosacea, phylectenulosis, syphilis, Mycobacteria infections, lipid degeneration, chemical burns, bacterial ulcers, fungal ulcers, herpes simplex infections, herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, macular edema, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme disease, systemic lupus erythematosus, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovascularization of the ankle), diseases caused by the abnormal proliferation of fibrovascular or fibrous tissue including all forms of proliferative vitreoretinopathy, whether or not associated with diabetes, and corneal graft rejection.

Diseases associated with chronic inflammation and arthritis can be treated, ameliorated or prevented by the compositions and methods of the present invention. Diseases with symptoms of chronic inflammation include inflammatory bowel diseases such as Crohn's disease and ulcerative colitis, psoriasis, sarcoidosis, rheumatoid arthritis, osteoarthritis, lupus and scleroderma.

In addition, the compounds of the present invention show useful effects in the treatment of disorders arising as a result of transplantation, for example, allogenic transplantation, especially tissue rejection, such as especially obliterative bronchiolitis (OB), i.e., a chronic rejection of allogenic lung transplants. In contrast to patients without OB, those with OB often show an elevated PDGF concentration in bronchoalveolar lavage fluids. Synergistic effects with other immunomodulatory or anti-inflammatory substances are possible, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41 g.

The compounds of the present invention are also effective in diseases associated with vascular smooth-muscle cell migration and proliferation (where PDGF and PDGF-R often also play a role), such as restenosis and atherosclerosis.

Pharmaceutical Compositions

Pharmaceutical compositions and dosage forms of the invention comprise one or more of the active ingredients disclosed herein. Pharmaceutical compositions and dosage forms of the invention typically also comprise one or more pharmaceutically acceptable excipients or diluents.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient.

The invention also provides compositions comprising an effective amount of a composition containing a compound of the invention and an acceptable carrier. Preferably, a composition of this invention is formulated for pharmaceutical use ("a pharmaceutical composition"), wherein the carrier is a pharmaceutically acceptable carrier. The carrier(s) must be "acceptable" in the sense of being compatible with the other ingredients of the formulation and, in the case of a pharmaceutically acceptable carrier, not deleterious to the recipient thereof in amounts typically used in medicaments.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers or both, and then if necessary shaping the product.

The pharmaceutical compositions according to the invention are those suitable for enteral, such as oral or rectal, transdermal, topical, and parenteral administration to mammals, including man, to inhibit Bcr-abl activity, and for the treatment of Bcr-abl dependent disorders, and comprise an effective amount of a pharmacologically active compound of the present invention, alone or in combination, with one or more pharmaceutically acceptable carriers. More particularly, the pharmaceutical compositions comprise an effective Bcr-abl inhibiting amount of a compound of the present invention. Single unit dosage forms of the invention are suitable for oral, mucosal (e.g., nasal, sublingual, vaginal, buccal, or rectal), parenteral (e.g., subcutaneous, intravenous, bolus injection, intramuscular, intraarterial, intracutaneous, intraarticular, intrasynovial, intrasternal, intrathecal, intralesional and intracranial injection or infusion techniques), by inhalation spray, topically, rectally, nasally, buccally, vaginally, via an implanted reservoir, or transdermal administration to a patient.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disorder may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents.

If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A heterocyclic compound of this invention can also be administered in the form of suppositories for rectal administration.

If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

Preferred are tablets and gelatin capsules comprising the active ingredient together with a) diluents, e. g., lactose, dextrose, sucrose, mannitol, sorbitol, cellulose and/or glycine; b) lubricants, e. g., silica, talcum, stearic acid, its magnesium or calcium salt and/or polyethyleneglycol; for tablets also c) binders, e. g., magnesium aluminum silicate, starch paste, gelatin, tragacanth, methylcellulose, sodium carboxymethylcellulose and or polyvinylpyrrolidone; if desired d) disintegrants, e. g., starches, agar, alginic acid or its sodium salt, or effervescent mixtures; and/or e) absorbents, colorants, flavors and sweeteners. Tablets may be either film coated or enteric coated according to methods known in the art.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain-solubilizers, stabilizers, tonicity enhancing agents, buffers and preservatives.

The pharmaceutical formulations contain an effective Bcr-abl inhibiting amount of a compound of the present invention as defined above, either alone or in combination with another therapeutic agent. In conjunction with another active ingredient, a compound of the present invention may be administered either simultaneously, before or after the other active ingredient, either separately by the same or different route of administration or together in the same pharmaceutical formulation.

The carrier in the pharmaceutical composition must be "acceptable" in the sense of being compatible with the active ingredient of the formulation (and preferably, capable of stabilizing it) and not deleterious to the subject to be treated.

For example, solubilizing agents such as cyclodextrins, which form specific, more soluble complexes with the compounds of this invention, or one or more solubilizing agents, can be utilized as pharmaceutical excipients for delivery of the compounds of the invention. Examples of other carriers include colloidal silicon dioxide, magnesium stearate, cellulose, sodium lauryl sulfate, and D&C Yellow #10.

As used herein, the terms "animal", "subject" and "patient", include, but are not limited to, a cow, monkey, horse, sheep, pig, chicken, turkey, quail, cat, dog, mouse, rat, rabbit, guinea pig and human (preferably, a human).

The pharmacologically active compounds of the present invention are useful in the manufacture of pharmaceutical compositions comprising an effective amount thereof in conjunction or mixture with excipients or carriers suitable for either enteral, parenteral, oral, mucosal, or topical application.

The interrelationship of dosages for animals and humans (based on milligrams per meter squared of body surface) is described in Freireich et al., (1966) Cancer Chemother Rep 50: 219. Body surface area may be approximately determined from height and weight of the patient. See, e.g., Scientific Tables, Geigy Pharmaceuticals, Ardley, N.Y., 1970, 537. An effective amount of a compound of this invention can range from about 0.001 mg/kg to about 1000 mg/kg, more preferably 0.01 mg/kg to about 100 mg/kg, more preferably 0.1 mg/kg to about 10 mg/kg; or any range in which the low end of the range is any amount between 0.001 mg/kg and 900 mg/kg and the upper end of the range is any amount between 0.1 mg/kg and 1000 mg/kg (e.g., 0.005 mg/kg and 200 mg/kg, 0.5 mg/kg and 20 mg/kg). Effective doses will also vary, as recognized by those skilled in the art, depending on the diseases treated, route of administration, excipient usage, and the possibility of co-usage with other therapeutic treatments such as use of other agents.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

A compound of the invention can, for example, be administered with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Definitions

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

An "amido" is an —C(O)$NH_2$, and an "N-alkyl-substituted amido" is of the formula C(O)NHR; where a divalent "amide" group is indicated, the group is —C(O)N— or —NC(O)—.

As used herein, the term "halogen," "halo," or "hal" means —F, —Cl, —Br or —I.

As used herein, the term "haloalkyl" means an alkyl group in which one or more (including all) of the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

The term "cycloalkyl" refers to a hydrocarbon 3-8 membered monocyclic or 7-14 membered bicyclic ring system having at least one saturated ring, or hydrocarbon 3-8 membered monocyclic or 7-14 membered bicyclic ring system having at least one non-aromatic ring, wherein the non-aromatic ring has some degree of unsaturation. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, cyclodecyl, cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituents. Representative aralkyl groups include benzyl, 2-phenyl-ethyl, naphth-3-yl-methyl and the like.

As used herein, the term "alkylene" refers to an alkyl group that has two points of attachment. The term "($C_1$-$C_6$) alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH$ ($CH_3$)—), and the like.

The term "arylalkoxy" refers to an alkoxy substituted with aryl.

The term "heteroaryl" refers to a 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated), wherein at least one ring in the ring system is aromatic. Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxopyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroaralkyl" or "heteroarylalkyl" means a heteroaryl group that is attached to another group by a ($C_1$-$C_6$)alkylene. Heteroaralkyl groups may be optionally substituted, either on the heteroaryl portion of the heteroaralkyl group or on the alkylene portion of the heteroaralkyl group, with one or more substituent. Representative heteroaralkyl groups include 2-(pyridin-4-yl)-propyl, 2-(thien-3-yl)-ethyl, imidazol-4-yl-methyl and the like.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P and Si, preferably O, N, and S, wherein the nonaromatic ring system is completely saturated. The term "heterocycloalkyl" also refers to nonaromatic 5-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Bicyclic and tricyclic ring systems may be fused ring systems or spiro ring systems. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, 1,4-dioxa-8-aza-spiro[4.5]dec-8-yl, tetrahydrofuranyl, tetrahydrothienyl, thiirene, thiirenyl, thiadiazirinyl, dioxazolyl, 1,3-oxathiolyl, 1,3-dioxolyl, 1,3-dithiolyl, oxathiazinyl, dioxazinyl, dithiazinyl, oxadiazinyl, thiadiazinyl, oxazinyl, thiazinyl, 1,4-oxathiin, 1,4-dioxin, 1,4-dithiin, 1H-pyranyl, oxathiepinyl, 5H-1,4-dioxepinyl, 5H-1,4-dithiepinyl, 6H-isoxazolo[2,3-d]1,2,4-oxadiazolyl, 7aH-oxazolo[3,2-d]1,2,4-oxadiazolyl, and the like.

The term "alkylamino" refers to an amino substituent which is further substituted with one or two alkyl groups. The term "aminoalkyl" refers to an alkyl substituent which is further substituted with one or more amino groups.

The term "effective amount" is used throughout the specification to describe concentrations or amounts of compounds according to the present invention which may be used to produce a favorable change in the disease or condition treated, whether that change is a remission, a decrease in growth or size of cancer, tumor or other growth, a favorable physiological result including the clearing up of skin or tissue, or the like, depending upon the disease or condition treated.

As used herein, the terms "prevent," "preventing," "prevention," and the like refer to reducing the probability of developing a disorder or condition in a subject, who does not have, but is at risk of or susceptible to developing a disorder or condition.

The term "subject" is used throughout the specification to describe an animal, preferably a human, to whom treatment, including prophylactic treatment, with the compounds according to the present invention is provided. For treatment of those infections, conditions or disease states which are specific for a specific animal such as a human patient, the term patient refers to that specific animal. In most instances, the term patient refers to a human patient.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

The term "$IC_{50}$" is the concentration of a compound that results in 50% inhibition of activity of a peptide, protein, enzyme or biological process.

"Myristoyl Binding Pocket" is a region of Bcr-abl at which a myristoyl moiety can bind when the BCR-Abl protein is in an appropriate conformation for myristoyl binding. Myristoyl binding pockets are described in, for example, Hantschel et al., "A Myristoyl/Phosphotyrosine Switch Regulates c-Abl" Cell (2003), Vol. 112, 845-857 and Bhushan et al., "Structural Basis for the Autoinlaibition of c-Abl Tyrosine Kinase" Cell (2003), Vol. 112, 859-871.

The fusion protein Bcr-Abl is a result of a reciprocal translocation that fuses the Abl proto-oncogene with the Bcr gene. Bcr-abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly PDGF-R, c-Kit and Bcr-abl kinase related diseases.

As used herein the term "substituent" or "substituted" means that a hydrogen radical on a compound or group (such as, for example, alkyl, alkenyl, alkynyl, alkylene, aryl, aralkyl, heteroaryl, heteroaralkyl, cycloalkyl, or heterocycloalkyl group) is substituted or optionally substituted with any desired group that do not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, alkylarylamino, cyano, nitro, mercapto, thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cycloalkyl, heterocycloalkyl, wherein alkyl, alkenyl, alkyloxy, alkoxyalkyl, aryl, heteroaryl, cycloalkyl, are heterocycloalkyl are heterocycloalkyl are optionally substituted with alkyl, aryl, heteroaryl, halogen, hydroxyl, amino, mercapto, cyano, nitro, oxo (=O), thioxo (=S), imino (=NR), C(=N—NR$^k$)R$^k$, or C(=N—OR$^k$)R$^k$.

In other embodiments, substituents on any group (such as, for example, alkyl, alkenyl, alkynyl, aryl, aralkyl, heteroaryl, heteroaralkyl, cycloalkyl, and heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents for an alkyl, alkenyl, alkynyl, aryl, aralkyl, heteroaryl, heteroaralkyl, cycloalkyl, and heterocycloalkyl include, without limitation halogen, CN, NO$_2$, OR$^{15}$, SR$^{15}$, S(O)$_2$OR$^{15}$, NR$^{15}$R$^{16}$, C$_1$-C$_2$ perfluoroalkyl, C$_1$-C$_2$ perfluoroalkoxy, 1,2-methylenedioxy, (=O), (=S), (=NR$^{15}$), C(O)OR$^{15}$, C(O)NR$^{15}$R$^{16}$, OC(O)NR$^{15}$R$^{16}$, NR$^{15}$C(O)NR$^{15}$R$^{16}$, C(NR$^{16}$)NR$^{15}$R$^{16}$, NR$^{15}$C(NR$^{16}$)NR$^{15}$R$^{16}$, S(O)$_2$NR$^{15}$R$^{16}$, R$^{17}$, C(O)H, C(O)R$^{17}$, NR$^{15}$C(O)R$^{17}$, Si(R$^{15}$)$_3$, OSi(R$^{15}$)$_3$, Si(OH)$_2$R$^{15}$, B(OH)$_2$, P(O)(OR$^{15}$)$_2$, S(O)R$^{17}$, or S(O)$_2$R$^{17}$. Each R$^{15}$ is independently hydrogen, C$_1$-C$_6$ alkyl optionally substituted with cycloalkyl, aryl, heterocycloalkyl, or heteroaryl. Each R$^{16}$ is independently hydrogen, C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each R$^{17}$ is independently C$_3$-C$_6$ cycloalkyl, aryl, heterocycloalkyl, heteroaryl, C$_1$-C$_4$ alkyl or C$_1$-C$_4$ alkyl substituted with C$_3$-C$_6$ cycloalkyl, aryl, heterocycloalkyl or heteroaryl. Each C$_3$-C$_6$ cycloalkyl, aryl, heterocycloalkyl, heteroaryl and C$_1$-C$_4$ alkyl in each R$^{15}$, R$^{16}$ and R$^{17}$ can optionally be substituted with halogen, CN, C$_1$-C$_4$ alkyl, OH, C$_1$-C$_4$ alkoxy, COOH, C(O)OC$_1$-C$_4$ alkyl, NH$_2$, C$_1$-C$_4$ alkylamino, or C$_1$-C$_4$ dialkylamino.

In certain embodiments, a compound of the invention may be optionally substituted with (i) alkyl, haloalkyl, aryl, halogen, hydroxyl, alkoxy, hydroxyalkyl, amino, mono-alkyl amine, di-alkyl amine, cyano, CONH$_2$, CO$_2$alkyl, SO$_2$NH$_2$, or (ii) heterocyclic or heteroaryl, selected from the following: morpholine,

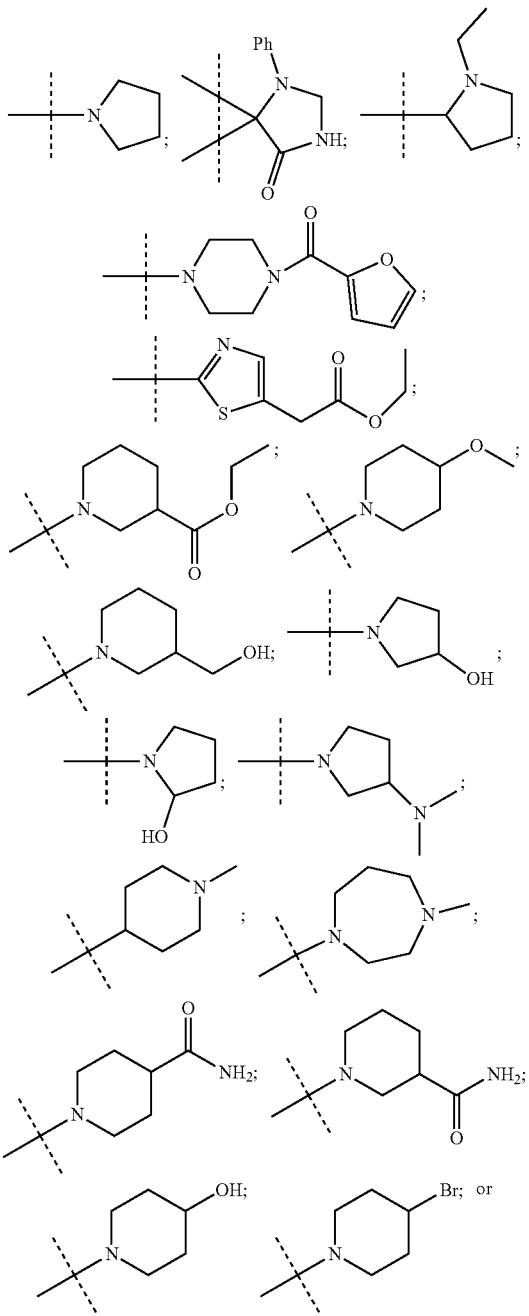

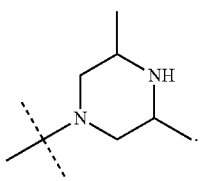

In certain embodiments, an optionally substituted aryl or heteroaryl may be selected from the following: an optionally substituted phenyl, an optionally substituted naphthyl, an optionally substituted anthracenyl, an optionally substituted fluorenyl, an optionally substituted indenyl, an optionally substituted azulenyl, an optionally substituted pyridyl, an optionally substituted 1-oxo-pyridyl, an optionally substituted furanyl, an optionally substituted benzo[1,3]dioxolyl, an optionally substituted benzo[1,4]dioxinyl, an optionally substituted thienyl, an optionally substituted pyrrolyl, an optionally substituted oxazolyl, an optionally substituted imidazolyl, an optionally substituted thiazolyl, an optionally substituted isoxazolyl, an optionally substituted quinolinyl, an optionally substituted pyrazolyl, an optionally substituted isothiazolyl, an optionally substituted pyridazinyl, an optionally substituted pyrimidinyl, an optionally substituted pyrazinyl, an optionally substituted triazinyl, an optionally substituted triazolyl, an optionally substituted thiadiazolyl, an optionally substituted isoquinolinyl, an optionally substituted indazolyl, an optionally substituted benzoxazolyl, an optionally substituted benzofuryl, an optionally substituted indolizinyl, an optionally substituted imidazopyridyl, an optionally substituted tetrazolyl, an optionally substituted benzimidazolyl, an optionally substituted benzothiazolyl, an optionally substituted benzothiadiazolyl, an optionally substituted benzoxadiazolyl, an optionally substituted indolyl, an optionally substituted tetrahydroindolyl, an optionally substituted azaindolyl, an optionally substituted indazolyl, an optionally substituted imidazopyridyl, an optionally substituted quinazolinyl, an optionally substituted purinyl, an optionally substituted pyrrolo[2,3]pyrimidinyl, an optionally substituted pyrazolo[3,4]pyrimidinyl, or an optionally substituted benzo(b)thienyl.

In certain embodiments, an optionally substituted heterocycloalkyl may be selected from the following: an optionally substituted piperidinyl, an optionally substituted piperazinyl, an optionally substituted 2-oxopiperazinyl, an optionally substituted 2-oxopiperidinyl, an optionally substituted 2-oxopyrrolidinyl, an optionally substituted 4-piperidonyl, an optionally substituted tetrahydropyranyl, an optionally substituted oxazolidinyl, an optionally substituted 2-oxooxazolidinyl, an optionally substituted tetrahydrothiopyranyl, an optionally substituted tetrahydrothiopyranyl sulfone, an optionally substituted morpholinyl, an optionally substituted thiomorpholinyl, an optionally substituted thiomorpholinyl sulfoxide, an optionally substituted thiomorpholinyl sulfone, an optionally substituted 1,3-dioxolane, tetrahydrofuranyl, or an optionally substituted tetrahydrothienyl.

The recitation of a listing of chemical groups in any definition of a variable herein includes definitions of that variable as any single group or combination of listed groups.

The compounds of this invention include the compounds themselves, as well as their salts, solvate, clathrate, hydrate, polymorph, or prodrugs, if applicable.

As used herein, the term "pharmaceutically acceptable salt," is a salt formed from, for example, an acid and a basic group of a compound of any one of the formulae disclosed herein. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N, N-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, which further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed).

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

EXAMPLES

The invention is further illustrated by the following examples which should in no way should be construed as being further limiting. The compounds of the invention were synthesized according to the examples provided herein and according to the reaction schemes provided supra.

Example 1: Preparation of 2-(4-(4-(trifluoromethoxy)phenylamino)-1H-pyrazolo[3,4-d]pyrimidin-1-yl)ethanol and 2-(4-(4-(trifluoromethoxy)phenylamino)-2H-pyrazolo[3,4-d]pyrimidin-2-yl)ethanol

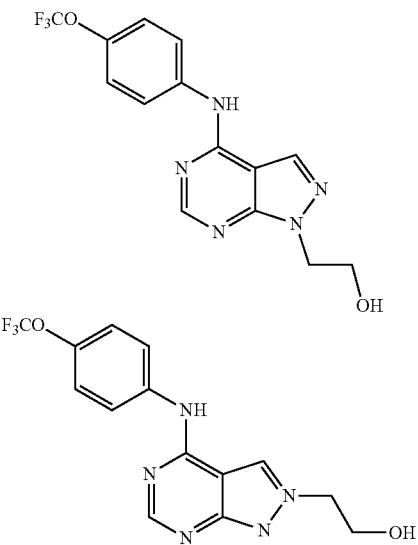

Step 1: 4-Chloro-6-(4-trifluoromethoxy-phenylamino)-pyrimidine-5-carbaldehyde

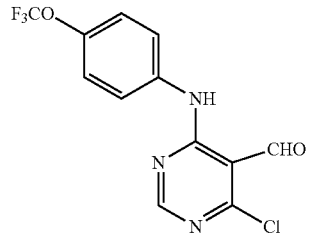 [SMILES: O=Cc1c(Cl)ncnc1Nc1ccc(OC(F)(F)F)cc1]

To a solution of 4,6-Dichloro-pyrimidine-5-carbaldehyde (3.06 g, 17.5 mmol) in THF (15 mL) was added 4-trifluoromethoxyaniline (3.09 g, 17.45 mmol) at 0° C. The mixture was stirred for 2 h and ethyl acetate (100 mL) was added. The organic layer was separated from brine, dried (Na$_2$SO$_4$) and concentrated to yield crude title compound as yellow solids. The compound was then purified by silica gel column chromatography to give the title compound as yellow crystals. (2.9 g, 55%). MS m/z 318.2 (M+1).

Step 2: 2-(4-(4-(trifluoromethoxy)phenylamino)-1H-pyrazolo[3,4-d]pyrimidin-1-yl)ethanol and 2-(4-(4-(trifluoromethoxy)phenylamino)-2H-pyrazolo[3,4-d]pyrimidin-2-yl)ethanol To solution of 4-chloro-6-(4-trifluoromethoxy-phenylamino)-pyrimidine-5-carbaldehyde (50 g, 0.15 mmol) in sec-BuOH was added Na$_2$CO$_3$ (30 mg, 0.26 mmol) and hydrazine (20 mg, 0.18 mmol). The reaction was stirred at 60° C. temperature for 8 hours. The reaction mixture was partitioned in 100 ml water and 100 ml ethyl acetate, extracted with ethyl acetate three times. The organic phase was combined and washed with brine, dried over Na$_2$SO$_4$. The crude product was purified by silica gel flash chromatography by using hexane:ethyl acetate as eluent resulting 2-(4-(4-(trifluoromethoxy)phenylamino)-1H-pyrazolo[3,4-d]pyrimidin-1-yl)ethanol and 2-(4-(4-(trifluoromethoxy)phenylamino)-2H-pyrazolo[3,4-d]pyrimidin-2-yl)ethanol in the ratio of 4:1 as yellow solids.

2-(4-(4-(trifluoromethoxy)phenylamino)-1H-pyrazolo[3,4-d]pyrimidin-1-yl)ethanol (20 mg): $^1$H NMR 400 MHz (DMSO-d$_6$) δ 10.30 (s, 1H), 8.45 {s, 1H (6-Ar—H)}, 8.32 {s, 1H (3-Ar—H)}, 7.98 (d, 2H, J=9.6 Hz), 7.41 (d, 2H, J=9.6 Hz), 4.40 (t, 2H, J=3.0 Hz), 3.83 (t, 2H, J=3.0 Hz); MS m/z 340.2 (M+1).

2-(4-(4-(trifluoromethoxy)phenylamino)-2H-pyrazolo[3,4-d]pyrimidin-2-yl)ethanol (5 mg): $^1$H NMR 400 MHz (DMSO-d$_6$) δ 10.75 (s, 1H), 8.68 {s, 1H (3-Ar—H)}, 8.57 {s, 1H (6-Ar—H)}, 7.97 (d, 2H, J=9.6 Hz), 7.45 (d, 2H, J=9.6 Hz), 4.41 (t, 2H, J=3.0 Hz), 3.85 (t, 2H, J=3.0 Hz); MS m/z 340.2 (M+1).

Example 2: N-(2-Morpholin-4-yl-ethyl)-3-[4-(4-trifluoromethoxy-phenylamino)-pyrrolo[2,3-d]pyrimidin-7-yl]-propionamide

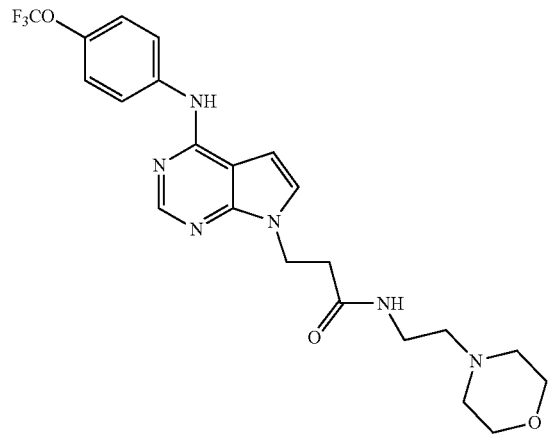 [SMILES: O=C(CCn1ccc2c(Nc3ccc(OC(F)(F)F)cc3)ncnc21)NCCN1CCOCC1]

Step 1: 3-(4-Chloro-pyrrolo[2,3-d]pyrimidin-7-yl)-propionic acid ethyl ester

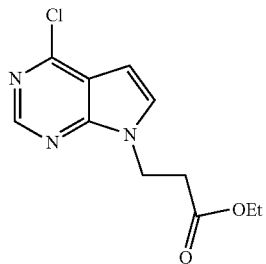 [SMILES: CCOC(=O)CCn1ccc2c(Cl)ncnc21]

To a solution of 4-Chloro-7H-pyrrolo[2,3-d]pyrimidine (1 g, 6.53 mmol) in DMF (30 mL), cooled at 0° C., was added slowly NaH (1.8 g, 9.14 mmol). After stirring for 30 min at room temperature, the 4-(2-chloro-ethyl)-morpholine (1.28 g, 7.18 mmol) was added. The reaction mixture was stirring for 16 h at 40° C. The mixture was brought to room temperature and then quenched with saturated NH$_4$Cl solution and extracted with 150 ml of ethyl acetate. The organic extracts were washed with brine, dried over Na$_2$SO$_4$ and concentrated. The residue was purified by column chromatography (silica gel, eluting with hexanes) to afford the title compound (1.2 g, 72%). $^1$H NMR 600 MHz (DMSO-d$_6$) δ 9.01 (s, 1H), 6.26 (d, 1H, J=3.0 Hz), 5.91 (d, 1H, J=3.0 Hz), 4.24 (t, 2H, J=5.4 Hz), 4.12 (t, 2H, J=5.0 Hz), 2.73 (d, 2H, J=5 Hz), 1.21 (d, 3H, J=4 Hz); MS m/z 254.2 (M+1).

Step 2: 3-[4-(4-Trifluoromethoxy-phenylamino)-pyrrolo[2,3-d]pyrimidin-7-yl]-propionic acid ethyl ester

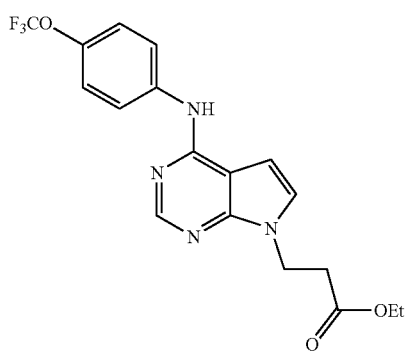 [SMILES: CCOC(=O)CCn1ccc2c(Nc3ccc(OC(F)(F)F)cc3)ncnc21]

To a solution of 3-(4-Chloro-pyrrolo[2,3-d]pyrimidin-7-yl)-propionic acid ethyl ester (100 mg, 0.37 mmol) in sec-BuOH (3 mL) was added 4-trifluoromethoxyaniline (73 mg, 0.41 mmol). The mixture was heated at 120° C. and stirred for 2 h. The reaction mixture was concentrated and purified by prep-HPLC to afford the title compound as brown solid as TFA salt (114 mg, 60%). MS m/z 408.1 (M+1).

Step 3: 3-[4-(4-Trifluoromethoxy-phenylamino)-pyrrolo[2,3-d]pyrimidin-7-yl]-propionic acid

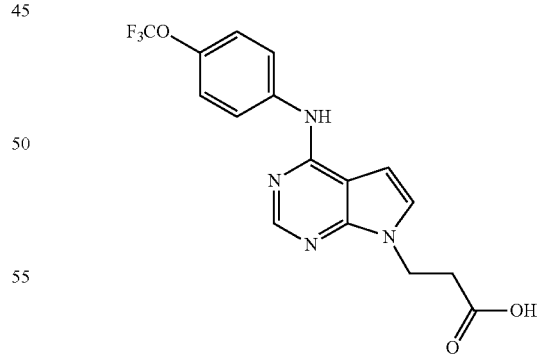

To a solution of 3-[4-(4-Trifluoromethoxy-phenylamino)-pyrrolo[2,3-d]pyrimidin-7-yl]-propionic acid ethyl ester (100 mg, 0.24 mmol) in 5 mL of THF:H$_2$O (3:1)) was added CsCO$_3$ (78 mg, 0.40 mmol). The mixture was heated at 80° C. and stirred for 2 h. The reaction mixture was concentrated and neutralized with acetic acid. The solid was filtered and dried to yield the tile compound as brown solid (67 mg, 77%). MS m/z 367.1 (M+1).

Step 4: N-(2-Morpholin-4-yl-ethyl)-3-[4-(4-trifluoromethoxy-phenylamino)-pyrrolo[2,3-d]pyrimidin-7-yl]-propionamide 3-[4-(4-Trifluoromethoxy-phenylamino)-pyrrolo[2,3-d]pyrimidin-7-yl]-propionic acid (25 mg, 0.068 mmol) was mixed with DIEA (0.030 ml, 0.172 mmol) and HATU (28.5 mg, 0.071 mmol) in 2 ml DMF at room temperature. 2-Morpholin-4-yl-ethylamine (9.7 uL, 0.074 mmol) was added into the reaction mixture 0.5 hour later. After stirring at room temperature for 2 hours, the reaction mixture was concentrated and purified by Prep-HPLC to afford the title compound as TFA salt. MS m/z 479.2 (M+1).

Example 3: Preparation of N-(2-hydroxyethyl)-4-(4-(trifluoromethoxy) phenylamino)thieno[2,3-d]pyrimidine-6-carboxamide

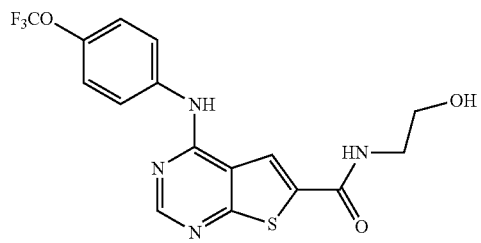

Step 1: Methyl 4-(4-(trifluoromethoxy)phenylamino)thieno[2,3-d]pyrimidine-6-carboxylate

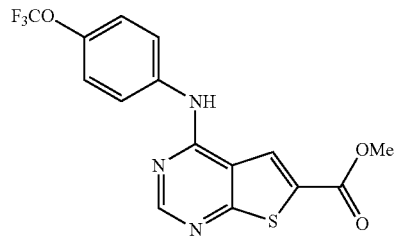 [SMILES: COC(=O)c1cc2c(Nc3ccc(OC(F)(F)F)cc3)ncnc2s1]

4-Chloro-6-(4-trifluoromethoxy-phenylamino)-pyrimidine-5-carbaldehyde (500 g, 1.5 mmol) in DMF (2 mL) was added to a suspension of $K_2CO_3$ (620 mg, 4.5 mmol) in DMF (1 mL) at room temperature. After stirring for 30 min, methyl thioglucolate (210 mg, 1.9 mmol) was added slowly into the reaction mixture. The reaction mixture was then heated at 90° C. for 1 h. The reaction mixture was then cooled down at room temperature and poured onto ice cold water. The residue appeared was filtered, washed and dried to afford the title compound as white solid (400 g, 72% Yield). MS m/z 370.2 (M+1).

Step 2: 4-(4-(trifluoromethoxy)phenylamino)thieno[2,3-d]pyrimidine-6-carboxylic acid

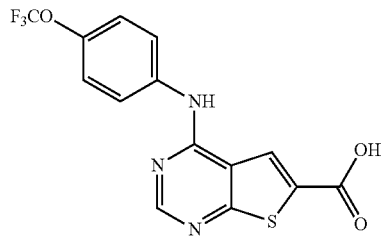

A mixture of methyl 4-(4-(trifluoromethoxy)phenylamino)thieno[2,3-d]pyrimidine-6-carboxylate (152 mg, 0.43 mmol), LiOH (25.5 mg, 1.07 mmol) was dissolved in THF (4 ml) and $H_2O$ (1 mL). The mixture was stirred at 60° C. for 3 h. Acidified with acetic acid resulted brown solid which was collected by filtration. It was then dried in vacuo and used for the next step without any further purification (115 mg, 75% Yield). MS m/z 356.1 (M+1).

Step 3: N-(2-hydroxyethyl)-4-(4-(trifluoromethoxy)phenylamino)thieno[2,3-d]pyrimidine-6-carboxamide 4-(4-(trifluoromethoxy)phenylamino)thieno[2,3-d]pyrimidine-6-carboxylic acid (30 mg, 0.08 mmol) was mixed with DIEA (30 uL, 0.172 mmol) and HATU (39 mg, 0.1 mmol) in 2 ml DMF at room temperature. 2-Aminoethanol (6.1 mg, 0.1 mmol) was added into the reaction mixture 0.5 hour later. After stirring at room temperature for 2 hours, the reaction mixture was concentrated and purified by prep-HPLC to afford the title compound as TFA salt (25 mg, 61% Yield). $^1$H NMR 400 MHz (DMSO-$d_6$) δ 10.10 (s, 1H), 9.26 (s, 1H), 8.82 (s, 1H), 8.21 (d, 2H, J=8.8 Hz), 7.85 (d, 2H, J=8.8 Hz), 7.34 (s, 1H), 3.02 (t, 2H, J=6.4 Hz), 2.65 (t, 2H, J=6.4 Hz). MS m/z 399.12 (M+1).

Example 4: 4-(4-(trifluoromethoxy)phenylamino)-N-(2-hydroxyethyl)quinazoline-7-carboxamide

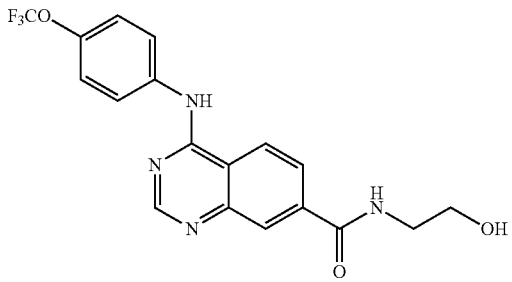 [SMILES: O=C(NCCO)c1ccc2c(Nc3ccc(OC(F)(F)F)cc3)ncnc2c1]

Step 1: Methyl 4-(4-(trifluoromethoxy)phe-nylamino)quinazoline-7-carboxylate

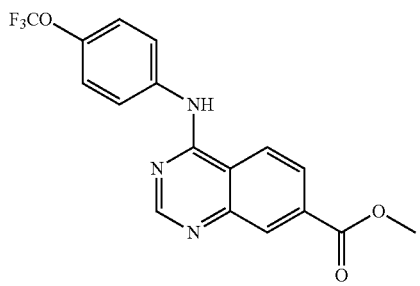 [SMILES: COC(=O)c1ccc2c(Nc3ccc(OC(F)(F)F)cc3)ncnc2c1]

To a solution of methyl 4-chloroquinazoline-7-carboxylate (610 mg, 2.75 mmol) in sec-BuOH (5 mL) was added 4-trifluoromethoxyaniline (535.5 mg, 3.02 mmol) at room temperature. The mixture was heated at 100° C. and stirred for 2 h. The solvent was evaporated and the compound was crystallized from CHCl$_3$ and Et$_2$O mixture (3:1). The white crystals were collected by filtration and washed with Et$_2$O. (890 mg, 91% Yield). MS m/z 364.10 (M+1).

Step 2: 4-(4-(trifluoromethoxy)phenylamino)qui-nazoline-7-carboxylic acid

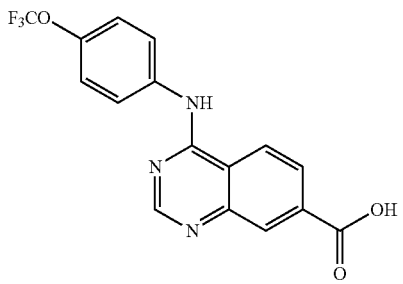 [SMILES: O=C(O)c1ccc2c(Nc3ccc(OC(F)(F)F)cc3)ncnc2c1]

A mixture of methyl 4-(4-(trifluoromethoxy)phe-nylamino)quinazoline-7-carboxylate (156 mg, 0.43 mmol), LiOH (25.5 mg, 1.07 mmol) was dissolved in THF (4 ml) and H$_2$O (1 mL). The mixture was stirred at 60° C. for 3 h. Acidified with acetic acid resulted brown solid which was collected by filtration. It was then dried in vacuo and used for the next step without any further purification (120 mg, 80% Yield). $^1$H NMR 400 MHz (DMSO-d$_6$) δ 12.25 (s, 1H), 10.12 (s, 1H), 8.68 (s, 1H), 8.65 (d, 1H, J=1.6 Hz), 8.20-8.11 (m, 2H), 8.02 (d, 2H, J=8.8 Hz), 7.42 (d, 2H, J=8.8 Hz. MS m/z 350.1 (M+1).

Step 3: 4-(4-(trifluoromethoxy)phenylamino)-N-(2-hydroxyethyl)quinazoline-7-carboxamide 4-(4-(trifluoromethoxy)phenylamino)quinazoline-7-car-boxylic acid (30 mg, 0.09 mmol) was mixed with DIEA (30 uL, 0.172 mmol) and HATU (39 mg, 0.1 mmol) in 2 ml DMF at room temperature. 2-Aminoethanol (6.1 mg, 0.1 mmol) was added into the reaction mixture 0.5 hour later. After stirring at room temperature for 2 hours, the reaction mixture was concentrated and purified by prep-HPLC to afford the title compound as TFA salt (29 mg, 82% Yield). MS m/z 393.04 (M+1).

Example 5: Preparation of 4-(6-(4-(trifluo-romethoxy)phenylamino)-5-methylpyrimidin-4-yl)-N-(2-morpholinoethyl)benzamide

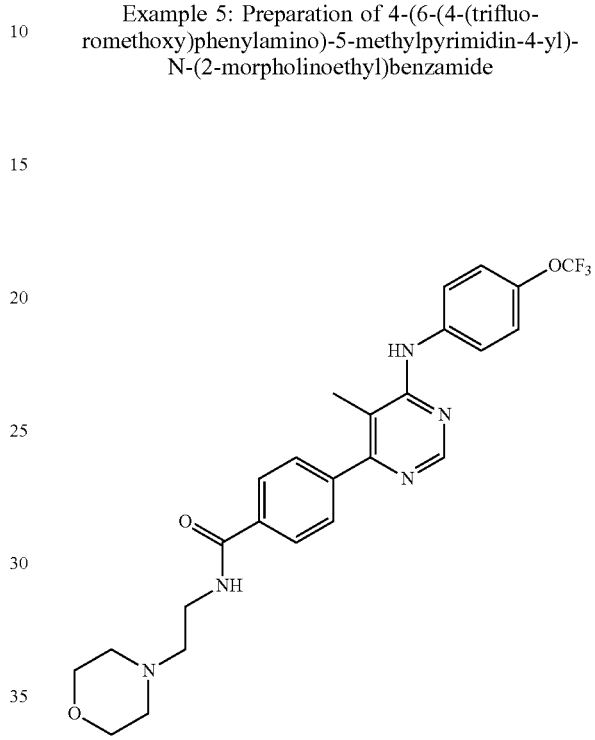

Step 1: 6-chloro-5-methyl-N-(4-(trifluoromethoxy)phenyl)pyrimidin-4-amine

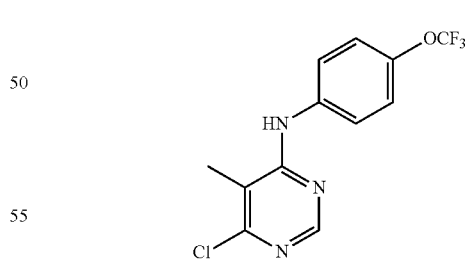

4,6-Dichloro-5-methylpyrimidine (534.6 mg, 3.3 mmol) and 4-trifluoromethoxy aniline (661 mg, 3.6 mmol) were dissolved in EtOH and DIEA (625 uL, 3.6 mmol) was added and the mixture was refluxed for 4 h. It was then cooled, concentrated and work-up with ethyl acetate. The organic layer was separated and dried (Na$_2$SO$_4$). Concentrated and purified by silica-gel column chromatography (Ethyl acetate/hexane). 800 mg (84% Yield), MS m/z 304.14 (M+1).

Step 2: 4-(6-(4-(trifluoromethoxy)phenylamino)-5-methylpyrimidin-4-yl)benzoic acid

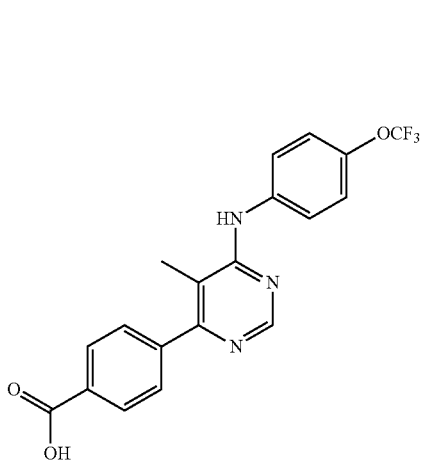 [SMILES: Cc1c(Nc2ccc(OC(F)(F)F)cc2)ncnc1-c1ccc(C(=O)O)cc1]

Chloropyrimidine intermediate (521 mg, 1.72 mmol), 4-carboxyphenylboronic acid (287 mg, 1.72 mmol), Pd(PPh$_3$)$_4$ (100 mg, 0.85 mmol) and sodium carbonate (730 mg, 6.9 mmol) were dissolved in acetonitrile:water (v/v 1:1, 10 ml). The flask was stirred at 95° C. for 5 hr. The insoluble residues were removed by filtering the hot reaction solution. A solution of aq. HCl (6N) was added until ~pH<5. The solid was collected by filtration and rinsed with water and used without further purification (500 mg, 74% Yield). MS m/z 390.20 (M+1).

Step 3: 4-(6-(4-(trifluoromethoxy)phenylamino)-5-methylpyrimidin-4-yl)-N-(2-morpholinoethyl) benzamide 21 mg (0.55 mmol) of 2,2-aminoethanol (4.3 mg, 0.066 mmol) and DIEA (37 uL, 0.21 mmol) were dissolved in DMF (1.5 ml) and stirred for 5 min. 26.5 mg (0.07 mmol) was added and the reaction mixture was continued to stir for another 6 at room temperature. The desired product was purified by mass triggered HPLC to give 22 mg (75% yield) as TFA salt. MS m/z 502.23 (M+1).

Example 6: Preparation of 6-(1H-pyrrolo[2,3-b]pyridin-1-yl)-N-(4-(trifluoromethoxy)phenyl)pyrimidin-4-amine

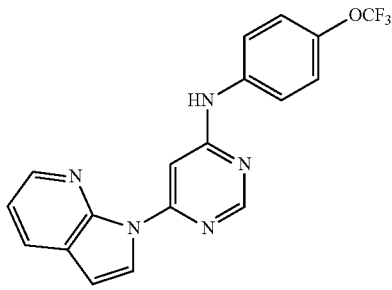 [SMILES: FC(F)(F)Oc1ccc(Nc2cc(-n3ccc4cccnc43)ncn2)cc1]

Step 1: 6-chloro-N-(4-(trifluoromethoxy)phenyl)pyrimidin-4-amine

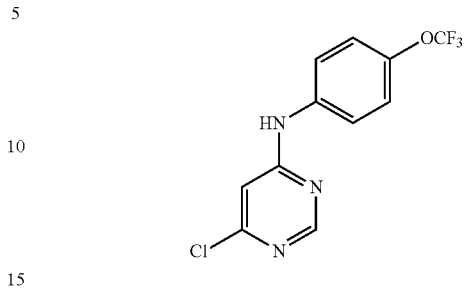

4,6-Dichloropyrimidine (250 mg, 3.3 mmol) and 4-trifluoromethoxy aniline (330.5 mg, 1.8 mmol) were dissolved in EtOH and DIEA (312.5 uL, 1.8 mmol) was added and the mixture was refluxed for 4 h. It was then cooled, concentrated and work-up with ethyl acetate. The organic layer was separated and dried (Na$_2$SO$_4$). Concentrated and purified by silica-gel column chromatography (Ethyl acetate/hexane). 400 mg (84% Yield). MS m/z 290.04 (M+1).

Step 2: 6-(1H-pyrrolo[2,3-b]pyridin-1-yl)-N-(4-(trifluoromethoxy)phenyl)pyrimidin-4-amine To a solution of compound 7-azaindole (18 mg, 0.15 mmol) in sec-BuOH (5 mL) was added DIEA (0.20 mL) and the reaction mixture was stirred for 15 min at RT. 6-Chloro-N-(4-(trifluoromethoxy)phenyl)pyrimidin-4-amine (29 mg, 0.1 mmol) was then added and the temperature was raised to 90° C. and continued stirring for another 16 h. The solvent was removed and the title compound was purified by prep. HPLC (15 mg, 40% Yield). MS m/z 372.10 (M+1).

Example 7: Preparation of N-(4-(trifluoromethoxy)phenyl)-6-(1,3,5-trimethyl-1H-pyrazol-4-yl)pyrimidin-4-amine

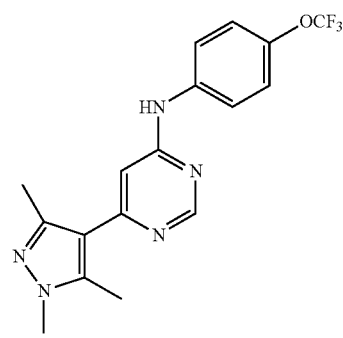 [SMILES: Cc1nn(C)c(C)c1-c1cc(Nc2ccc(OC(F)(F)F)cc2)ncn1]

6-Chloro-N-(4-(trifluoromethoxy)phenyl)pyrimidin-4-amine intermediate (5.2 mg, 0.17 mmol), 1,3,5-trimethyl-4-(4,4,5,5-tetramethyl-1,3,2-dioxaborolan-2-yl)-1H-pyrazole (40 mg, 0.17 mmol), Pd(PPh$_3$)$_4$ (10 mg, 0.085 mmol) and sodium carbonate (73 mg, 0.69 mmol) were dissolved in acetonitrile:water (v/v 1:1, 10 ml). The flask was stirred at 95° C. for 5 hr. The solvent was removed and directly subjected to prep-HPLC to afford 65 mg (80% Yield) of the title compound as TFA salt. $^1$H NMR 400 MHz (DMSO-d$_6$) δ 10.32 (s, 1H), 8.75 (s, 1H), 8.39 (s, 2H), 7.84 (d, 2H, J=9.2

Hz), 7.45 (d, 2H, J=9.2 Hz), 3.84 (s, 3H), 2.89 (s, 3H), 2.24 (s, 3H). MS m/z 364.11 (M+1).

Example 8: Preparation of 2-(3-nitrophenyl)-N-(4-(trifluoromethoxy)phenyl) imidazo[1,2-c]pyrimidin-7-amine

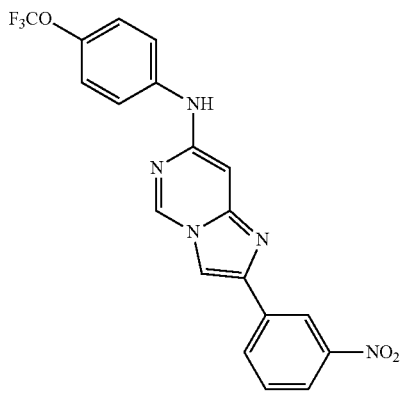 [SMILES: O=[N+]([O-])c1cccc(-c2cn3cnc(Nc4ccc(OC(F)(F)F)cc4)cc3n2)c1]

Step 1: 7-chloro-2-(3-nitrophenyl)imidazo[1,2-c]pyrimidine

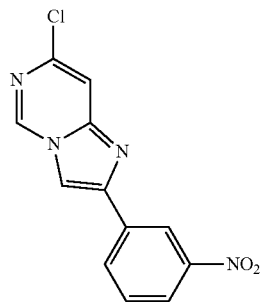 [SMILES: O=[N+]([O-])c1cccc(-c2cn3cnc(Cl)cc3n2)c1]

6-Chloropyrimidin-4-amine (50 mg, 0.39 mmol) and 2-bromo-1-(3-nitrophenyl)ethanone (94 mg, 0.39 mmol) were dissolved in 2 mL of DMSO and the mixture was stirred at room temperature for 3 days. The reaction mixture was poured into 5 mL of water and it was then extracted with ethyl acetate. The filtrate was dried (Na$_2$SO$_4$) and evaporated. The compound was purified by silica gel column chromatography by using hexane/ethyl acetate (3:1) as eluent (60 mg, 56% Yield). MS m/z 275.00 (M+1).

Step 2: 2-(3-Nitrophenyl)-N-(4-(trifluoromethoxy)phenyl)imidazo[1,2-c]pyrimidin-7-amine 7-chloro-2-(3-nitrophenyl)imidazo[1,2-c]pyrimidine (30 mg, 0.11 mmol) and (58 mg, 0.32 mmol) were heated at 120° C. for 1 h. The residue was dissolved in DMSO and directly subjected to prep-HPLC to yield 8 mg (13% Yield) of the title compound as TFA salt. $^1$H NMR 400 MHz (DMSO-d$_6$) δ 10.42 (s, 1H), 8.88 (s, 1H), 8.67 (s, 1H), 8.01-7.99 (m, 3H), 7.92 (d, 2H, J=9.2 Hz), 7.53 (d, 2H, J=9.2 Hz), 7.45 (s, 1H), 7.22 (s, 1H). MS m/z 416.12 (M+1).

Example 9: Biological Data

Cell Culture

Interleukin-3 (IL-3) dependent murine pro-B cell line, Ba/F3, and murine myeloid precursor cell line, 32D, were maintained in RPMI-1640 medium supplemented with L-Glutamine, 10% FBS and 10 U/ml recombinant murine IL-3 (Roche). Mo7e human megakarioblastic cell line was grown in RPMI-1640 medium supplemented with L-Glutamine, 20% FBS and 5 ng/ml recombinant human granulocyte macrophage cell stimulating factor (GM-CSF) (R&D Systems) or 200 ng/ml stem cell factor (SCF) (Biosource).

Wild type Bcr-abl expressing 32D (32D.p210) and Ba/F3 (Ba/F3.p210) cells, and mutant Bcr-abl expressing cell lines Ba/F3.p210$^{G250E}$, Ba/F3.p210$^{E255V}$, Ba/F3.p210$^{T315I}$ Ba/F3.p210$^{F317L}$ and Ba/F3.p210$^{M351T}$, as well as Ba/F3 cells transformed with Flt-3-ITD kinase. Additional assays included Ba/F3 cells expressing the fusion protein kinases TEL-PDGFRβ, TEL-JAK1, NPM-ALK, TEL-cKit, Tel-Bmx, Tel-FGR3, Tel-Lck and Ba/F3.TPR-met cells. All the above cell lines were maintained in RPMI-1640 medium with L-Glutamine, 10% FBS and 1 mg/ml geneticin (Gibco).

Human leukemic cell lines K562 (p210 Bcr-abl expressing chronic myelogenous leukemia), HL-60 (acute promyelocytic leukemia), SUP/B15 (p190 Bcr-abl expressing acute lymphoblastic leukemia) and Jurkat (acute T cell leukemia) were purchased from the American Type Culture Collection (ATCC) and cultured following ATCC recommendations.

Proliferation Assays

Cells (0.3-0.6×10$^6$/ml) were plated in duplicate or triplicate in 96-well plates containing increasing drug concentrations (0.005-10 μM). After incubation at 37° C. in 5% CO$_2$ for 48 h, the effect of the compounds on cell viability was determined by MTT (Promega) colorimetric dye reduction method. Inhibition of cell proliferation was calculated as a percentage of growth of DMSO treated cells, and IC$_{50}$ values were determined with Microsoft Excel XLfit3.

Simultaneous treatment of Ba/F3.p210 cells with imatinib and GNF-2 was carried out to evaluate the synergistic or additive effect of the drug combinations on cellular proliferation. Cells treated with increasing concentrations of each compound alone or in combination were incubated at 37° C. in 5% CO$_2$ for 48 h, and the cell viability determined by the MTT assay. The in vitro additive, synergistic or antagonistic effect was determined by calculating the combination index (CI) from two independent experiments using CalcuSyn Software.

Cell Cycle Analysis

Cells grown for 24 or 48 hours in medium containing different concentrations of compound were collected by centrifugation (10 min, 4° C.), washed twice with PBS and fixed in 70% ethanol at −20° C. After fixation, ethanol was removed by centrifugation (10 min, 4° C.), and the cells were resuspended in PBS containing 1 mM EDTA and 100 μg/ml RNAse A (Sigma) and incubated 30 min at 37° C. Cells were stained with propidium iodide (10 μg/ml) and DNA content was determined by flow cytometry (FACScan, Becton Dickinson).

Phosphotyrosine Analysis

The total cellular tyrosine phosphorylation levels of Bcr-abl were first determined by using capture ELISA. Bcr-abl expressing cells treated for 90 min with various concentrations of test compounds were homogenized in lysis buffer (50 mM Tris·HCl pH7.4, 150 mM NaCl, 5 mM EDTA, 1 mM EGTA, 1% NP-40, 2 mM Na$_3$VO$_4$ and protease inhibitor cocktail (Roche)) and the lysates plated on 96 well plates containing adsorbed anti-Abl SH3 domain polyclonal antibody (Upstate Biotechnology). The plates were incubated for 4 h at 4° C. and then washed with PBS/0.05% Tween 20 buffer. To detect phosphotyrosine residues, alkaline phosphatase-conjugated monoclonal anti-phosphotyrosine antibody (PY20, Zymed Laboratories) was added to each well, and plates were incubated overnight at 4° C. The wells were then washed with PBS/0.05% Tween 20 buffer, and 100 μl/well of CDP-Star® Substrate with Emerald-II™ enhancer substrate (Applied Biosystems) was added. After 45 min, light emission was quantified with a GeminiXS microplate reader (Molecular Devices). Bcr-abl phosphotyrosine content was calculated as a percentage of phosphotyrosine of non treated cells, and $IC_{50}$ values were determined with Microsoft Excel XLfit3.

The state of tyrosine phosphorylation of cellular Bcr-abl and it substrate Stat5 after drug treatment was determined by western blot with phospho-specific antibodies. Ba/F3.p210 and Ba/F3.p210$^{E255V}$ cells were incubated in the presence of various concentrations of GNF-2 and, after 1.5 h incubation, lysed in lysis buffer (20 mM Tris-HCl (pH 7.5), 150 mM NaCl, 1 mM Na$_2$EDTA, 1 mM EGTA, 1% Triton, 2.5 mM sodium pyrophosphate, 1 mM beta-glycerophosphate, 1 mM Na$_3$VO$_4$, 1 μg/ml leupeptin, 1 mM PMSF). Equal amount of lysates (50 μg) were subjected to SDS-PAGE followed by immunoblotting with phospho-specific antibodies recognizing Bcr-abl phosphorylation sites: anti-phospho-c-Abl (Tyr 245), and anti-phospho-Stat5 (Tyr 694) (Cell signaling) antibodies or antibodies against Bcr-abl (Ab-3, Oncogene Science) and Stat5 (C-17, Santa Cruz Biotechnology). Proteins were detected by enhanced chemioluminiscence (ECL-plus, Amersham), following manufacturer's guidelines.

Protein Expression and Purification

Recombinant c-abl (residues 46-531) was expressed as a His$_6$ tag fusion protein in Sf9 insect cells using the Bac-to-Bac baculovirus expression system (Invitrogen) as previously described. Briefly, infected cells were grown for 48 h, harvested by centrifugation, suspended in lysis buffer (50 mM Tris pH 8.0, 300 mM NaCl, 5% glycerol, 10 mM 2-mercaptoethanol and protease inhibitor cocktail (Roche) and lysed by sonication. After centrifugation, the cell extract was loaded on a Ni-NTA affinity column and Abl was eluted with 250 mM imidazole. Fractions containing abl were pooled and the concentration of imidazole was reduced to 20 mM by dialysis. The protein was treated with CiP alkaline phosphatase (Invitrogen) and purified by a second Ni affinity chromatography. The His$_6$ tag was removed by treatment with TEV protease (Invitrogen) and the protein recovered from a Ni-NTA column with a purity of ~90% by SDS-PAGE and coomassie blue staining.

Kinase Assays

In vitro kinase assays were carried out by using recombinant murine c-abl containing SH3, SH2 and kinase domains (residues 46-531) and full length immunoprecipitated Bcr-abl. Recombinant abl was expressed in Sf9 insect cells and purified as described above. Bcr-abl immune complexes were obtained with Ab-3 anti-abl monoclonal antibody (Oncogene Science) from Ba/F3.p210 lysates as previously described.

1 μg of recombinant abl or immunoprecipitated Bcr-abl (from 3×10$^6$ cells) were incubated with various concentrations of test compound (0.1, 1 and 10 μM) in kinase buffer (50 mM Tris-HCl pH 7.5, 10 mM MgCl$_2$, 100 mM EDTA, 1 mM DTT, 0.015% Brij 35), 100 μM ATP and 1 μCi [γ-$^{32}$P]-ATP for 30 min at 30° C. (Calbiochem buffer and protocol). The reaction was stopped by addition of Laemmli buffer and the proteins were resolved by SDS-PAGE in a 4-20% gel. The phosphoproteins were visualized by autoradiography and the autophosphorylation quantitated using a phosphoimager (STORM, Molecular Devices).

The results are provided in the following tables.

TABLE 10

| Structure | Spectroscopy | BaF3 | Bcr-Abl | T315I |
| --- | --- | --- | --- | --- |
| 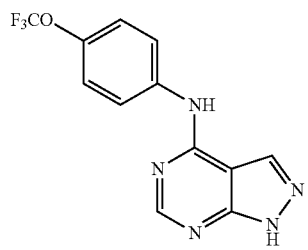 [SMILES: FC(F)(F)Oc1ccc(Nc2ncnc3[nH]ncc23)cc1] | MS m/z 296.09 (M + 1). | >10 | 1.3 | >10 |
| 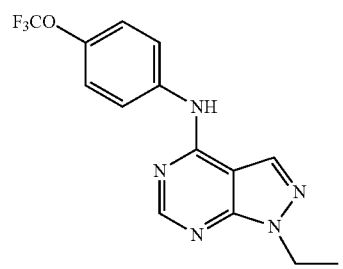 [SMILES: CCn1ncc2c(Nc3ccc(OC(F)(F)F)cc3)ncnc21] | MS m/z 324.11 (M + 1). | >10 | 0.300 | 7.3 |

TABLE 10-continued

| Structure | Spectroscopy | BaF3 | Bcr-Abl | T315I |
|---|---|---|---|---|
| (F₃CO-phenyl-NH-pyrazolopyrimidine, N-ethyl) | MS m/z 324.16 (M + 1). | >10 | 1.2 | >10 |
| (F₃CO-phenyl-NH-pyrazolopyrimidine, N-SO₂Et) | MS m/z 388.10 (M + 1). | 7.0 | 0.400 | 3.8 |
| (F₃CO-phenyl-NH-pyrazolopyrimidine, N-cyclohexyl) | MS m/z 378.10 (M + 1). | 9.3 | 0.400 | 4.6 |
| (F₃CO-phenyl-NH-pyrazolopyrimidine, 2-N-cyclohexyl) | MS m/z 378.10 (M + 1). | >10 | 2.2 | 6.2 |
| (F₃CO-phenyl-NH-pyrazolopyrimidine, N-CH₂CH₂OH) | $^1$H NMR 400 MHz (DMSO-d$_6$) δ 10.25 (s, 1H), 8.45 {s, 1H (6-Ar—H)}, 8.32 {s, 1H (3-Ar—H), 7.98 (d, 2H, J = 9.6 Hz), 7.41 (d, 2H, J = 9.6 Hz), 4.40 (t, 2H, J = 3.0 Hz), 3.83 (t, 2H, J = 3.0 Hz); MS m/z 340.2 (M + 1). | >10 | 0.254 | 4.2 |

TABLE 10-continued

| Structure | Spectroscopy | BaF3 | Bcr-Abl | T315I |
|---|---|---|---|---|
| (F₃CO-phenyl-NH-pyrazolopyrimidine-N-CH₂CH₂OH) | ¹H NMR 400 MHz (DMSO-d₆) δ 10.75 (s, 1H), 8.68 {s, 1H (3-Ar—H)}, 8.57 {s, 1H (6-Ar—H), 7.97 (d, 2H, J = 9.6 Hz), 7.45 (d, 2H, J = 9.6 Hz), 4.41 (t, 2H, J = 3.0 Hz), 3.85 (t, 2H, J = 3.0 Hz); MS m/z 340.2 (M + 1). | >10 | 1.32 | >10 |
| (F₃CO-phenyl-NH-pyrazolopyrimidine-N-CH₂C(O)NH₂) | ¹H NMR 400 MHz (DMSO-d₆) δ 10.56 (s, 1H), 8.67 (s, 1H), 8.55 (s, 1H), 7.98 (d, 2H, J = 8.8 Hz), 7.78 (s, 1H), 7.45 (d, 2H, J = 8.8 Hz), 7.30 (s, 1H), 5.17 (s, 2H); MS m/z 353.21 (M + 1). | >10 | 4.34 | >10 |
| (F₃CO-phenyl-NH-pyrazolopyrimidine-N-CH₂C(O)NH₂ isomer) | ¹H NMR 400 MHz (DMSO-d₆) δ 10.27 (s, 1H), 8.44 (s, 1H), 8.32 (s, 1H), 7.99 (d, 2H, J = 8.8 Hz), 7.60 (s, 1H), 7.41 (d, 2H, J = 8.8 Hz), 7.30 (s, 1H), 4.9 (s, 2H); MS m/z 353.02 (M + 1). | >3.3 | 0.346 | 3.097 |
| (F₃CO-phenyl-NH-pyrazolopyrimidine-N-CH₂CH₂C(O)NH₂) | ¹H NMR 400 MHz (DMSO-d₆) δ 10.79 (s, 1H), 8.67 (s, 1H), 8.56 (s, 1H), 7.99 (d, 2H, J = 8.8 Hz), 7.78 (s, 1H), 7.45 (d, 2H, J = 8.8 Hz), 7.30 (s, 1H), 5.36-5.33 (m, 2H), 3.44-3.33 (m, 2H). MS m/z 367.20 (M + 1). | 8.7 | 0.91 | 4.3 |

TABLE 10-continued

| Structure | Spectroscopy | BaF3 | Bcr-Abl | T315I |
|---|---|---|---|---|
| | ¹H NMR 400 MHz (DMSO-d₆) δ 10.25 (s, 1H), 8.44 (s, 1H), 8.33 (s, 1H), 7.99 (d, 2H, J = 9.2 Hz), 7.41 (d, 2H, J = 9.2 Hz), 4.58-4.47 (m, 2H), 4.29-4.26 (m, 2H), 3.79-3.76 (m, 2H), 2.09-2.00 (m, 1H), 1.86-1.79 (m, 1H), 1.69-1.61 (m, 1H); MS m/z 380.22 (M + 1). | >10 | 0.69 | >10 |
| 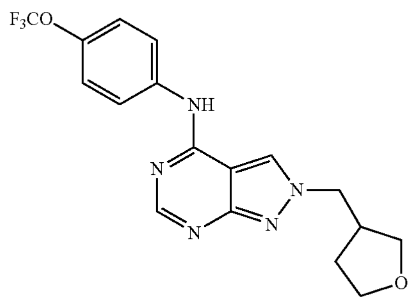 [SMILES: FC(F)(F)Oc1ccc(Nc2ncnc3nn(CC4CCOC4)cc23)cc1] | MS m/z 380.22 (M + 1). | >10 | 0.340 | 2.362 |
| 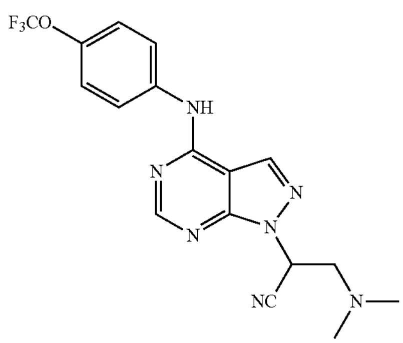 [SMILES: CN(C)CC(C#N)n1ncc2c(Nc3ccc(OC(F)(F)F)cc3)ncnc21] | MS m/z 392.12 (M + 1). | >10 | >10 | >10 |
| 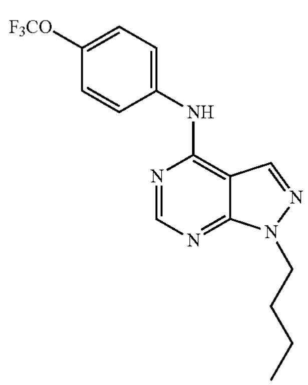 [SMILES: CCCCn1ncc2c(Nc3ccc(OC(F)(F)F)cc3)ncnc21] | MS m/z 352.20 (M + 1). | 6.6 | 0.27 | 1.5 |

TABLE 10-continued

| Structure | Spectroscopy | BaF3 | Bcr-Abl | T315I |
|---|---|---|---|---|
| [structure: F₃CO-phenyl-NH-pyrazolopyrimidine, 2-butyl] | MS m/z 352.14 (M + 1). | >10 | 0.160 | 2.4 |
| [structure: F₃CO-phenyl-NH-pyrazolopyrimidine, 1-t-butyl] | ¹H NMR 400 MHz (DMSO-d₆) δ 10.67 (s, 1H), 8.81 (s, 1H), 8.63 (s, 1H), 7.96 (d, 2H, J = 9.2 Hz), 7.47 (d, 2H, J = 9.2 Hz), 1.68 (s, 9H); (M + 1). MS m/z 352.20 (M + 1). | 7.3 | 0.16 | 2.6 |
| [structure: F₃CO-phenyl-NH-pyrazolopyrimidine, 1-CH₂CF₃] | MS m/z 378.31 (M + 1). | >10 | 0.308 | 2.9 |
| [structure: F₃CO-phenyl-NH-pyrazolopyrimidine, 2-CH₂CF₃] | MS m/z 378.30 (M + 1). | 8.00 | 0.570 | 2.4 |
| [structure: F₃CO-phenyl-NH-pyrazolopyrimidine, 1-benzyl] | MS m/z 386.10 (M + 1). | >10 | 0.4 | >10 |

TABLE 10-continued

| Structure | Spectroscopy | BaF3 | Bcr-Abl | T315I |
|---|---|---|---|---|
| 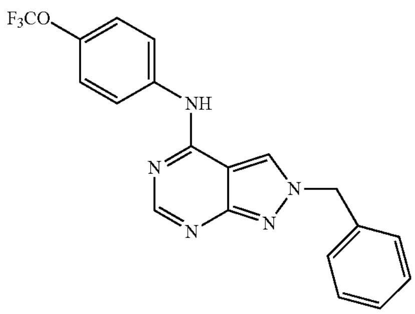 [SMILES: FC(F)(F)Oc1ccc(Nc2ncnc3nn(Cc4ccccc4)cc23)cc1] | MS m/z 386.10 (M + 1). | >10 | >10 | >10 |
| 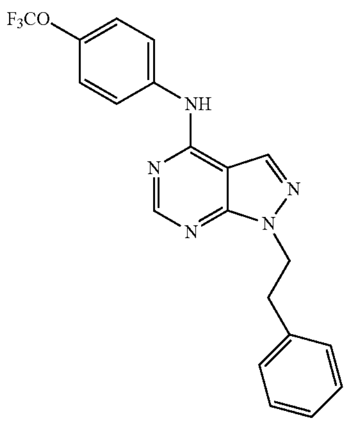 [SMILES: FC(F)(F)Oc1ccc(Nc2ncnc3c2cnn3CCc2ccccc2)cc1] | MS m/z 400.02 (M + 1). | >10 | 2.6 | 9.9 |
| 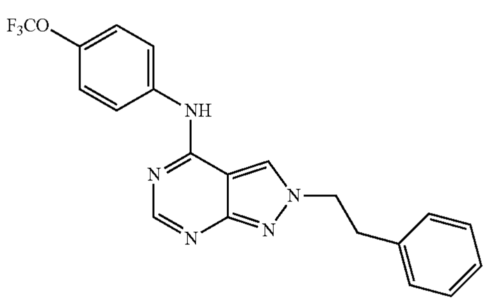 [SMILES: FC(F)(F)Oc1ccc(Nc2ncnc3nn(CCc4ccccc4)cc23)cc1] | MS m/z 400.10 (M + 1). | >10 | 3.7 | >10 |
| 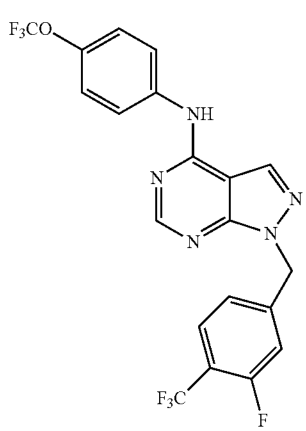 [SMILES: Fc1cc(Cn2ncc3c(Nc4ccc(OC(F)(F)F)cc4)ncnc32)ccc1C(F)(F)F] | MS m/z 472.21 (M + 1). | 6.7 | 1.26 | 4.5 |

TABLE 10-continued

| Structure | Spectroscopy | BaF3 | Bcr-Abl | T315I |
|---|---|---|---|---|
| (4-trifluoromethoxyphenyl)amino pyrazolopyrimidine with 2-(4-fluoro-3-trifluoromethyl)benzyl | MS m/z 472.18 (M + 1). | 4.6 | 2.38 | 5.2 |
| (4-trifluoromethoxyphenyl)amino pyrazolopyrimidine with 1-(3-bromobenzyl) | MS m/z 463.41 (M + 1). | >10 | >10 | >10 |
| (4-trifluoromethoxyphenyl)amino pyrazolopyrimidine with 2-(3-bromobenzyl) | MS m/z 463.41 (M + 1). | >10 | 7.2 | >10 |
| (4-trifluoromethoxyphenyl)amino pyrazolopyrimidine with 1-(3-hydroxybenzyl) | $^1$H NMR 400 MHz (DMSO-d$_6$) δ 10.69 (s, 1H), 8.79 (brs, 1H), 8.52 (s, 1H), 7.99 (d, 2H, J = 8.8 Hz), 7.44 (d, 2 H, J = 8.8 Hz), 7.42 (s, 1H), 6.45-6.39 (m, 3H), 5.63-5.59 (m, 2H); MS m/z 402.12 (M + 1). | 6.9 | 0.21 | 2.03 |

TABLE 10-continued
| Structure | Spectroscopy | BaF3 | Bcr-Abl | T315I |
|---|---|---|---|---|
| 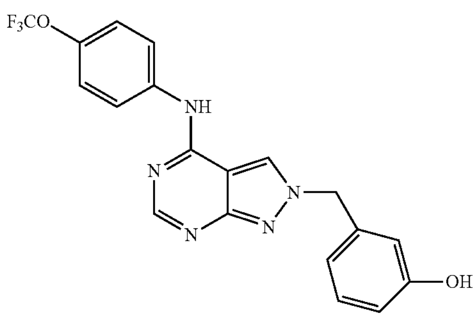 [SMILES: Oc1cccc(Cn2cc3c(Nc4ccc(OC(F)(F)F)cc4)ncnc3n2)c1] | MS m/z 402.02 (M + 1). | 6.9 | 0.16 | 1.5 |
| 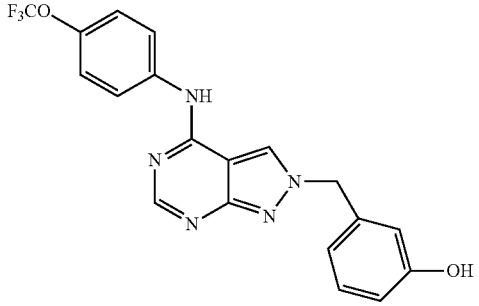 | | | | |
| | MS m/z 387.01 (M + 1). | 2.2 | 0.030 | 0.60 |
| 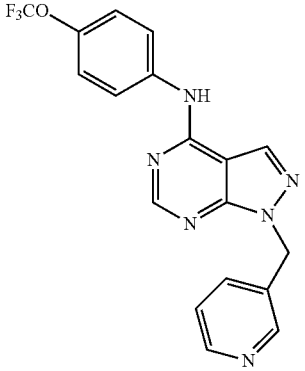 [SMILES: FC(F)(F)Oc1ccc(Nc2ncnc3c2cnn3Cc2cccnc2)cc1] | | | | |
| | MS m/z 387.01 (M + 1). | 2.1 | 0.122 | 1.3 |
| 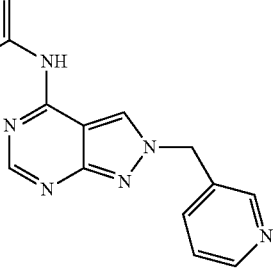 | | | | |
| 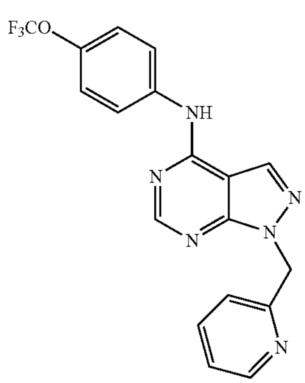 [SMILES: FC(F)(F)Oc1ccc(Nc2ncnc3c2cnn3Cc2ccccn2)cc1] | MS m/z 387.20 (M + 1). | >10 | 4.84 | >10 |
| 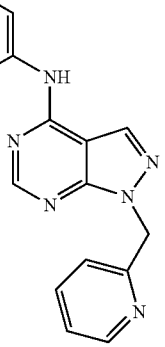 | | | | |

TABLE 10-continued

| Structure | Spectroscopy | BaF3 | Bcr-Abl | T315I |
|---|---|---|---|---|
| (structure) | MS m/z 387.10 (M + 1). | >10 | 0.824 | 5.4 |
| (structure) | MS m/z 469.13 (M + 1). | >10 | >10 | >10 |
| (structure) | MS m/z 339.12 (M + 1). | >10 | >10 | >10 |
| (structure) | $^1$H NMR 400 MHz (DMSO-d$_6$) δ 10.67 (s, 1H), 9.78 (s, 1H), 9.10 (s, 1H), 8.57 (s, 1H), 8.55-8.51 (m, 1H), 8.36 (d, 1H, J = 8.8 Hz), 8.08 (d, 2H, J = 9.2 Hz), 7.45 (d, 2H, J = 9.2 Hz). MS m/z 441.21 (M + 1). | >10 | 0.397 | 5.27 |

TABLE 10-continued

| Structure | Spectroscopy | BaF3 | Bcr-Abl | T315I |
|---|---|---|---|---|
| 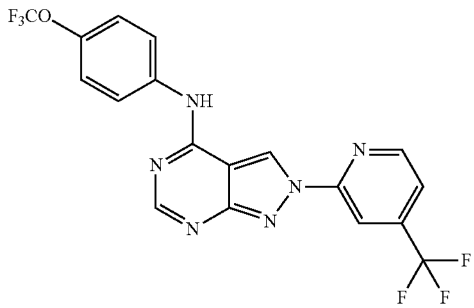 [SMILES: FC(F)(F)Oc1ccc(Nc2ncnc3nn(-c4cc(C(F)(F)F)ccn4)cc23)cc1] | MS m/z 441.20 (M + 1). | >10 | >10 | >10 |
| | MS m/z 400.13 (M + 1). | >10 | >10 | >10 |
| | MS m/z 400.13 (M + 1). | >10 | 0.487 | >10 |
| 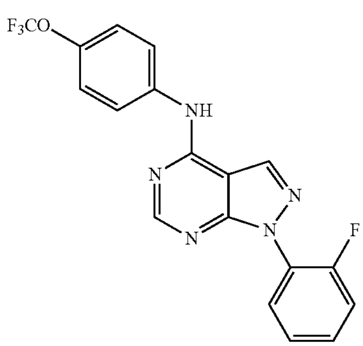 [SMILES: Fc1ccccc1-n1ncc2c(Nc3ccc(OC(F)(F)F)cc3)ncnc21] | $^1$H NMR 400 MHz (DMSO-d$_6$) δ 11.069 (s, 1H), 8.67 (s, 1H), 8.35 (s, 1H), 7.77 (d, 2H, J = 9.2 Hz), 7.38 (d, 2H, J = 9.2 Hz), 7.26-7.12 (m, 3H), 6.86-6.80 (m, 1H). MS m/z 390.22 (M + 1). | >10 | >10 | >10 |
| 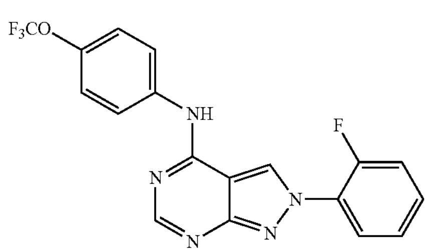 [SMILES: Fc1ccccc1-n1cc2c(Nc3ccc(OC(F)(F)F)cc3)ncnc2n1] | MS m/z 390.20 (M + 1). | '210 | 0.194 | >10 |

TABLE 10-continued

| Structure | Spectroscopy | BaF3 | Bcr-Abl | T315I |
|---|---|---|---|---|
| (F₃CO-phenyl-NH-pyrazolo[3,4-d]pyrimidine, N1-(2,4-dichlorophenyl)) | MS m/z 440.08 (M + 1). | >10 | >10 | >10 |
| (F₃CO-phenyl-NH-pyrazolo[3,4-d]pyrimidine, N2-(2,4-dichlorophenyl)) | MS m/z 440.08 (M + 1). | >10 | 3.37 | >10 |
| (F₃CO-phenyl-NH-pyrazolo[3,4-d]pyrimidine, N1-(2-ethylphenyl)) | MS m/z 400.16 (M + 1). | >10 | 2.49 | >10 |
| (F₃CO-phenyl-NH-pyrazolo[3,4-d]pyrimidine, N2-(2-ethylphenyl)) | MS m/z 400.06 (M + 1). | >10 | >10 | >10 |
| (F₃CO-phenyl-NH-pyrazolo[3,4-d]pyrimidine, N1-(2-pyridyl)) | MS m/z 372.02 (M + 1). | 7.0 | 0.246 | 4.5 |

TABLE 10-continued

| Structure | Spectroscopy | BaF3 | Bcr-Abl | T315I |
|---|---|---|---|---|
| (F₃CO-phenyl-NH-pyrazolo[3,4-d]pyrimidine-N-2-pyridyl) | MS m/z 372.20 (M + 1). | >10 | 0.195 | 3.534 |
| (F₃CO-phenyl-NH-pyrazolo[3,4-d]pyrimidine-N-phenyl-SO₂NH₂) | MS m/z 451.12 (M + 1). | 1.80 | 6.66 | >10 |

TABLE 11

| Structure | Spectroscopy | BaF3 | Bcr-Abl | T315I |
|---|---|---|---|---|
| (F₃CO-phenyl-NH-9-methylpurine) | $^1$H NMR 400 MHz (DMSO-d$_6$) δ 10.16 (s, 1H), 8.45 (s, 1H), 8.34 (s, 1H), 8.07 (d, 2H, J = 8.8 Hz), 7.34 (d, 2 H, J = 8.8 Hz), 3.81 (s, 3H). MS m/z 310.15 (M + 1). | >10 | >10 | >10 |
| (F₃CO-phenyl-NH-7-methylpurine) | MS m/z 310.14 (M + 1). | >10 | 7.69 | >10 |

TABLE 11-continued

| Structure | Spectroscopy | BaF3 | Bcr-Abl | T315I |
|---|---|---|---|---|
| [Structure: N6-(4-trifluoromethoxyphenyl)adenosine] | ¹H NMR 400 MHz (DMSO-d₆) δ 10.23 (s, 1H), 8.59 (s, 1H), 8.44 (s, 1H), 8.06 (d, 2H, J = 9.2 Hz), 7.35 (d, 2H, J = 9.2 Hz), 5.95-5.84 (m, 2H), 4.65 (t, 1H, J = 5.2 Hz), 4.18 (dd, 1H, J = 4.8, 3.2 Hz), 3.98 (dd, 1H, J = 6.8, 3.2 Hz), 3.70 (dd, 1H, J = 12.0, 4.0 Hz), 3.58 (dd, 1H, J = 12, 4.0 Hz). MS m/z 428.23 (M + 1). | >10 | 2.14 | >10 |
| [Structure: N6-(4-trifluoromethoxyphenyl)-9-(2-morpholinoethyl)adenine] | ¹H NMR 400 MHz (DMSO-d₆) δ 10.24 (s, 1H), 8.48 (s, 1H), 8.41 (s, 1H), 8.07 (d, 2H, J = 8.8 Hz), 7.36 (d, 2 H, J = 8.8 Hz), 5.42-5.39 (m, 2H), 4.59-4.42 (m, 6H), 2.60-2.42 (m, 4H). MS m/z 409.12 (M + 1). | >10 | 2.45 | >10 |

TABLE 12

| Structure | Spectroscopy | BaF3 | Bcr-Abl | T315I |
|---|---|---|---|---|
| [Structure: 7-deaza analog with ribose, N-(4-trifluoromethoxyphenyl)] | ¹H NMR 400 MHz (DMSO-d₆) δ 10.23 (s, 1H), 8.37 (s, 1H), 7.94 (d, 2H, J = 9.2 Hz), 7.64 (d, 1H, J = 4.0 Hz), 7.25 (d, 2H, J = 9.2 Hz), 6.90 (d, 1H, J = 4.0 Hz), 6.13 (d, 1H, J = 6.0 Hz), 4.43 (t, 1H, J = 5.2 Hz), 4.13 (dd, 1H, J = 4.8, 3.2 Hz), 3.94 (dd, 1H, J = 6.8, 3.2 Hz), 3.65 (dd, 1H, J = 12.0, 4.0 Hz), 3.56 (dd, 1H, J = 12, 4.0 Hz). MS m/z 427.10 (M + 1). | >10 | 5.5 | >10 |
| [Structure: N-(4-trifluoromethoxyphenyl)-7H-pyrrolo[2,3-d]pyrimidin-4-amine] | MS m/z 295.14 (M + 1). | >10 | >10 | >10 |

TABLE 12-continued

| Structure | Spectroscopy | BaF3 | Bcr-Abl | T315I |
|---|---|---|---|---|
| (structure: 4-(4-trifluoromethoxyphenylamino)-7-methyl-7H-pyrrolo[2,3-d]pyrimidine) | ¹H NMR 400 MHz (DMSO-d₆) δ 12.08 (s, 1H), 8.33 (s, 1H), 7.95 (d, 2H, J = 9.2 Hz), 7.39 (d, 2, H, J = 9.2 Hz), 7.34 (d, 1H, J = 6.2 Hz), 6.81 (d, 1H, J = 6.0 Hz), 3.36 (s, 3H). MS m/z 309.12 (M + 1). | >10 | 6.89 | >10 |
| (structure: 4-(4-trifluoromethoxyphenylamino)-7-(2-hydroxyethyl)-7H-pyrrolo[2,3-d]pyrimidine) | MS m/z 339.22 (M + 1). | >10 | 0.45 | 2.79 |
| (structure: 4-(4-trifluoromethoxyphenylamino)-7-(2-morpholinoethyl)-7H-pyrrolo[2,3-d]pyrimidine with OH) | ¹H NMR 400 MHz (DMSO-d₆) δ 9.06 (s, 1H), 8.80 (brs, 1H), 8.65 (d, 2H, J = 8.8 Hz), 7.82 (d, 2 H, J = 8.8 Hz), 7.46 (d, 1H, J = 6.2 Hz), 7.17 (d, 1H, J = 6.0 Hz), 5.41-5.39 (m, 2H), 4.43-4.36 (m, 6H), 2.52-2.31 (m, 4H). MS m/z 408.1 (M + 1). | >10 | 0.38 | 4.27 |
| (structure: 4-(4-trifluoromethoxyphenylamino)-7-(4-methoxybenzyl)-7H-pyrrolo[2,3-d]pyrimidine) | ¹H NMR 400 MHz (DMSO-d₆) δ 8.95 (s, 1H), 8.32 (d, 2H, J = 8.6 Hz), 7.89 (d, 2 H, J = 8.6 Hz), 7.81 (d, 1H, J = 6.2 Hz), 7.75 (m, 3H), 7.35 (d, 2H, J = 8.4 Hz), 5.89 (s, 2H), 4.22 (s, 3H). MS m/z 415.1 (M + 1). | >10 | 9.68 | >10 |
| (structure: 4-(4-trifluoromethoxyphenylamino)-7-(2-carbamoylethyl)-7H-pyrrolo[2,3-d]pyrimidine) | ¹H NMR 400 MHz (DMSO-d₆) δ 8.94 (s, 1H), 8.22 (brs, 1H), 7.94 (d, 2H, J = 8.8 Hz), 7.81 (d, 2 H, J = 8.8 Hz), 7.46 (d, 1H, J = 6.2 Hz), 7.18 (d, 1H, J = 6.0 Hz), 5.02 (t, 2H, J = 6.8 Hz), 3.25 (t, 2H, J = 6.8 Hz). MS m/z 366.2 (M + 1). | >10 | 0.49 | 6.42 |

TABLE 12-continued

| Structure | Spectroscopy | BaF3 | Bcr-Abl | T315I |
|---|---|---|---|---|
| 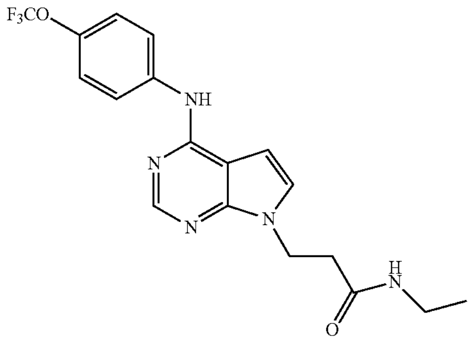 [SMILES: CCNC(=O)CCn1ccc2c(Nc3ccc(OC(F)(F)F)cc3)ncnc21] | MS m/z 394.10 (M + 1). | >10 | 2.42 | 9.29 |
| 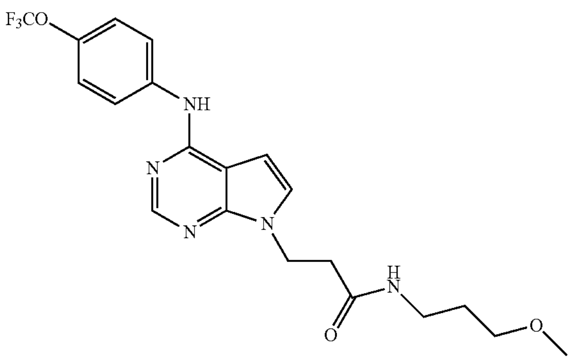 [SMILES: COCCCNC(=O)CCn1ccc2c(Nc3ccc(OC(F)(F)F)cc3)ncnc21] | MS m/z 438.04 (M + 1). | >10 | 3.26 | >10 |
| 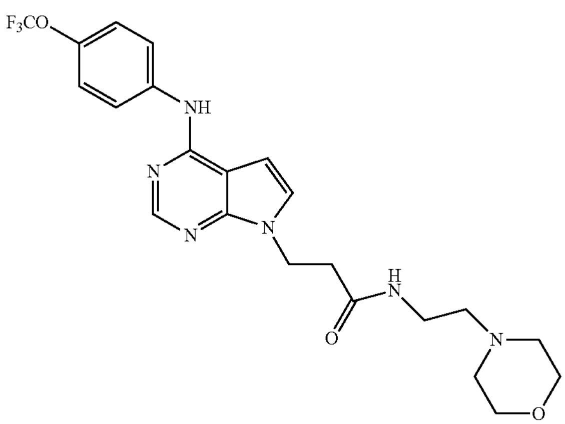 [SMILES: O=C(CCn1ccc2c(Nc3ccc(OC(F)(F)F)cc3)ncnc21)NCCN1CCOCC1] | MS m/z 479.20 (M + 1). | >10 | 1.06 | 3.14 |
| 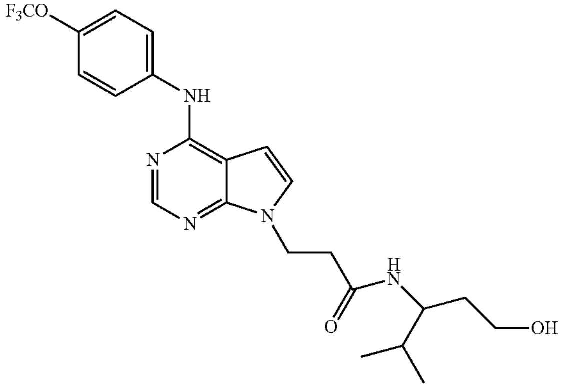 [SMILES: CC(C)C(CCO)NC(=O)CCn1ccc2c(Nc3ccc(OC(F)(F)F)cc3)ncnc21] | MS m/z 466.15 (M + 1). | >10 | 0.86 | 2.07 |

TABLE 12-continued
| Structure | Spectroscopy | BaF3 | Bcr-Abl | T315I |
|---|---|---|---|---|
| 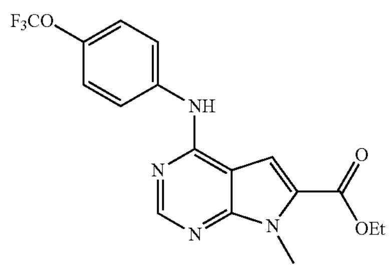 [SMILES: CCOC(=O)c1cc2c(Nc3ccc(OC(F)(F)F)cc3)ncnc2n1C] | MS m/z 381.10 (M + 1). | >10 | 1.5 | >10 |
| 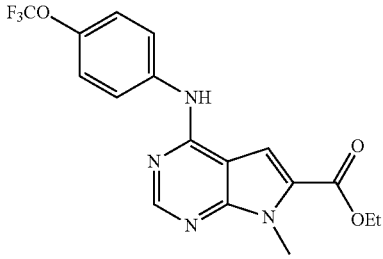 | MS m/z 498.20 (M + 1). | >10 | 1.98 | >10 |
| 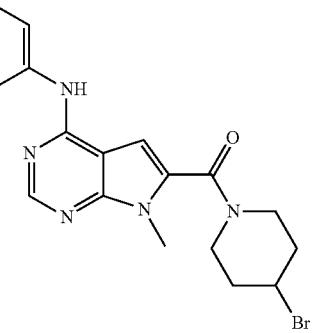 | MS m/z 463.12 (M + 1). | >10 | 0.82 | >10 |
| 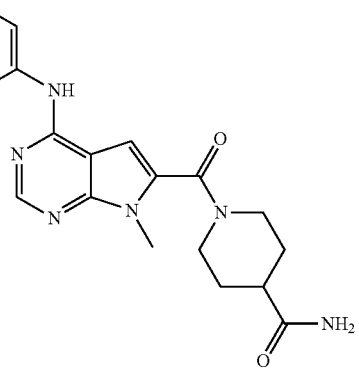 | MS m/z 463.20 (M + 1). | >10 | 1.98 | >10 |
| 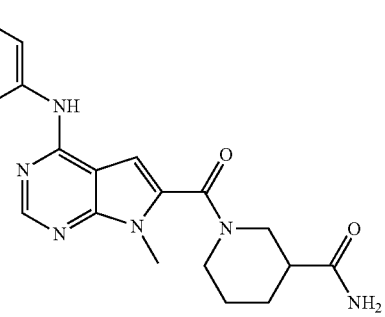 | | | | |

TABLE 12-continued

| Structure | Spectroscopy | BaF3 | Bcr-Abl | T315I |
|---|---|---|---|---|
| 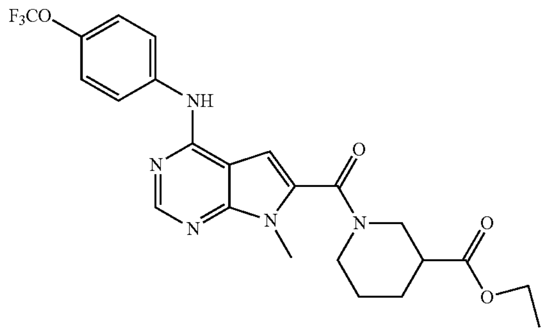 [SMILES: CCOC(=O)C1CCCN(C(=O)c2cc3c(Nc4ccc(OC(F)(F)F)cc4)ncnc3n2C)C1] | MS m/z 492.22 (M + 1). | >10 | 6.34 | >10 |
| 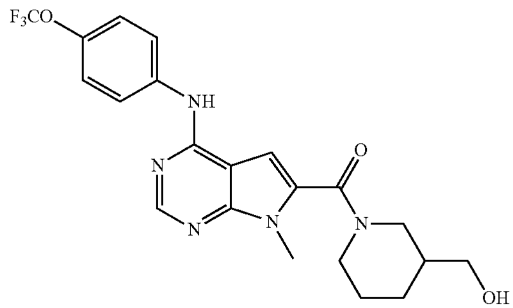 [SMILES: Cn1c(C(=O)N2CCCC(CO)C2)cc2c(Nc3ccc(OC(F)(F)F)cc3)ncnc21] | MS m/z 450.10 (M + 1). | 7.29 | 1.732 | >10 |
| 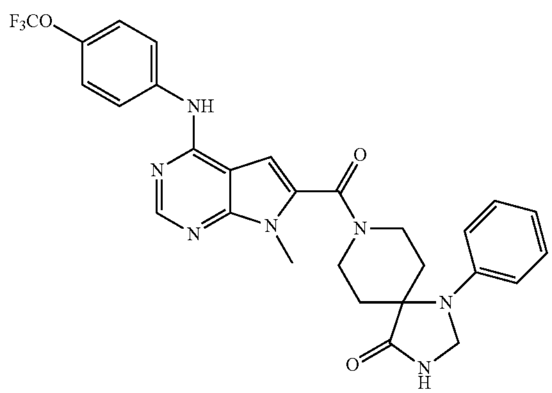 [SMILES: Cn1c(C(=O)N2CCC3(CC2)C(=O)NCN3c2ccccc2)cc2c(Nc3ccc(OC(F)(F)F)cc3)ncnc21] | MS m/z 566.15 (M + 1). | >10 | 6.18 | >10 |
| 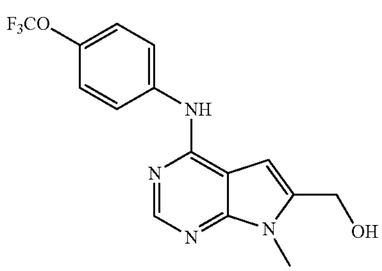 [SMILES: Cn1c(CO)cc2c(Nc3ccc(OC(F)(F)F)cc3)ncnc21] | MS m/z 339.10 (M + 1). | >10 | 0.245 | >10 |
| 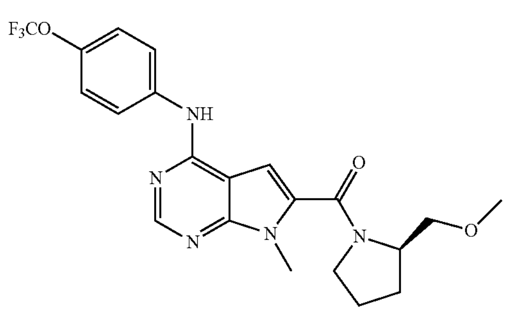 [SMILES: COC[C@H]1CCCN1C(=O)c1cc2c(Nc3ccc(OC(F)(F)F)cc3)ncnc2n1C] | MS m/z 450.14 (M + 1). | >10 | 2.18 | >10 |

TABLE 12-continued

| Structure | Spectroscopy | BaF3 | Bcr-Abl | T315I |
|---|---|---|---|---|
| (F₃CO-phenyl-NH-pyrrolopyrimidine-N-methyl-carboxamide) | MS m/z 352.01 (M + 1). | >10 | 0.620 | >10 |
| (F₃CO-phenyl-NH-pyrrolopyrimidine-N-methyl-N-ethylcarboxamide) | ¹H NMR 400 MHz (DMSO-d₆) δ 9.86 (s, 1H), 8.42 (s, 1H), 8.02 (d, 2H, J = 9.2 Hz), 7.37 (d, 2 H, J = 9.2 Hz), 3.29 (pent, 2H, J = 6.8 Hz)), 1.14 (t, 3H, J = 7.2 Hz). MS m/z 380.12 (M + 1). | 5.37 | 0.450 | 6.93 |
| (F₃CO-phenyl-NH-pyrrolopyrimidine-N-methyl-N-(1-ethylpyrrolidin-2-yl)carboxamide) | MS m/z 449.02 (M + 1). | 5.12 | 2.95 | 8.47 |
| (F₃CO-phenyl-NH-pyrrolopyrimidine-N-methyl-guanidinocarboxamide) | ¹H NMR 400 MHz (DMSO-d₆) δ 9.83 (s, 1H), 8.46 (s, 1H), 8.02 (d, 2H, J = 8.8 Hz), 7.68 (s, 1H), 7.37 (d, 2 H, J = 8.8 Hz), 3.91 (s, 3H); MS m/z 394.10 (M + 1). | >10 | >10 | >10 |
| (F₃CO-phenyl-NH-pyrrolopyrimidine-N-methyl-N-(5-(diethylamino)pentan-2-yl)carboxamide) | MS m/z 493.10 (M + 1). | 4.12 | 1.18 | 4.00 |

TABLE 13

| Structure | Spectroscopy | BaF3 | Bcr-Abl | T315I |
|---|---|---|---|---|
| 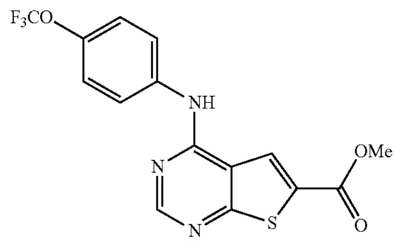 [SMILES: COC(=O)c1cc2c(Nc3ccc(OC(F)(F)F)cc3)ncnc2s1] | MS m/z 370.05 (M + 1). | >10 | 5.6 | >10 |
| 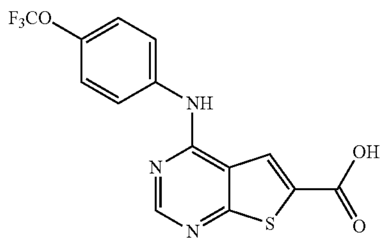 [SMILES: O=C(O)c1cc2c(Nc3ccc(OC(F)(F)F)cc3)ncnc2s1] | MS m/z 356.10 (M + 1). | >10 | >10 | >10 |
| 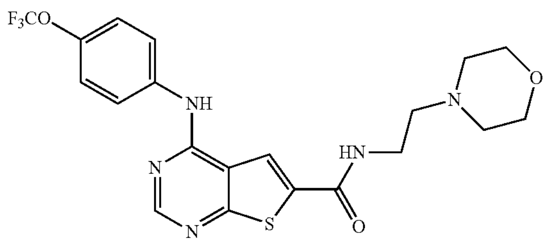 [SMILES: O=C(NCCN1CCOCC1)c1cc2c(Nc3ccc(OC(F)(F)F)cc3)ncnc2s1] | MS m/z 468.12 (M + 1). | >10 | 5.2 | >10 |
| 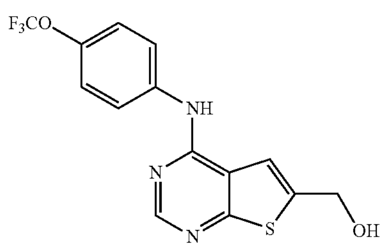 [SMILES: OCc1cc2c(Nc3ccc(OC(F)(F)F)cc3)ncnc2s1] | $^1$H NMR 400 MHz (DMSO-$d_6$) δ 10.29 (s, 1H), 8.45 (s, 1H), 7.91 (d, 2H, J = 9.6 Hz), 7.21 (d, 2H, J = 9.6 Hz), 6.59 (s, 1H), 4.80 (s, 2H). MS m/z 342.12 (M + 1). | >10 | 0.33 | 3.7 |
| 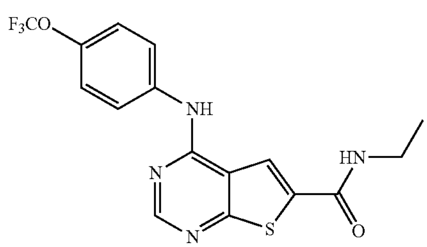 [SMILES: CCNC(=O)c1cc2c(Nc3ccc(OC(F)(F)F)cc3)ncnc2s1] | $^1$H NMR 400 MHz (DMSO-$d_6$) δ 10.39 (s, 1H), 8.55 (s, 1H), 7.,94 (d, 2H, J = 9.6 Hz), 7.31 (d, 2H, J = 9.6 Hz), 6.60 (s, 1H), 3.23 (q, 2H, J = 3.2 Hz), 1.78 (t, 3H, J = 3.3 Hz). MS m/z 383.10 (M + 1). | >10 | 0.918 | >10 |
| 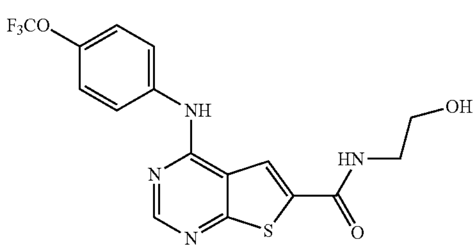 [SMILES: O=C(NCCO)c1cc2c(Nc3ccc(OC(F)(F)F)cc3)ncnc2s1] | $^1$H NMR 400 MHz (DMSO-$d_6$) δ 10.10 (s, 1H), 9.26 (s, 1H), 8.82 (s, 1H), 8.21 (d, 2H, J = 8.8 Hz), 7.85 (d, 2H, J = 8.8 Hz), 7.34 (s, 1H), 3.02 (t, 2H, J = 6.4 Hz), 2.65 (t, 2H, J = 6.4 Hz). MS m/z 399.12 (M + 1). | >10 | >10 | >10 |

TABLE 13-continued

| Structure | Spectroscopy | BaF3 | Bcr-Abl | T315I |
|---|---|---|---|---|
| 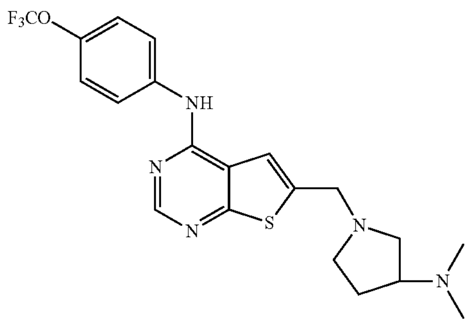 [SMILES: CN(C)C1CCN(Cc2cc3c(Nc4ccc(OC(F)(F)F)cc4)ncnc3s2)C1] | MS m/z 438.02 (M + 1). | >10 | 7.45 | >10 |
| 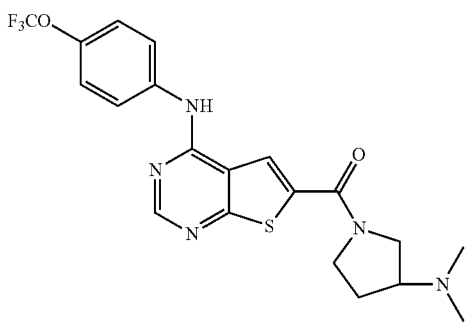 [SMILES: CN(C)C1CCN(C(=O)c2cc3c(Nc4ccc(OC(F)(F)F)cc4)ncnc3s2)C1] | MS m/z 452.11 (M + 1). | >10 | 0.764 | >10 |
| 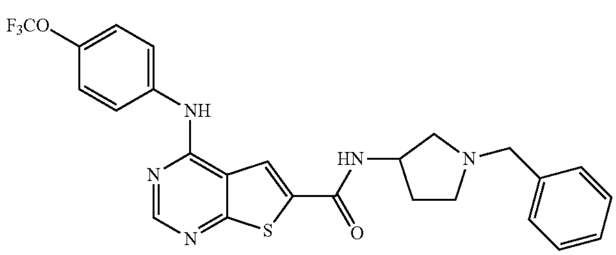 [SMILES: O=C(NC1CCN(Cc2ccccc2)C1)c1cc2c(Nc3ccc(OC(F)(F)F)cc3)ncnc2s1] | MS m/z 514.02 (M + 1). | 0.926 | 0.801 | 0.621 |
| 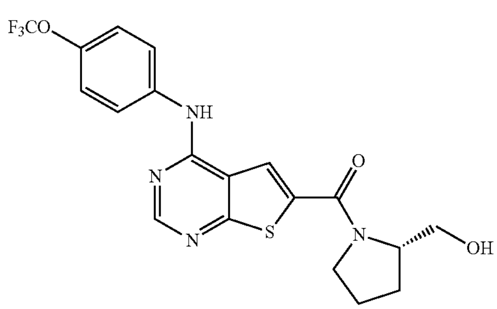 [SMILES: O=C(c1cc2c(Nc3ccc(OC(F)(F)F)cc3)ncnc2s1)N1CCC[C@H]1CO] | MS m/z 439.20 (M + 1). | 3.66 | 0.116 | 1.208 |
| 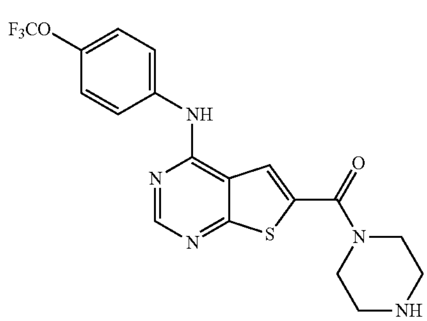 [SMILES: O=C(c1cc2c(Nc3ccc(OC(F)(F)F)cc3)ncnc2s1)N1CCNCC1] | MS m/z 424.22 (M + 1). | 4.065 | 0.406 | 2.3 |

TABLE 13-continued

| Structure | Spectroscopy | BaF3 | Bcr-Abl | T315I |
|---|---|---|---|---|
| | ¹H NMR 400 MHz (DMSO-d₆) δ 10.05 (s, 1H), 9.89 (brs, 1H), 8.59 (s, 1H), 8.22 (s, 1H), 7.94 (d, 2H, J = 9.2 Hz), 7.42 (d, 2H, J = 9.2 Hz), 4.47-4.45 (m, 4H), 3.55-3.54 (m, 4H)), 3.15-3.11 (m, 2H), 2.19-2.00 (m, 2H), 1.88-1.85 (m, 2H). MS m/z 493.16 (M + 1). | 5.77 | 1.34 | 3.96 |
| 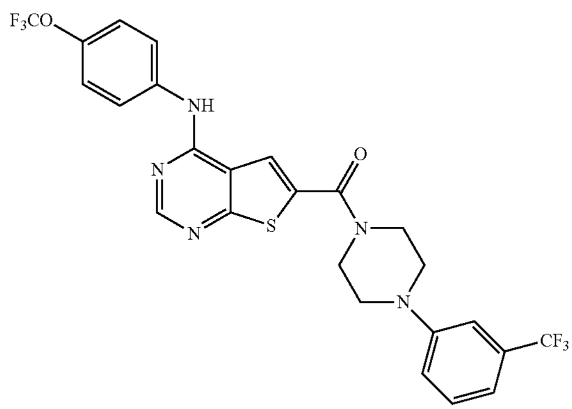 [SMILES: O=C(c1cc2c(Nc3ccc(OC(F)(F)F)cc3)ncnc2s1)N1CCN(c2cccc(C(F)(F)F)c2)CC1] | MS m/z 568.11 (M + 1). | 4.55 | 1.39 | 1.92 |
| | ¹H NMR 400 MHz (DMSO-d₆) δ 10.14 (s, 1H), 9.69 (brs, 1H), 8.61 (s, 1H), 8.55 (s, 1H), 8.00 (d, 2H, J = 8.8 Hz), 7.42 (d, 2H, J = 8.8 Hz), 4.02-4.00 (m, 2H), 3.69-3.65 (m, 2H)), 3.35-3.32 (m, 2H), 3.32-3.16 (m, 2H). MS m/z 468.20 (M + 1). | >10 | 3.2 | >10 |
| 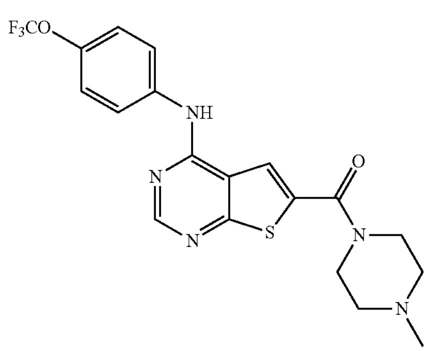 [SMILES: CN1CCN(C(=O)c2cc3c(Nc4ccc(OC(F)(F)F)cc4)ncnc3s2)CC1] | MS m/z 438.10 (M + 1). | 2.69 | 0.048 | 1.25 |

TABLE 13-continued

| Structure | Spectroscopy | BaF3 | Bcr-Abl | T315I |
|---|---|---|---|---|
| (structure) | ¹H NMR 400 MHz (DMSO-d₆) δ 10.76 (s, 1H), 9.32 (s, 1H), 8.86 (s, 1H), 7.94 (d, 2H, J = 8.8 Hz), 7.48 (d, 2H, J = 8.8 Hz), 4.69 (brs, 1H), 3.69-3.64 (m, 2H)), 3.45-3.43 (m, 2H), 3.21-3.15 (m, 2H), 2.86-2.84 (m, 2H). MS m/z 439.10 (M + 1). | >10 | 1.96 | >10 |
| (structure) | MS m/z 453.11 (M + 1). | >10 | 1.94 | >10 |
| (structure) | ¹H NMR 400 MHz (DMSO-d₆) δ 10.55 (s, 1H), 10.35 (s, 1H), 10.15 (s, 1H) 8.61 (d, 2H, J = 4.4 Hz), 8.18 (s, 1H), 8.13 (d, 1H, J = 9.2 Hz), 7.99 (d, 2 H, J = 8.8 Hz), 7.89 (d, 1H, J = 2.4 Hz), 7.61 (dd, 1H, J = 8.4, 2.0 Hz) 7.43 (d, 2H, J = 8.8 Hz), 7.31 (d, 1H, J = 8.8 Hz), 2.50 (s, 3H). m/z 632.21 (M + 1). | 8.9 | 1.44 | 2.1 |
| (structure) | MS m/z 312.12 (M + 1). | >10 | 3.679 | >10 |

TABLE 13-continued

| Structure | Spectroscopy | BaF3 | Bcr-Abl | T315I |
|---|---|---|---|---|
| F₃CO-C₆H₄-NH-thieno[2,3-d]pyrimidine-6-methyl | MS m/z 326.15 (M + 1). | >10 | 2.54 | >10 |

TABLE 14

| Structure | Spectroscopy | BaF3 | Bcr-Abl | T315I |
|---|---|---|---|---|
| F₃CO-C₆H₄-NH-quinazolin-7-yl methyl ester | MS m/z 364.10 (M + 1). | 6.62 | 0.214 | 1.912 |
| F₃CO-C₆H₄-NH-quinazolin-7-yl-CH₂OH | MS m/z 336.12 (M + 1). | >10 | 0.508 | >10 |
| F₃CO-C₆H₄-NH-quinazolin-7-yl-CH₂-N(Et)₂ | MS m/z 391.04 (M + 1). | >10 | 2.04 | >10 |
| F₃CO-C₆H₄-NH-quinazolin-7-yl-C(O)-N(Et)₂ | MS m/z 405.10 (M + 1). | >10 | 0.742 | 3.17 |

TABLE 14-continued

| Structure | Spectroscopy | BaF3 | Bcr-Abl1 | T315I |
|---|---|---|---|---|
| 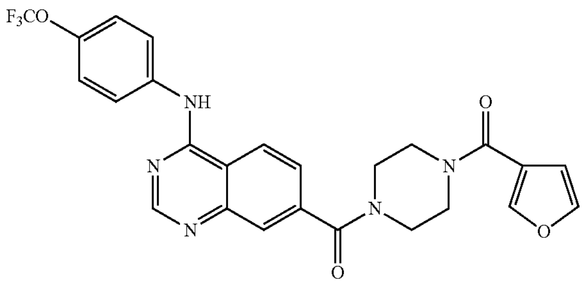 [SMILES: O=C(c1ccoc1)N1CCN(C(=O)c2ccc3c(Nc4ccc(OC(F)(F)F)cc4)ncnc3c2)CC1] | MS m/z 512.11 (M + 1). | >10 | 2.04 | 3.90 |
| 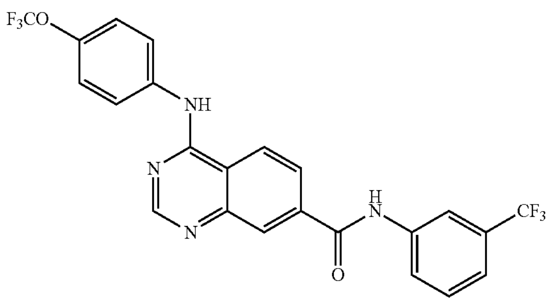 [SMILES: O=C(Nc1cccc(C(F)(F)F)c1)c1ccc2c(Nc3ccc(OC(F)(F)F)cc3)ncnc2c1] | MS m/z 493.10 (M + 1). | 4.50 | 1.276 | 1.558 |
| 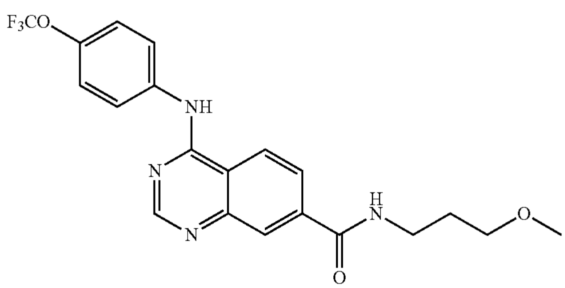 [SMILES: COCCCNC(=O)c1ccc2c(Nc3ccc(OC(F)(F)F)cc3)ncnc2c1] | MS m/z 421.02 (M + 1). | >10 | 4.089 | >10 |
| 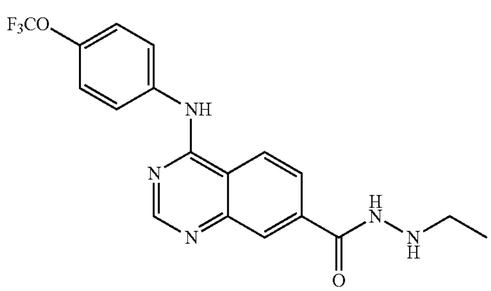 [SMILES: CCNNC(=O)c1ccc2c(Nc3ccc(OC(F)(F)F)cc3)ncnc2c1] | MS m/z 392.12 (M + 1). | 6.512 | 1.882 | 6.303 |
| 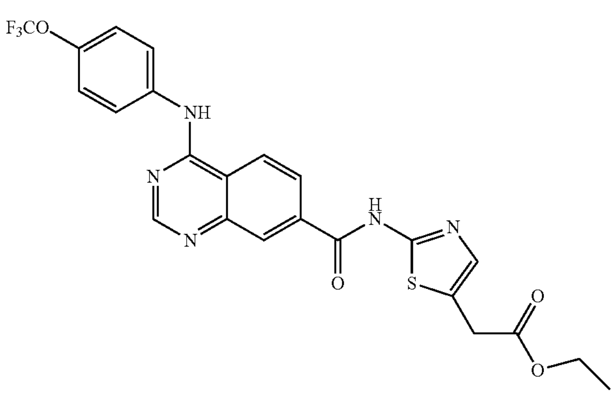 [SMILES: CCOC(=O)Cc1cnc(NC(=O)c2ccc3c(Nc4ccc(OC(F)(F)F)cc4)ncnc3c2)s1] | MS m/z 518.10 (M + 1). | >10 | 3.028 | 4.151 |

TABLE 14-continued

| Structure | Spectroscopy | BaF3 | Bcr-Abl | T315I |
|---|---|---|---|---|
| 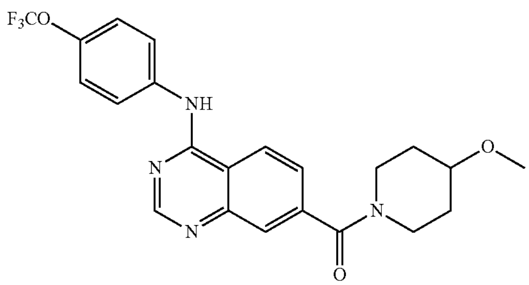 [SMILES: COC1CCN(C(=O)c2ccc3c(Nc4ccc(OC(F)(F)F)cc4)ncnc3c2)CC1] | MS m/z 447.18 (M + 1). | >10 | 0.639 | 0.895 |
| 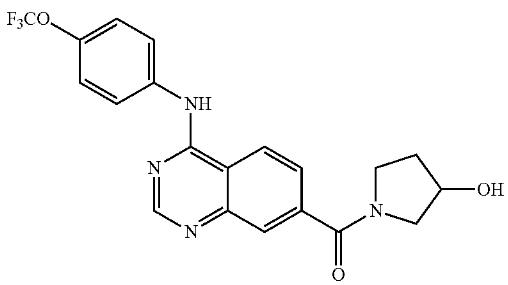 [SMILES: O=C(c1ccc2c(Nc3ccc(OC(F)(F)F)cc3)ncnc2c1)N1CCC(O)C1] | MS m/z 419.06 (M + 1). | >10 | 1.17 | >10 |
| 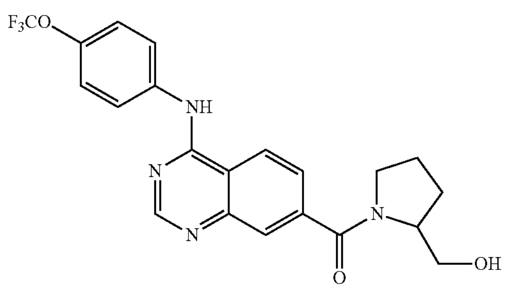 [SMILES: O=C(c1ccc2c(Nc3ccc(OC(F)(F)F)cc3)ncnc2c1)N1CCCC1CO] | MS m/z 433.20 (M + 1). | >10 | 1.65 | >10 |
| 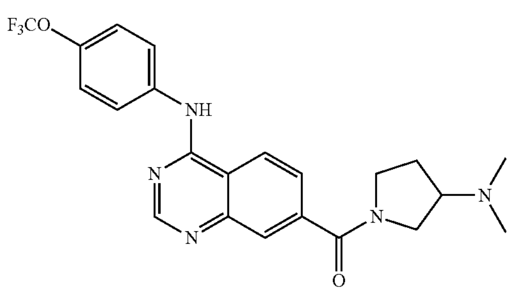 [SMILES: CN(C)C1CCN(C(=O)c2ccc3c(Nc4ccc(OC(F)(F)F)cc4)ncnc3c2)C1] | MS m/z 446.10 (M + 1). | >10 | 2.76 | >10 |
| 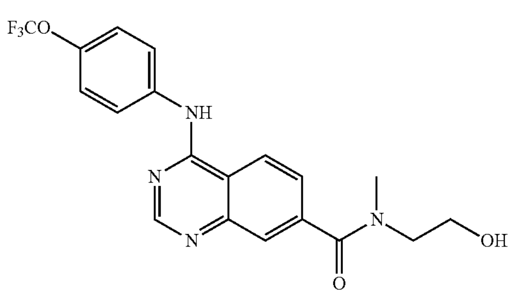 | MS m/z 407.12 (M + 1). | >10 | 2.664 | >10 |

TABLE 14-continued

| Structure | Spectroscopy | BaF3 | Bcr-Abl | T315I |
|---|---|---|---|---|
| 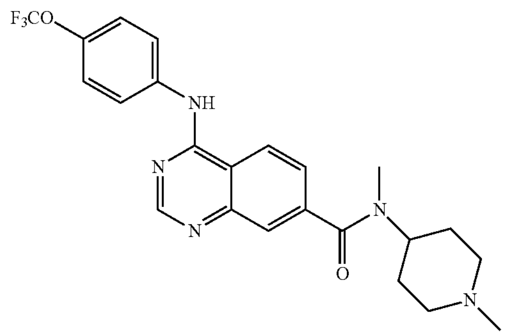 [SMILES: CN1CCC(N(C)C(=O)c2ccc3c(Nc4ccc(OC(F)(F)F)cc4)ncnc3c2)CC1] | MS m/z 460.06 (M + 1). | 5.99 | 0.689 | 4.997 |
| 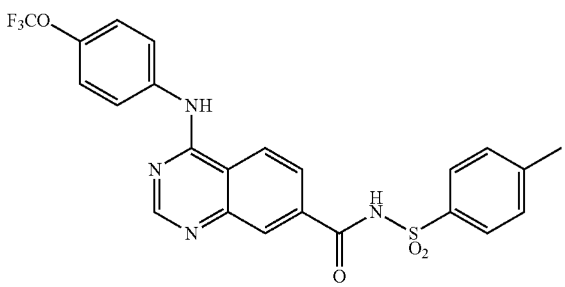 [SMILES: Cc1ccc(S(=O)(=O)NC(=O)c2ccc3c(Nc4ccc(OC(F)(F)F)cc4)ncnc3c2)cc1] | MS m/z 503.17 (M + 1). | >10 | >10 | >10 |
| 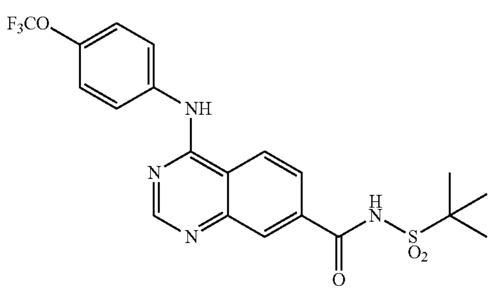 [SMILES: CC(C)(C)S(=O)(=O)NC(=O)c1ccc2c(Nc3ccc(OC(F)(F)F)cc3)ncnc2c1] | MS m/z 469.21 (M + 1). | >10 | >10 | >10 |
| 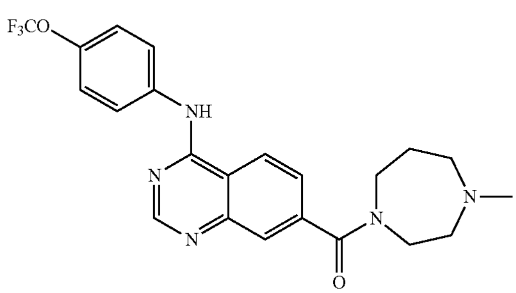 [SMILES: CN1CCCN(C(=O)c2ccc3c(Nc4ccc(OC(F)(F)F)cc4)ncnc3c2)CC1] | MS m/z 446.13 (M + 1). | 6.977 | 5.782 | >10 |
| 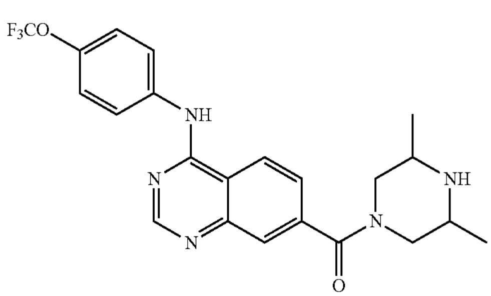 [SMILES: CC1CN(C(=O)c2ccc3c(Nc4ccc(OC(F)(F)F)cc4)ncnc3c2)CC(C)N1] | MS m/z 446.17 (M + 1). | 7.618 | 2.136 | >10 |

TABLE 14-continued

| Structure | Spectroscopy | BaF3 | Bcr-Abl1 | T315I |
|---|---|---|---|---|
| 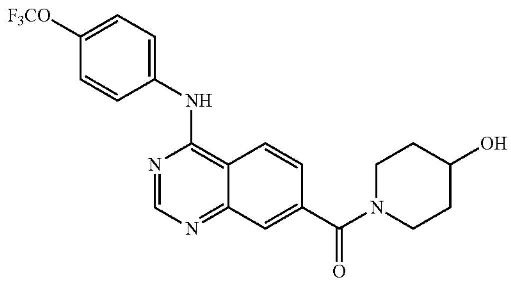 [SMILES: O=C(c1ccc2c(Nc3ccc(OC(F)(F)F)cc3)ncnc2c1)N1CCC(O)CC1] | MS m/z 433.10 (M + 1). | >10 | 1.95 | >10 |
| 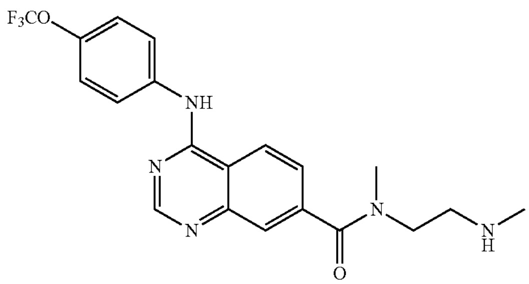 [SMILES: CNCCN(C)C(=O)c1ccc2c(Nc3ccc(OC(F)(F)F)cc3)ncnc2c1] | MS m/z 420.12 (M + 1). | >10 | 5.98 | >10 |
| 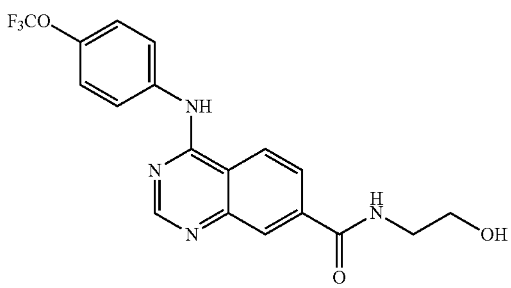 | MS m/z 393.04 (M + 1). | >10 | 2.15 | >10 |
| 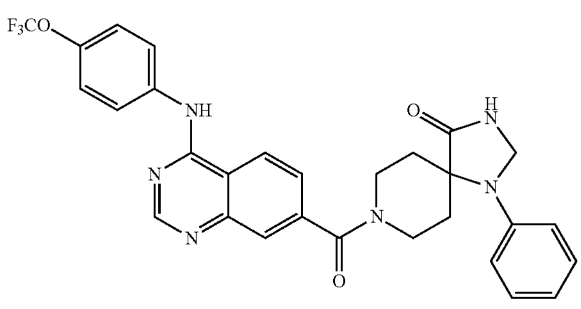 [SMILES: O=C(c1ccc2c(Nc3ccc(OC(F)(F)F)cc3)ncnc2c1)N1CCC2(CC1)C(=O)NCN2c1ccccc1] | MS m/z 563.20 (M + 1). | 6.89 | 1.48 | 8.321 |
| 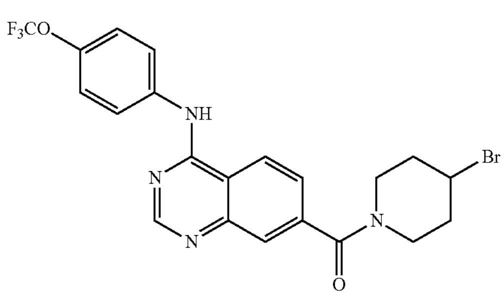 [SMILES: O=C(c1ccc2c(Nc3ccc(OC(F)(F)F)cc3)ncnc2c1)N1CCC(Br)CC1] | MS m/z 495.23 (M + 1). | 7.42 | 3.87 | >10 |

TABLE 14-continued

| Structure | Spectroscopy | BaF3 | Bcr-Abl | T315I |
|---|---|---|---|---|
| (F₃CO-phenyl-NH-quinazoline-C(O)-piperidine-4-C(O)NH₂) | ¹H NMR 400 MHz (DMSO-d₆) δ 11.16 (s, 1H), 8.92 (s, 1H), 8.75 (d, 1H, J = 8.4 Hz), 7.90 (d, 2H, J = 9.2 Hz), 7.82 (s, 1H), 7.84-7.81 (m, 1H), 7.50 (d, 2H, J = 9.2 Hz), 4.50-4.47 (m, 1H), 3.53-3.44 (m, 4H)), 1.85-1.65 (m, 4H). MS m/z 460.21 (M + 1). | >10 | 6.21 | >10 |
| (F₃CO-phenyl-NH-quinazoline-C(O)-piperidine-3-C(O)NH₂) | MS m/z 460.20 (M + 1). | >10 | 3.09 | >10 |
| (F₃CO-phenyl-NH-quinazoline-C(O)-piperidine-3-CO₂Et) | MS m/z 489.09 (M + 1). | 8.841 | 5.552 | >10 |
| (F₃CO-phenyl-NH-quinazoline-C(O)-piperidine-3-CH₂OH) | ¹H NMR 400 MHz (DMSO-d₆) δ 11.21 (s, 1H), 8.92 (s, 1H), 8.75 (d, 1H, J = 8.8 Hz), 8.55 (s, 1H), 7.89 (d, 2H, J = 9.2 Hz), 7.84-7.81 (m, 1H), 7.51 (d, 2H, J = 9.2 Hz), 4.37-4.16 (m, 2H), 4.14-3.99 (m, 4H)), 1.71-1.12 (m, 1H), 1.23-1.11 (m, 4H). MS m/z 447.12 (M + 1). | >10 | 1.67 | >10 |

TABLE 15

| Structure | Spectroscopy | BaF3 | Bcr-Abl | T315I |
|---|---|---|---|---|
| (F₃CO-phenyl-NH-pyrrolopyrimidinone) | MS m/z 311.03 (M + 1). | >10 | >10 | >10 |

TABLE 15-continued

| Structure | Spectroscopy | BaF3 | Bcr-Abl | T315I |
|---|---|---|---|---|
| (F₃CO-phenyl-NH-pyrrolo[2,3-d]pyrimidin-6(7H)-one, 7-methyl) | MS m/z 325.07 (M + 1). | >10 | >10 | >10 |

TABLE 16

| Structure | Spectroscopy | BaF3 | Bcr-Abl | T315I |
|---|---|---|---|---|
| (4-OCF₃-phenyl-NH-pyrimidine-phenyl-SO₂NH₂) | ¹H NMR 400 MHz (DMSO-d₆) δ 10.24 (s, 1H), 8.61 (s, 1H), 8.01 (d, 2H, J = 8.8 Hz), 7.86 (d, 2 H, J = 8.4 Hz), 7.65 (d, 2H, J = 8.8 Hz), 7.72 (t, 1H, J = 6 Hz), 7.22 (d, 2H, J = 8.4 Hz), 7.12 (d, 2H, J = 8.4 Hz), 7.04 (m, 1H), 5.6 (brs, 1H). MS m/z 411.15 (M + 1). | >10 | 0.120 | 1.05 |
| (4-OCF₃-phenyl-NH-5-methylpyrimidine-phenyl-SO₂NH₂) | MS m/z 425.10 (M + 1). | >10 | 0.73 | 6.77 |
| (4-OCF₃-phenyl-NH-5-methylpyrimidine-phenyl-SO₂NHCH₃) | MS m/z 439.40 (M + 1). | 2.5 | 0.27 | 2.13 |

TABLE 16-continued

| Structure | Spectroscopy | BaF3 | Bcr-Abl | T315I |
|---|---|---|---|---|
| 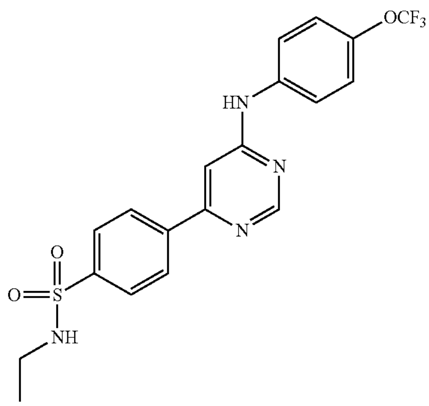 [SMILES: CCNS(=O)(=O)c1ccc(-c2cc(Nc3ccc(OC(F)(F)F)cc3)ncn2)cc1] | MS m/z 439.20 (M + 1). | >10 | 0.22 | 1.85 |
| 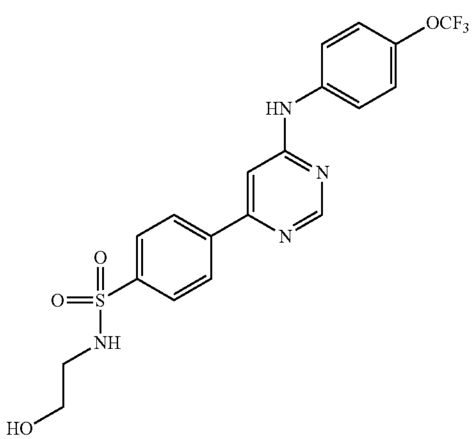 [SMILES: O=S(=O)(NCCO)c1ccc(-c2cc(Nc3ccc(OC(F)(F)F)cc3)ncn2)cc1] | $^1$H NMR 400 MHz (DMSO-d$_6$) δ 10.15 (s, 1H), 8.81 (s, 1H), 8.21 (d, 2H, J = 8.8 Hz), 7.96 (d, 2 H, J = 8.4 Hz), 7.85 (d, 2H, J = 8.8 Hz), 7.77 (t, 1H, J = 6 Hz), 7.35 (d, 2H, J = 8.4 Hz), 7.38 (d, 2H, J = 8.4 Hz), 7.34 (m, 1H), 5.10 (brs, 1H), 3.39 (t, 2H, J = 6.4 Hz), 2.85 (t, 2H, J = 6.4 Hz). MS m/z 455.10 (M + 1). | >10 | 0.21 | 1.45 |
| 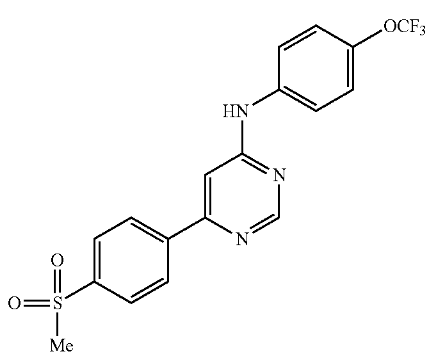 [SMILES: CS(=O)(=O)c1ccc(-c2cc(Nc3ccc(OC(F)(F)F)cc3)ncn2)cc1] | MS m/z 410.05 (M + 1). | >10 | 0.26 | 6.10 |
| 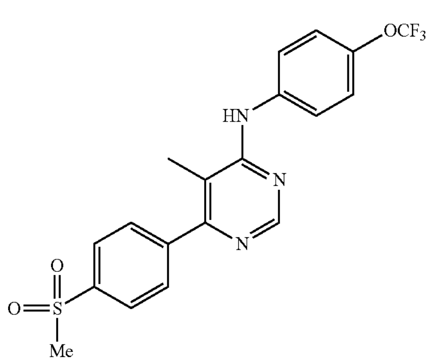 [SMILES: Cc1c(Nc2ccc(OC(F)(F)F)cc2)ncnc1-c1ccc(S(C)(=O)=O)cc1] | MS m/z 425.21 (M + 1). | >10 | 1.93 | >10 |

TABLE 16-continued
| Structure | Spectroscopy | BaF3 | Bcr-Abl | T315I |
|---|---|---|---|---|
| 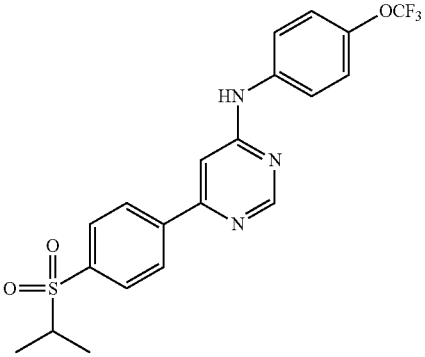 [SMILES: CC(C)S(=O)(=O)c1ccc(-c2cc(Nc3ccc(OC(F)(F)F)cc3)ncn2)cc1] | MS m/z 438.20 (M + 1). | >10 | 0.45 | 4.8 |
| 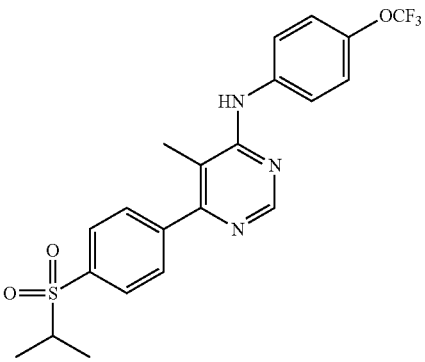 [SMILES: Cc1c(Nc2ccc(OC(F)(F)F)cc2)ncnc1-c1ccc(S(=O)(=O)C(C)C)cc1] | MS m/z 453.12 (M + 1). | >10 | 2.04 | 9.95 |
| 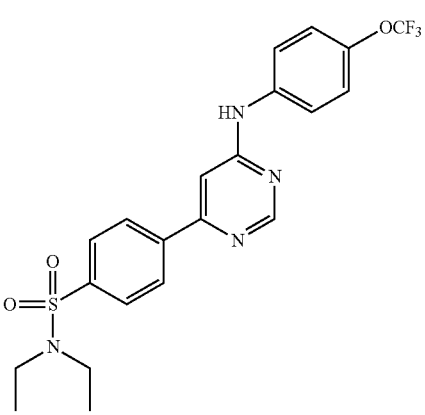 [SMILES: CCN(CC)S(=O)(=O)c1ccc(-c2cc(Nc3ccc(OC(F)(F)F)cc3)ncn2)cc1] | MS m/z 467.21 (M + 1). | 8.85 | 0.59 | 3.88 |
| 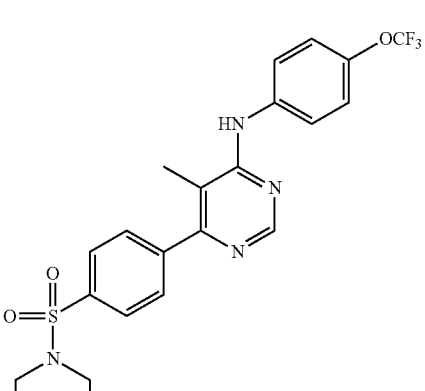 | MS m/z 481.30 (M + 1). | >10 | 3.96 | 9.19 |

TABLE 16-continued
| Structure | Spectroscopy | BaF3 | Bcr-Abl | T315I |
|---|---|---|---|---|
| 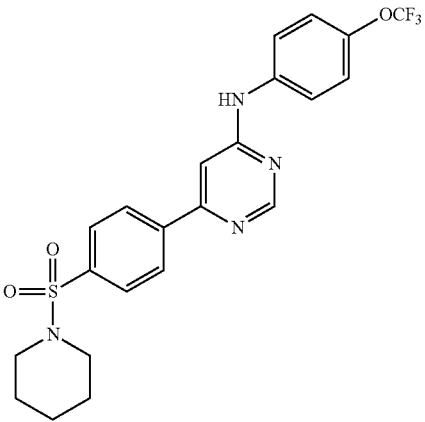 [SMILES: O=S(=O)(c1ccc(-c2cc(Nc3ccc(OC(F)(F)F)cc3)ncn2)cc1)N1CCCCC1] | MS m/z 479.03 (M + 1). | >10 | 1.06 | 1.41 |
| 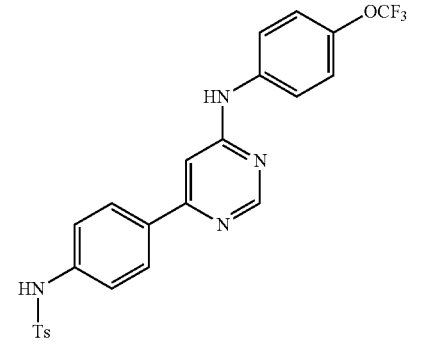 [SMILES: Cc1ccc(S(=O)(=O)Nc2ccc(-c3cc(Nc4ccc(OC(F)(F)F)cc4)ncn3)cc2)cc1] | MS m/z 501.22 (M + 1). | >10 | 1.19 | >10 |
| 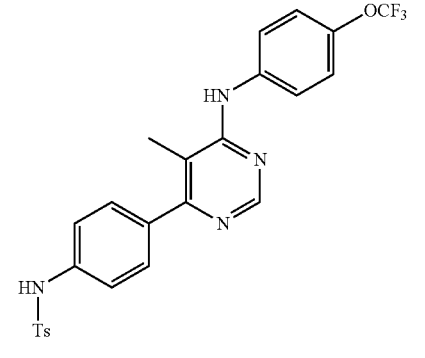 [SMILES: Cc1ccc(S(=O)(=O)Nc2ccc(-c3ncnc(Nc4ccc(OC(F)(F)F)cc4)c3C)cc2)cc1] | MS m/z 515.32 (M + 1). | >10 | 4.32 | >10 |
| 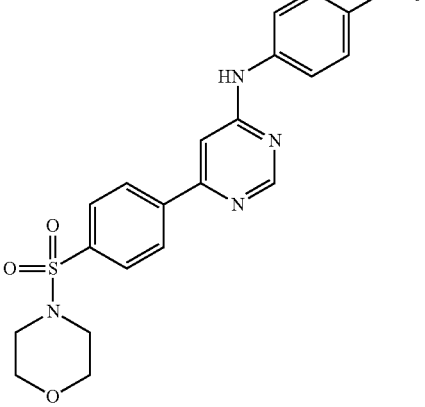 | MS m/z 481.10 (M + 1). | >10 | 0.50 | 2.63 |

TABLE 16-continued
| Structure | Spectroscopy | BaF3 | Bcr-Abl | T315I |
|---|---|---|---|---|
| 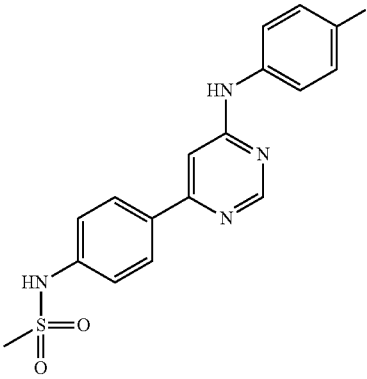 | $^1$H NMR 400 MHz (DMSO-d$_6$) δ 10.09 (s, 1H), 8.80 (s, 1H), 8.24 (d, 2H, J = 8.8 Hz), 7.94 (d, 2H, J = 8.8 Hz), 7.85 (d, 2H, J = 9.2 Hz), 7.38 (d, 2H, J = 8.4 Hz), 7.33 (d, 1H, J = 0.8 Hz), 2.47 (d, 3H, J = 4.8 Hz)); MS m/z 425.02 (M + 1). | 2.21 | 0.04 | 0.600 |
| 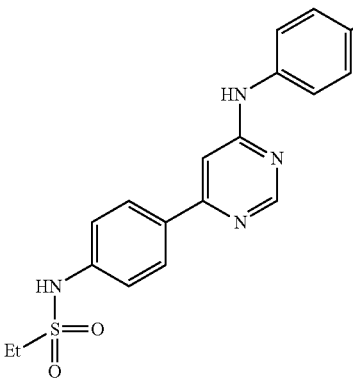 | MS m/z 439.04 (M + 1). | 8.31 | 0.46 | 2.18 |
| 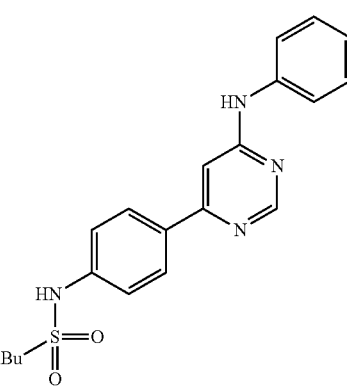 | MS m/z 467.10 (M + 1). | 8.92 | 0.51 | 2.89 |
| 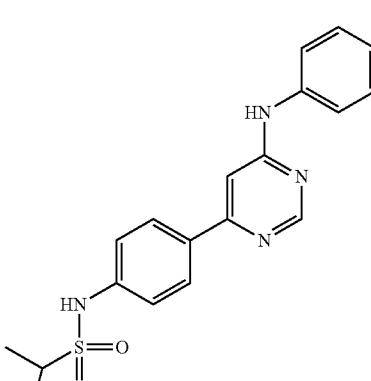 | MS m/z 453.21 (M + 1). | 6.93 | 0.51 | 2.25 |

TABLE 16-continued
| Structure | Spectroscopy | BaF3 | Bcr-Abl | T315I |
|---|---|---|---|---|
| 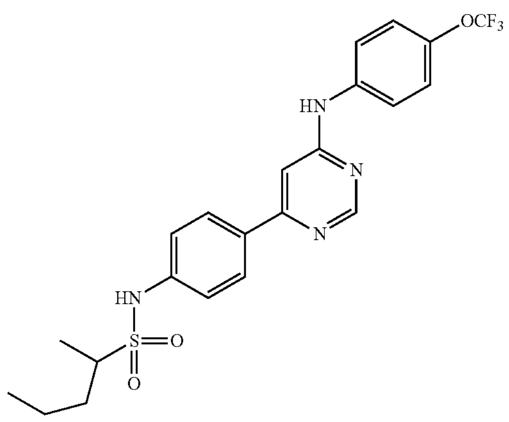 [SMILES: CCCC(C)S(=O)(=O)Nc1ccc(-c2cc(Nc3ccc(OC(F)(F)F)cc3)ncn2)cc1] | MS m/z 481.12 (M + 1). | 3.80 | 0.68 | 1.66 |
| 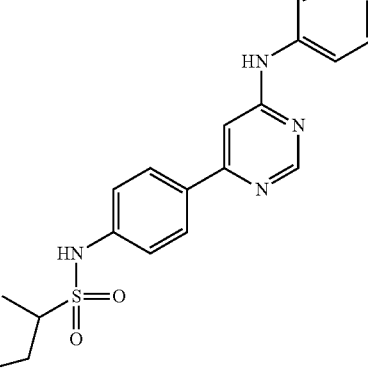 | MS m/z 433.20 (M + 1). | >10 | 0.42 | 4.67 |
| 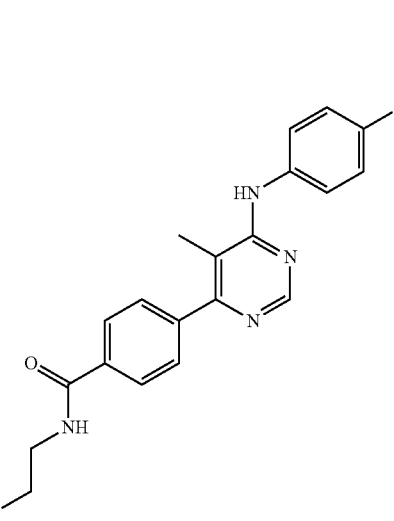 | MS m/z 502.23 (M + 1). | 3.79 | 0.14 | 0.81 |
| 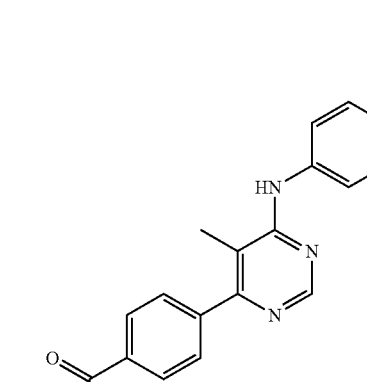 | | | | |

TABLE 16-continued

| Structure | Spectroscopy | BaF3 | Bcr-Abl | T315I |
|---|---|---|---|---|
| 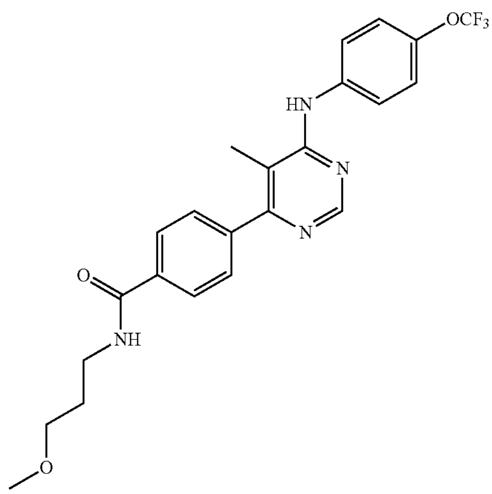 [SMILES: COCCCNC(=O)c1ccc(-c2ncnc(Nc3ccc(OC(F)(F)F)cc3)c2C)cc1] | MS m/z 461.10 (M + 1). | 3.11 | 0.29 | 1.85 |
| 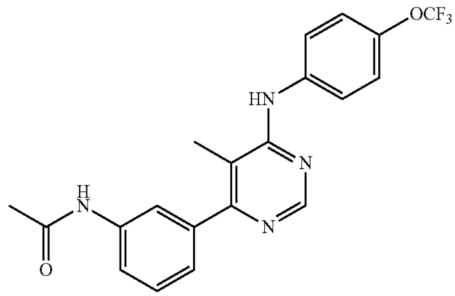 [SMILES: CC(=O)Nc1cccc(-c2ncnc(Nc3ccc(OC(F)(F)F)cc3)c2C)c1] | MS m/z 403.12 (M + 1). | >10 | 3.97 | >10 |
| 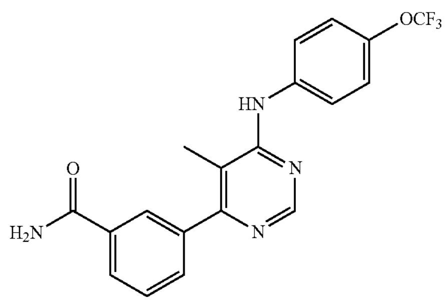 [SMILES: Cc1c(Nc2ccc(OC(F)(F)F)cc2)ncnc1-c1cccc(C(N)=O)c1] | MS m/z 389.12 (M + 1). | >10 | 0.80 | >10 |
| 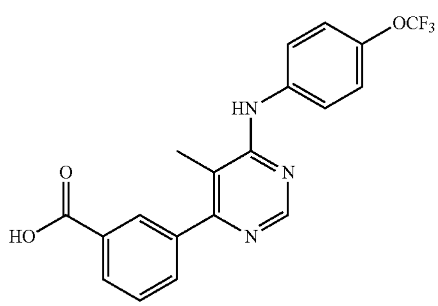 [SMILES: Cc1c(Nc2ccc(OC(F)(F)F)cc2)ncnc1-c1cccc(C(=O)O)c1] | MS m/z 390.10 (M + 1). | >10 | 6.09 | >10 |

TABLE 16-continued

| Structure | Spectroscopy | BaF3 | Bcr-Abl | T315I |
|---|---|---|---|---|
| 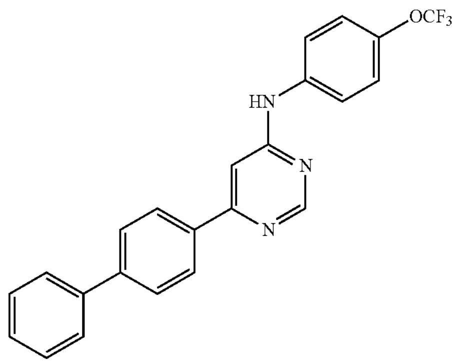 [SMILES: FC(F)(F)Oc1ccc(Nc2cc(-c3ccc(-c4ccccc4)cc3)ncn2)cc1] | MS m/z 408.20 (M + 1). | >10 | 1.48 | 3.18 |
| 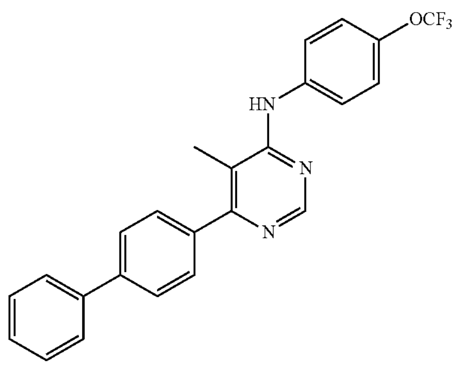 [SMILES: Cc1c(Nc2ccc(OC(F)(F)F)cc2)ncnc1-c1ccc(-c2ccccc2)cc1] | MS m/z 422.23 (M + 1). | >10 | >10 | >10 |
| 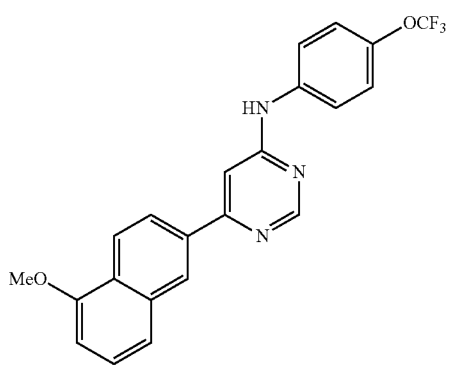 | MS m/z 412.12 (M + 1). | >10 | 0.62 | >10 |
| 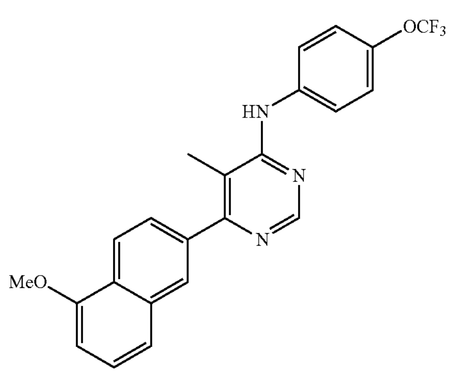 | MS m/z 426.40 (M + 1). | >10 | >10 | >10 |

TABLE 16-continued

| Structure | Spectroscopy | BaF3 | Bcr-Abl | T315I |
|---|---|---|---|---|
| 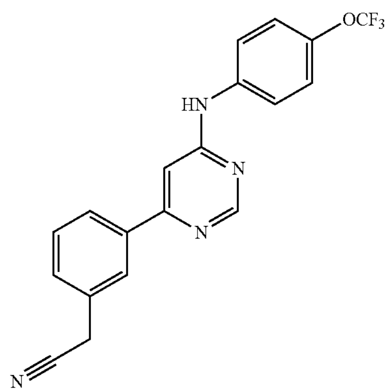 [SMILES: N#CCc1cccc(-c2cc(Nc3ccc(OC(F)(F)F)cc3)ncn2)c1] | MS m/z 371.10 (M + 1). | 8.82 | 0.24 | 3.39 |
| 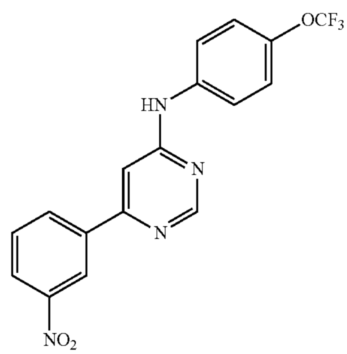 [SMILES: O=[N+]([O-])c1cccc(-c2cc(Nc3ccc(OC(F)(F)F)cc3)ncn2)c1] | MS m/z 377.06 (M + 1). | >10 | 0.55 | >10 |
| 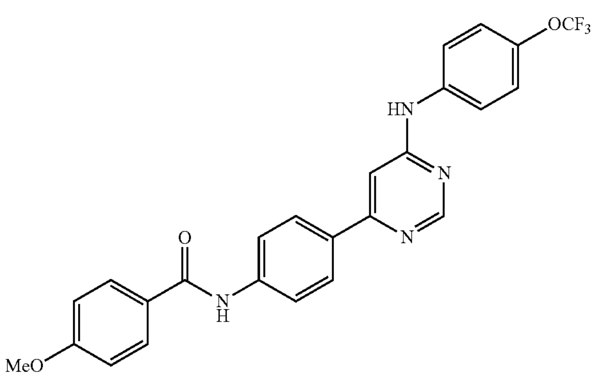 [SMILES: COc1ccc(C(=O)Nc2ccc(-c3cc(Nc4ccc(OC(F)(F)F)cc4)ncn3)cc2)cc1] | MS m/z 481.24 (M + 1). | 9.22 | >10 | >10 |
| 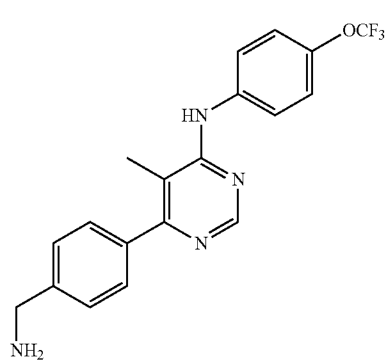 [SMILES: Cc1c(Nc2ccc(OC(F)(F)F)cc2)ncnc1-c1ccc(CN)cc1] | MS m/z 375.12 (M + 1). | >10 | >10 | >10 |

TABLE 16-continued

| Structure | Spectroscopy | BaF3 | Bcr-Abl | T315I |
|---|---|---|---|---|
| 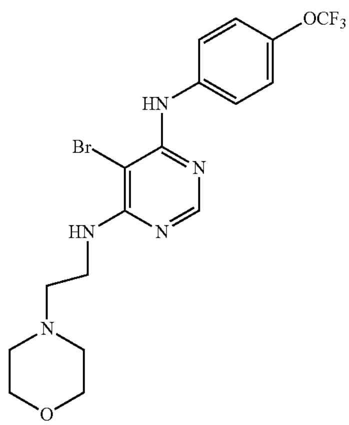 [SMILES: FC(F)(F)Oc1ccc(Nc2ncnc(NCCN3CCOCC3)c2Br)cc1] | MS m/z 462.01 (M + 1). | >10 | >10 | >10 |
| 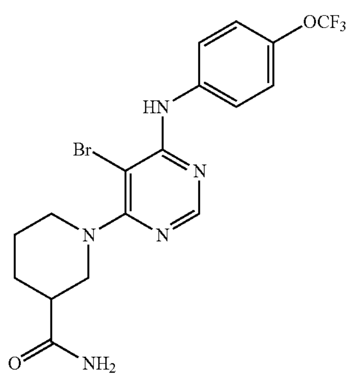 [SMILES: NC(=O)C1CCCN(c2ncnc(Nc3ccc(OC(F)(F)F)cc3)c2Br)C1] | MS m/z 460.20 (M + 1). | >10 | 4.00 | >10 |
| 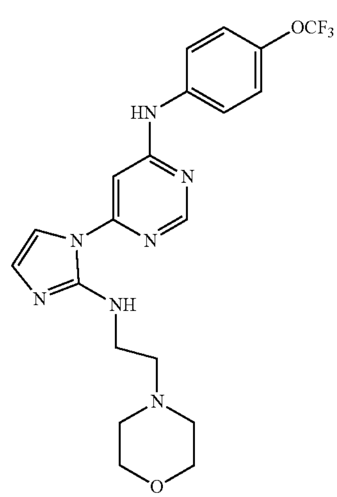 [SMILES: FC(F)(F)Oc1ccc(Nc2cc(-n3ccnc3NCCN3CCOCC3)ncn2)cc1] | MS m/z 450.10 (M + 1). | >10 | >10 | >10 |

TABLE 16-continued

| Structure | Spectroscopy | BaF3 | Bcr-Abl | T315I |
|---|---|---|---|---|
| 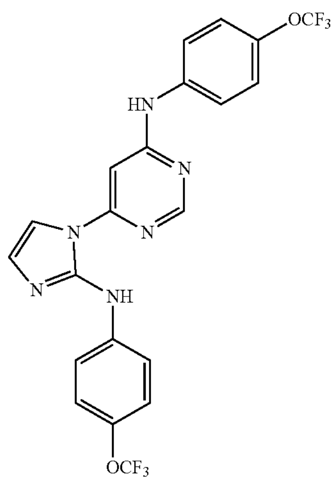 [SMILES: FC(F)(F)Oc1ccc(Nc2cc(-n3ccnc3Nc3ccc(OC(F)(F)F)cc3)ncn2)cc1] | MS m/z 497.12 (M + 1). | >10 | >10 | >10 |
| 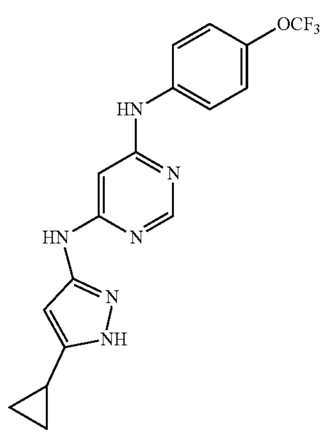 [SMILES: FC(F)(F)Oc1ccc(Nc2cc(Nc3cc(C4CC4)[nH]n3)ncn2)cc1] | MS m/z 377.10 (M + 1). | 5.62 | 0.24 | 3.27 |
| 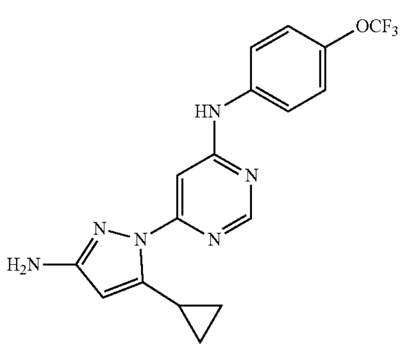 [SMILES: Nc1cc(C2CC2)n(-c2cc(Nc3ccc(OC(F)(F)F)cc3)ncn2)n1] | MS m/z 377.08 (M + 1). | >10 | 2.18 | >10 |

TABLE 16-continued

| Structure | Spectroscopy | BaF3 | Bcr-Abl | T315I |
|---|---|---|---|---|
| 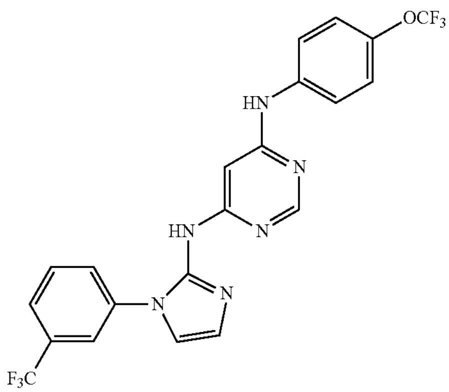 [SMILES: FC(F)(F)Oc1ccc(Nc2cc(Nc3nccn3-c3cccc(C(F)(F)F)c3)ncn2)cc1] | MS m/z 481.11 (M + 1). | 2.56 | 0.82 | 1.48 |
| 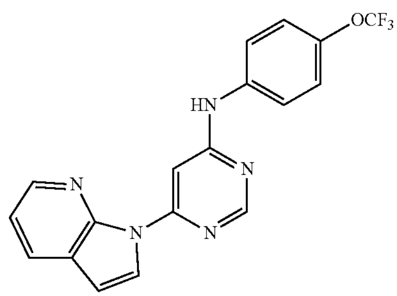 [SMILES: FC(F)(F)Oc1ccc(Nc2cc(-n3ccc4cccnc43)ncn2)cc1] | MS m/z 372.10 (M + 1). | >10 | 7.14 | >10 |
| | ¹H NMR 400 MHz (DMSO-d₆) δ 10.52 (s, 1H), 8.84 (s, 1H), 8.42 (s, 2H), 7.86 (d, 2H, J = 9.2 Hz), 7.48 (d, 2H, J = 9.2 Hz), 7.14 (s, 1H). MS m/z 322.02 (M + 1). | >10 | 0.090 | 0.46? |
| 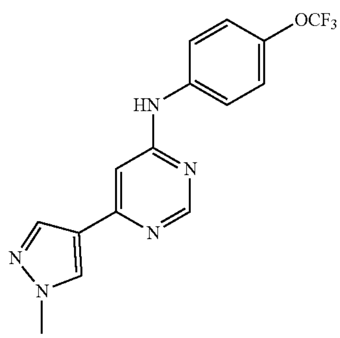 [SMILES: Cn1cc(-c2cc(Nc3ccc(OC(F)(F)F)cc3)ncn2)cn1] | MS m/z 336.10 (M + 1). | >10 | 0.10 | 3.10 |

TABLE 16-continued

| Structure | Spectroscopy | BaF3 | Bcr-Abl | T315I |
|---|---|---|---|---|
| (structure: 4-OCF3-phenyl-NH-pyrimidine-pyrazole-N-isobutyl) | MS m/z 378.12 (M + 1). | >10 | 0.36 | 1.55 |
| (structure: 4-OCF3-phenyl-NH-(5-methyl)pyrimidine-pyrazole-N-isobutyl) | MS m/z 392.21 (M + 1). | 1.46 | 0.36 | 1.55 |
| (structure: 4-OCF3-phenyl-NH-pyrimidine-(3,5-dimethyl,N-methyl)pyrazole) | ¹H NMR 400 MHz (DMSO-d₆) δ 10.32 (s, 1H), 8.75 (s, 1H), 8.39 (s, 2H), 7.84 (d, 2H, J = 9.2 Hz), 7.45 (d, 2H, J = 9.2 Hz), 3.84 (s, 3H), 2.89 (s, 3H), 2.24 (s, 3H). (M + 1). MS m/z 364.11 (M + 1). | >10 | 0.150 | >10 |
| (structure: 4-OCF3-phenyl-NH-pyrimidine-pyrazole-N-CH2-(4-methylsulfonyl-phenyl)) | MS m/z 390.21 (M + 1). | >10 | 0.160 | >10 |

TABLE 16-continued

| Structure | Spectroscopy | BaF3 | Bcr-Abl | T315I |
|---|---|---|---|---|
| 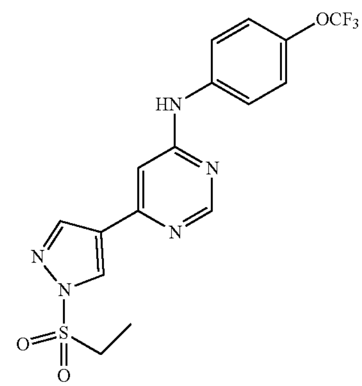 [SMILES: CCS(=O)(=O)n1cc(-c2cc(Nc3ccc(OC(F)(F)F)cc3)ncn2)cn1] | MS m/z 414.24 (M + 1). | >10 | 0.150 | 4.25 |
| 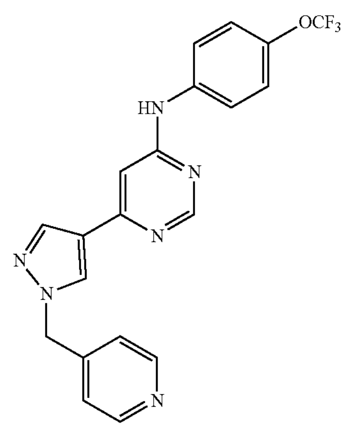 [SMILES: FC(F)(F)Oc1ccc(Nc2cc(-c3cnn(Cc4ccncc4)c3)ncn2)cc1] | MS m/z 413.02 (M + 1). | 7.3 | 0.19 | 4.00 |
| 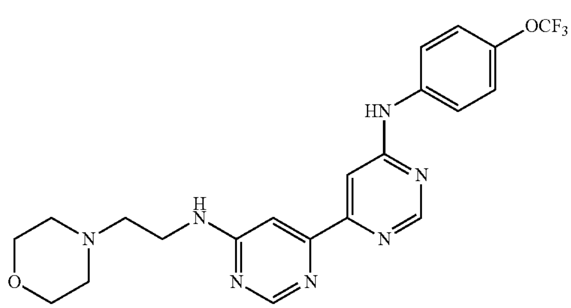 [SMILES: FC(F)(F)Oc1ccc(Nc2cc(-c3cc(NCCN4CCOCC4)ncn3)ncn2)cc1] | MS m/z 462.12 (M + 1). | >10 | 0.90 | 9.8 |
| 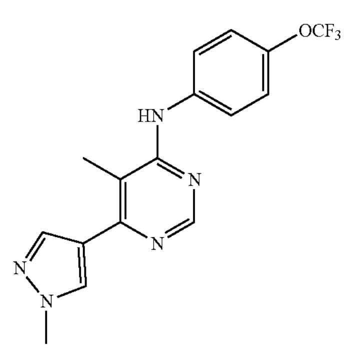 [SMILES: Cc1c(Nc2ccc(OC(F)(F)F)cc2)ncnc1-c1cnn(C)c1] | MS m/z 350.12 (M + 1). | >10 | 0.49 | 3.00 |

TABLE 16-continued

| Structure | Spectroscopy | BaF3 | Bcr-Abl | T315I |
|---|---|---|---|---|
| (4-OCF3-phenyl)-NH-pyrimidine-(1-phenyl-5-methyl-pyrazol-4-yl) | MS m/z 412.10 (M + 1). | >10 | 0.81 | 6.23 |
| (4-OCF3-phenyl)-NH-(5-methylpyrimidine)-(1-phenyl-5-methyl-pyrazol-4-yl) | ¹H NMR 400 MHz (DMSO-d₆) δ 9.8 (s, 1H), 8.75 (s, 1H), 7.99 (s, 1H), 7.75 (d, 2H, J = 9.2 Hz), 7.64-7.58 (m, 4H), 7.53-7.51 (m, 1H), 7.45 (d, 2H, J = 9.2 Hz), 2.37 (s, 3H), 2.31 (s, 3H), MS m/z 426.01 (M + 1). | 8.85 | 1.79 | 5.24 |
| (4-OCF3-phenyl)-NH-pyrimidine-(1H-indol-4-yl) | MS m/z 371.01 (M + 1). | >10 | 0.14 | 6.67 |
| (4-OCF3-phenyl)-NH-pyrimidine-(1H-indol-3-yl) | MS m/z 371.10 (M + 1). | >10 | 1.4 | 9.28 |

TABLE 16-continued

| Structure | Spectroscopy | BaF3 | Bcr-Abl | T315I |
|---|---|---|---|---|
| 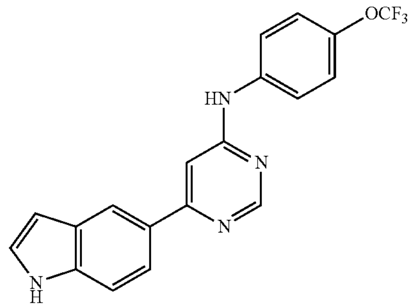 [SMILES: FC(F)(F)Oc1ccc(Nc2cc(-c3ccc4[nH]ccc4c3)ncn2)cc1] | MS m/z 371.21 (M + 1). | >10 | 0.29 | 8.71 |
| 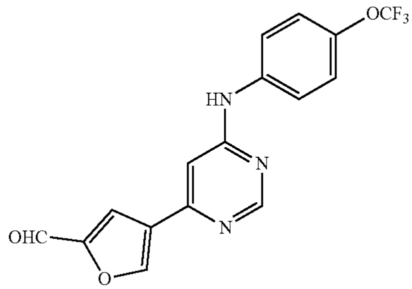 [SMILES: O=Cc1cc(-c2cc(Nc3ccc(OC(F)(F)F)cc3)ncn2)co1] | MS m/z 350.54 (M + 1). | >10 | 0.94 | 3.83 |
| 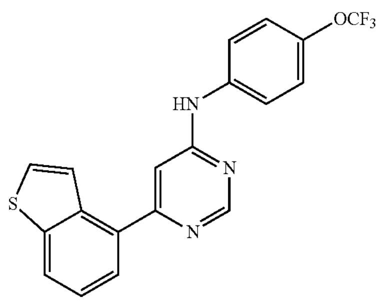 [SMILES: FC(F)(F)Oc1ccc(Nc2cc(-c3cccc4sccc34)ncn2)cc1] | MS m/z 388.20 (M + 1). | 3.06 | 1.76 | 3.74 |
| 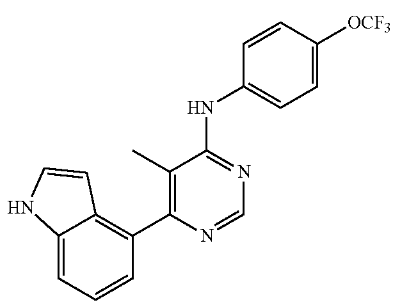 [SMILES: Cc1c(Nc2ccc(OC(F)(F)F)cc2)ncnc1-c1cccc2[nH]ccc12] | MS m/z 385.12 (M + 1). | >10 | >10 | >10 |
| 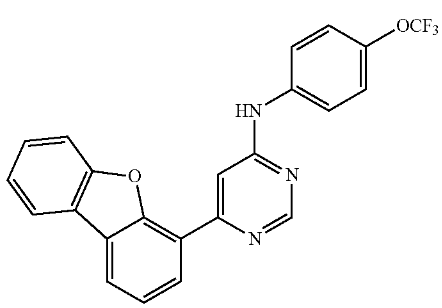 [SMILES: FC(F)(F)Oc1ccc(Nc2cc(-c3cccc4c3oc3ccccc34)ncn2)cc1] | MS m/z 422.04 (M + 1). | >10 | 1.9 | 4.6 |

TABLE 16-continued

| Structure | Spectroscopy | BaF3 | Bcr-Abl | T315I |
|---|---|---|---|---|
| 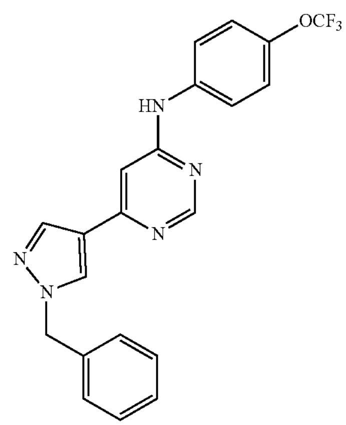 [SMILES: FC(F)(F)Oc1ccc(Nc2cc(-c3cnn(Cc4ccccc4)c3)ncn2)cc1] | MS m/z 412.12 (M + 1). | >10 | 0.17 | 1.30 |
| 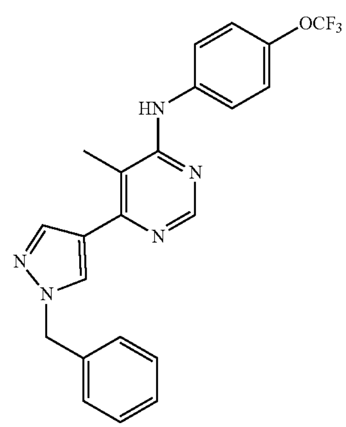 [SMILES: Cc1c(Nc2ccc(OC(F)(F)F)cc2)ncnc1-c1cnn(Cc2ccccc2)c1] | MS m/z 426.20 (M + 1). | 9.9 | 1.82 | 8.72 |
| 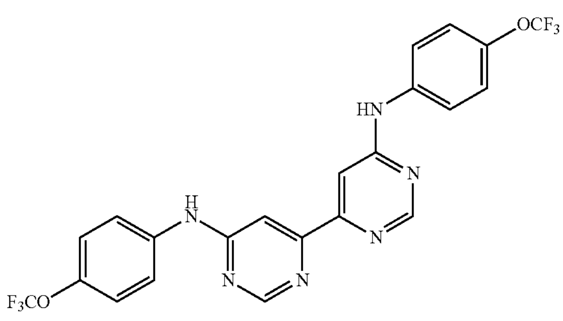 [SMILES: FC(F)(F)Oc1ccc(Nc2cc(-c3cc(Nc4ccc(OC(F)(F)F)cc4)ncn3)ncn2)cc1] | MS m/z 509.12 (M + 1). | >10 | >10 | 7 |
| 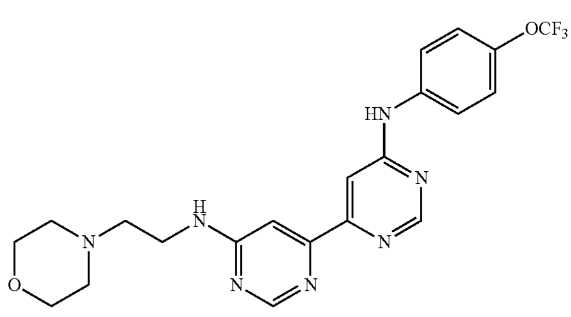 [SMILES: FC(F)(F)Oc1ccc(Nc2cc(-c3cc(NCCN4CCOCC4)ncn3)ncn2)cc1] | MS m/z 462.18 (M + 1). | >10 | 6.69 | >10 |

TABLE 16-continued
| Structure | Spectroscopy | BaF3 | Bcr-Abl | T315I |
|---|---|---|---|---|
| 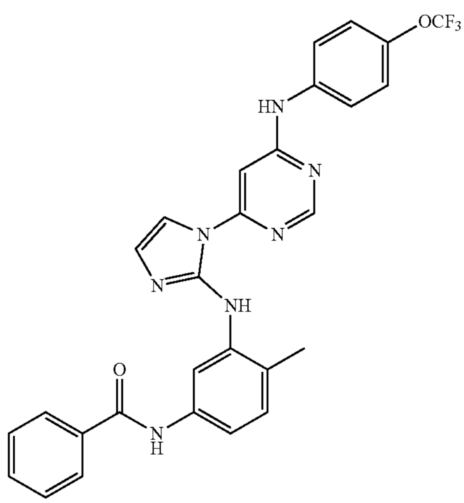 [SMILES: Cc1ccc(NC(=O)c2ccccc2)cc1Nc1nccn1-c1cc(Nc2ccc(OC(F)(F)F)cc2)ncn1] | MS m/z 546.33 (M + 1). | >10 | 3.63 | >10 |
| 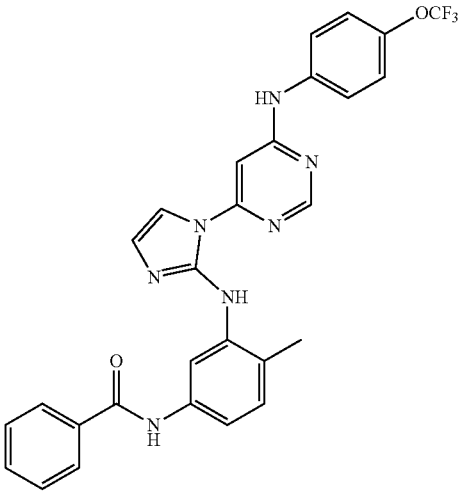 | | | | |
| 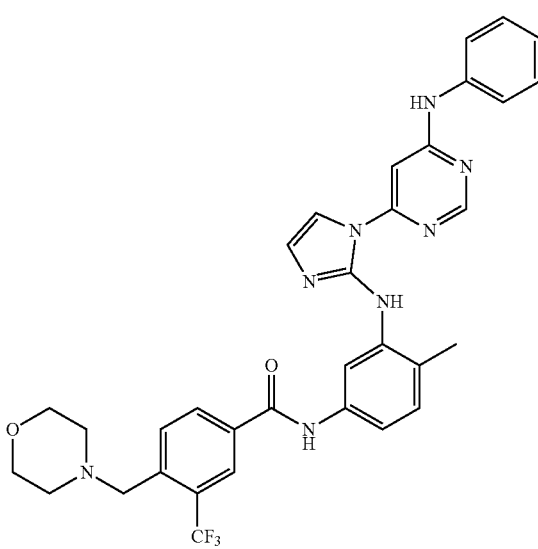 | MS m/z 713.01 (M + 1). | >10 | 6.25 | 6.61 |
| 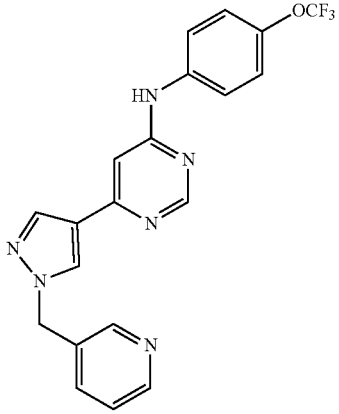 [SMILES: FC(F)(F)Oc1ccc(Nc2cc(-c3cnn(Cc4cccnc4)c3)ncn2)cc1] | MS m/z 413.11 (M + 1). | >10 | 0.4 | 9.0 |

TABLE 16-continued

| Structure | Spectroscopy | BaF3 | Bcr-Abl | T315I |
|---|---|---|---|---|
| (4-trifluoromethoxyphenyl)amino-pyrimidine-7-azaindole structure | MS m/z 372.14 (M + 1). | 6.85 | 0.166 | >10 |
| (4-trifluoromethoxyphenyl)amino-pyrimidine-2-pyridinone structure | MS m/z 349.01 (M + 1). | >10 | 0.196 | >10 |
| (4-trifluoromethoxyphenyl)amino-pyrimidine-2-methylthiazole structure | $^1$H NMR 400 MHz (DMSO-$d_6$) δ 9.96 (s, 1H), 8.67 (s, 1H), 8.24 (s, 1H), 7.84 (d, 2H, J = 9.2 Hz), 7.50 (d, 1H, J = 0.8 Hz), 7.35 (d, 2H, J = 9.2 Hz), 2.74 (s, 3H). MS m/z 352.03 (M + 1). | >10 | 1.23 | >10 |
| (4-trifluoromethoxyphenyl)amino-pyrimidine-fluoro-formylphenyl structure | MS m/z 378.02 (M + 1). | 4.12 | 0.849 | 5.844 |

TABLE 16-continued
| Structure | Spectroscopy | BaF3 | Bcr-Abl | T315I |
|---|---|---|---|---|
| 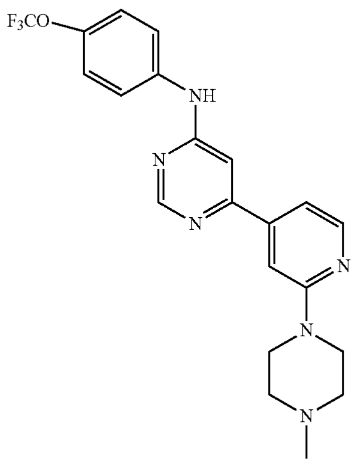 [SMILES: CN1CCN(c2cc(-c3cc(Nc4ccc(OC(F)(F)F)cc4)ncn3)ccn2)CC1] | MS m/z 431.20 (M + 1). | 0.710 | 0.049 | 0.386 |
TABLE 17
| Structure | Spectroscopy | BaF3 | Bcr-Abl | T315I |
|---|---|---|---|---|
| | ¹H NMR 400 MHz (DMSO-d₆) δ 10.42 (s, 1H), 8.88 (s, 1H), 8.67 (s, 1H), 8.01-7.99 (m, 3H), 7.92 (d, 2H, J = 9.2 Hz), 7.53 (d, 2H, J = 9.2 Hz), 7.45 (s, 1H), 7.22 (s, 1H). MS m/z 416.12 (M + 1). | 9.60 | 2.94 | 6.29 |
| 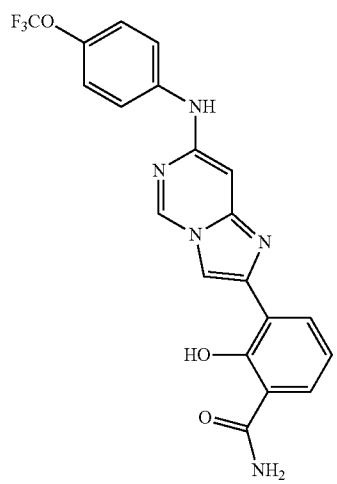 [SMILES: NC(=O)c1cccc(-c2cn3cnc(Nc4ccc(OC(F)(F)F)cc4)cc3n2)c1O] | MS m/z 430.02 (M + 1). | | | |

TABLE 17-continued

| Structure | Spectroscopy | BaF3 | Bcr-Abl | T315I |
|---|---|---|---|---|
| 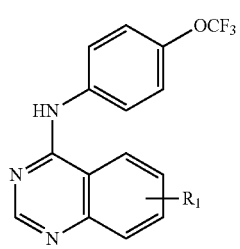 | MS m/z 512.92 (M + 1). | >10 | >10 | >10 |

INCORPORATION BY REFERENCE

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A compound of formula VII, or pharmaceutically acceptable salt thereof, (VII)

wherein
$R_1$ is selected from a substituted $C_{1-6}$alkyl, —C(O)$R^x$, (CH$_2$)$_n$C(O)$R^x$, (CH$_2$)$_n$C(O)O$R^x$, (CH$_2$)$_n$C(O)N$R^x R^x$, or —(CH$_2$)$_n$C(O)N$R^x R^x$S(O)$_2 R^x$;
$R^x$, for each occurrence, is independently H, an optionally substituted $C_{1-6}$alkyl, an optionally substituted $C_{3-12}$cycloalkyl, an optionally substituted $C_{3-12}$heterocycloalkyl, an optionally substituted $C_{3-12}$aryl, an optionally substituted $C_{3-12}$heteroaryl, NHNH$R_2$, or C(NH)NH$_2$;
$R_2$ is H or $C_{1-4}$ alkyl; and
each n is independently 0, 1 or 2,
wherein the substituted $C_{1-6}$alkyl is not ethyl.

2. The compound of claim 1, selected from:
4-(4-(trifluoromethoxy)phenylamino)-N-(2-hydroxy-ethyl)quinazoline-7-carboxamide;
4-(4-Trifluoromethoxy-phenylamino)-quinazoline-7-carboxylic acid methyl ester;
[4-(4-Trifluoromethoxy-phenylamino)-quinazolin-7-yl]-methanol;
(7-Diethylaminomethyl-quinazolin-4-yl)-(4-trifluoromethoxy-phenyl)-amine;
4-(4-Trifluoromethoxy-phenylamino)-quinazoline-7-carboxylic acid diethylamide;
[4-(Furan-3-carbonyl)-piperazin-1-yl]-[4-(4-trifluoromethoxy-phenylamino)-quinazolin-7-yl]-methanone;
4-(4-Trifluoromethoxy-phenylamino)-quinazoline-7-carboxylic acid (3-trifluoromethyl-phenyl)-amide;
4-(4-Trifluoromethoxy-phenylamino)-quinazoline-7-carboxylic acid (3-methoxy-propyl)-amide;
4-(4-Trifluoromethoxy-phenylamino)-quinazoline-7-carboxylic acid N'-ethyl-hydrazide;
(2-{[4-(4-Trifluoromethoxy-phenylamino)-quinazoline-7-carbonyl]-amino}-thiazol-5-yl)-acetic acid ethyl ester;
(4-Methoxy-piperidin-1-yl)-[4-(4-trifluoromethoxy-phenylamino)-quinazolin-7-yl]-methanone;
(3-Hydroxy-pyrrolidin-1-yl)-[4-(4-trifluoromethoxy-phenylamino)-quinazolin-7-yl]-methanone;
(2-Hydroxymethyl-pyrrolidin-1-yl)-[4-(4-trifluoromethoxy-phenylamino)-quinazolin-7-yl]-methanone;
(3-Dimethylamino-pyrrolidin-1-yl)-[4-(4-trifluoromethoxy-phenylamino)-quinazolin-7-yl]-methanone;
4-(4-Trifluoromethoxy-phenylamino)-quinazoline-7-carboxylic acid (2-hydroxy-ethyl)-methyl-amide;
4-(4-Trifluoromethoxy-phenylamino)-quinazoline-7-carboxylic acid methyl-(1-methyl-piperidin-4-yl)-amide;
4-Methyl-N-[4-(4-trifluoromethoxy-phenylamino)-quinazoline-7-carbonyl]-benzenesulfonamide;
2-Methyl-propane-2-sulfonic acid [4-(4-trifluoromethoxy-phenylamino)-quinazoline-7-carbonyl]-amide;
(4-Methyl-[1,4]diazepan-1-yl)-[4-(4-trifluoromethoxy-phenylamino)-quinazolin-7-yl]-methanone;

(3,5-Dimethyl-piperazin-1-yl)-[4-(4-trifluoromethoxy-phenylamino)-quinazolin-7-yl]-methanone;

(4-Hydroxy-piperidin-1-yl)-[4-(4-trifluoromethoxy-phenylamino)-quinazolin-7-yl]-methanone;

4-(4-Trifluoromethoxy-phenylamino)-quinazoline-7-carboxylic acid methyl-(2-methylamino-ethyl)-amide;

4-(4-Trifluoromethoxy-phenylamino)-quinazoline-7-carboxylic acid (2-hydroxy-ethyl)-amide;

1-Phenyl-8-[4-(4-trifluoromethoxy-phenylamino)-quinazoline-7-carbonyl]-1,3,8-triaza-spiro[4.5]decan-4-one;

(4-Bromo-piperidin-1-yl)-[4-(4-trifluoromethoxy-phenylamino)-quinazolin-7-yl]-methanone;

1-[4-(4-Trifluoromethoxy-phenylamino)-quinazoline-7-carbonyl]-piperidine-4-carboxylic acid amide;

1-[4-(4-Trifluoromethoxy-phenylamino)-quinazoline-7-carbonyl]-piperidine-3-carboxylic acid amide;

1-[4-(4-Trifluoromethoxy-phenylamino)-quinazoline-7-carbonyl]-piperidine-3-carboxylic acid ethyl ester; and (3-Hydroxymethyl-piperidin-1-yl)-[4-(4-trifluoromethoxy-phenylamino)-quinazolin-7-yl]-methanone.

3. A pharmaceutical composition comprising a compound, or pharmaceutically acceptable salt thereof, of claim 1.

4. The pharmaceutical composition of claim 3, further comprising an additional therapeutic agent that inhibits the ATP-site.

* * * * *